(12) United States Patent
Toscano et al.

(10) Patent No.: US 9,862,699 B2
(45) Date of Patent: Jan. 9, 2018

(54) MELDRUM'S ACID, BARBITURIC ACID AND PYRAZOLONE DERIVATIVES SUBSTITUTED WITH HYDROXYLAMINE AS HNO DONORS

(71) Applicant: The Johns Hopkins University, Baltimore, MA (US)

(72) Inventors: John P. Toscano, Glen Arm, MD (US); Daryl A. Guthrie, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/290,872

(22) Filed: Oct. 11, 2016

(65) Prior Publication Data

US 2017/0050947 A1    Feb. 23, 2017

Related U.S. Application Data

(62) Division of application No. 14/927,039, filed on Oct. 29, 2015, now Pat. No. 9,499,511, which is a division of application No. 14/352,399, filed as application No. PCT/US2012/060425 on Oct. 16, 2012, now Pat. No. 9,181,213.

(60) Provisional application No. 61/548,036, filed on Oct. 17, 2011.

(51) Int. Cl.
*C07D 319/06* (2006.01)
*C07D 239/62* (2006.01)
*C07D 231/22* (2006.01)
*C07D 231/46* (2006.01)
*C07D 231/08* (2006.01)

(52) U.S. Cl.
CPC ......... *C07D 319/06* (2013.01); *C07D 231/08* (2013.01); *C07D 231/22* (2013.01); *C07D 231/46* (2013.01); *C07D 239/62* (2013.01)

(58) Field of Classification Search
None
See application file for complete search history.

(56) References Cited

U.S. PATENT DOCUMENTS

| | | |
|---|---|---|
| 3,751,255 A | 8/1973 | Wilson et al. |
| 4,369,174 A | 1/1983 | Nagai et al. |
| 4,539,321 A | 9/1985 | Campbell |
| 4,663,351 A | 5/1987 | Diamond |
| 4,798,824 A | 1/1989 | Belzer et al. |
| 4,842,866 A | 6/1989 | Horder et al. |
| 5,217,720 A | 6/1993 | Sekigawa et al. |
| 6,525,081 B1 | 2/2003 | Matsumoto et al. |
| 6,569,457 B2 | 5/2003 | Ullah et al. |
| 6,638,534 B1 | 10/2003 | Ishibashi et al. |
| 6,936,639 B2 | 8/2005 | Wink et al. |
| 7,696,373 B2 | 4/2010 | King |
| 7,863,262 B2 | 1/2011 | Wink et al. |
| 8,030,356 B2 | 10/2011 | Toscano et al. |
| 8,227,639 B2 | 7/2012 | Toscano et al. |
| 8,268,890 B2 | 9/2012 | Wink et al. |
| 8,318,705 B2 | 11/2012 | Frost et al. |
| 8,674,132 B2 | 3/2014 | Toscano et al. |
| 8,791,134 B2 | 7/2014 | Frost et al. |
| RE45,314 E | 12/2014 | Toscano et al. |
| 9,018,411 B2 | 4/2015 | Toscano et al. |
| 9,181,213 B2 | 11/2015 | Toscano et al. |
| 2004/0038947 A1 | 2/2004 | Wink et al. |
| 2005/0153966 A1 | 7/2005 | Gangloff et al. |
| 2005/0192254 A1 | 9/2005 | Wink et al. |
| 2009/0186045 A1 | 7/2009 | Ray et al. |
| 2009/0281067 A1 | 11/2009 | Toscano et al. |
| 2009/0298795 A1 | 12/2009 | Paolocci et al. |
| 2011/0081427 A1 | 4/2011 | Wink et al. |
| 2011/0136827 A1 | 6/2011 | Toscano et al. |
| 2011/0144067 A1 | 6/2011 | Toscano et al. |
| 2011/0160200 A1 | 6/2011 | Mazhari et al. |
| 2011/0306614 A1 | 12/2011 | Toscano et al. |
| 2012/0201907 A1 | 8/2012 | Wink et al. |
| 2014/0194416 A1 | 7/2014 | Toscano et al. |
| 2014/0235636 A1 | 8/2014 | Toscano et al. |
| 2014/0275134 A1 | 9/2014 | Toscano et al. |
| 2014/0336137 A1 | 11/2014 | Frost et al. |

(Continued)

FOREIGN PATENT DOCUMENTS

| | | |
|---|---|---|
| CN | 101472576 | 7/2009 |
| CN | 102076342 | 5/2011 |

(Continued)

OTHER PUBLICATIONS

Badesch, D.B. et al., "Diagnosis and Assessment of Pulmonary Arterial Hypertension", In Journal of the American College of Cardiology, vol. 54, No. 1s1, Jun. 2009, pp. S55-S66.
Crawford, J.H. et al., "Hypoxia, Red Blood Cells, and Nitrite Regulate NO-Dependent Hypoxic Vasodilation", In Blood, vol. 107, No. 2, Jan. 2006, pp. 566-575.
Fukuto, J.M. et al., "The Physiological Chemistry and Biological Activity of Nitroxyl (HNO): The Neglected, Misunderstood, and Enigmatic Nitrogen Oxide", In Chemical Research in Toxicology, vol. 18, No. 5, May 2005, pp. 790-801.
Gao, W.D. et al., "Myofilament Ca2+ Sensitivity in Intact Versus Skinned Rat Ventricular Muscle", In Circulation Research, vol. 74, No. 3, Mar. 1994, pp. 408-415.

(Continued)

*Primary Examiner* — Kamal Saeed
(74) *Attorney, Agent, or Firm* — Byrne Poh LLP; Nina R. Horan

(57) ABSTRACT

The disclosed subject matter provides certain N-substituted hydroxylamine derivative compounds, pharmaceutical compositions and kits comprising such compounds, and methods of using such compounds or pharmaceutical compositions. In particular, the disclosed subject matter provides methods of using such compounds or pharmaceutical compositions for treating, preventing, or delaying the onset and/or development of a disease or condition. In some embodiments, the disease or condition is selected from cardiovascular diseases, ischemia, reperfusion injury, cancerous disease, pulmonary hypertension and conditions responsive to nitroxyl therapy.

11 Claims, 4 Drawing Sheets

(56) References Cited

U.S. PATENT DOCUMENTS

| | | |
|---|---|---|
| 2014/0336396 A1 | 11/2014 | Toscano et al. |
| 2015/0004259 A1 | 1/2015 | Wink et al. |
| 2015/0141378 A1 | 5/2015 | Toscano et al. |
| 2015/0344437 A1 | 12/2015 | Kalish et al. |
| 2016/0060229 A1 | 3/2016 | Toscano et al. |
| 2016/0115148 A1 | 4/2016 | Toscano et al. |

FOREIGN PATENT DOCUMENTS

| | | |
|---|---|---|
| JP | 2011523404 | 8/2011 |
| WO | WO/2007/002444 | 12/1899 |
| WO | WO/2001/010827 | 2/2001 |
| WO | WO/2002/100810 | 12/2002 |
| WO | WO/2005/074598 | 8/2005 |
| WO | WO/2006/086188 | 8/2006 |
| WO | WO/2007/109175 | 9/2007 |
| WO | WO/2009/042970 | 4/2009 |
| WO | WO/2009/137717 | 11/2009 |
| WO | WO/2011/063339 | 5/2011 |
| WO | WO/2013/059194 | 4/2013 |
| WO | WO/2014/113700 | 7/2014 |
| WO | WO/2015/183838 | 3/2015 |
| WO | WO/2015/183839 | 3/2015 |

OTHER PUBLICATIONS

Gao, W.D. el al., "Relationship Between Intracellular Calcium and Contractile Force in Stunned Mocardium: Direct Evidence for Decreased Myofilament CA2+ Responsiveness and Altered Diastolic Function in Intact Ventricular Muscle", In Circulation Research, vol. 76, No. 6, Jun. 1995, pp. 1036-1048.

Hare, J.M. et al., "Pertussis Toxin-Sensitive G Proteins Influence Nitric Oxide Synthase III Activity and Protein Levels in Rat Heart", In the Journal of Clinical Investigations, vol. 101, No. 6, Mar. 1998, pp. 1424-1431.

Ingall, T.J., "Preventing Ischemic Stroke", In Postgraduate Medicine, vol. 107, No. 6, May 2000, pp. 34-50.

Katori, T. et al., "Calcitonin Gene-Related Peptide in Vivo Positive Inotropy is Attributable to Regional Sympatho-Stimulation and is Blunted in Congestive Heart Failure", In Circulation Research, vol. 96, No. 2, Feb. 2005, pp. 234-243.

Ma, X.L. et al., "Opposite Effects of Nitric Oxide and Nitroxyl on Postischemic Myocardial Injury", In Proceedings of the National Academy of Sciences of the United States of America, vol. 96, No. 25, Dec. 1999, pp. 14617-14622.

Mincione, F. et al., "Carbonic Anhydrase Inhibitors: Inhibition of Isozymes I, II and IV with N-Hydroxysulfonamides—A Novel Class of Intraocular Pressure Lowering Agents", In the Journal of Enzyme Inhibition and Medicinal Chemistry, vol. 13, No. 4, Jan. 1998, pp. 267-284.

Norris, A.J. et al., "Nitroxyl Inhibits Breast Tumor Growth and Angiogenesis", In the International Journal of Cancer, vol. 122, No. 8, Apr. 2008, pp. 1905-1910.

Nutaitis, C.F. et al., "Reduction of Isopropylidene Acylmalonates, 5-Acylbarbituric Acids, and 3-Acyl-4-Hydroxycoumarins to the Corresponding Alkyl Derivatives by Sodium Cyanoborohydride-Acetic Acid", In the Journal of Organic Chemistry, vol. 45, No. 23, Nov. 1980, pp. 4606-4608.

Office Action dated Jan. 16, 2017 in Chinese Patent Application No. 201280051009.4.

Office Action dated Mar. 1, 2017 in Japanese Patent Application No. 2014-537151.

Office Action dated May 16, 2016 in Australian Patent Application No. 2015246114.

Office Action dated May 23, 2016 in Japanese Patent Application No. 2014-537151.

Office Action dated May 27, 2016 in European Patent Application No. 12781538.9.

Office Action dated Jul. 25, 2016 in Chinese Patent Application No. 201280051009.4.

Office Action dated Nov. 27, 2015 in Chinese Patent Application No. 201280051009.4.

Paolocci, N. et al., "cGMP-Independent Inotropic Effects of Nitric Oxide and Peroxynitrite Donors: Potential Role for Nitrosylation", In the American Journal of Physiology Heart and Circulatory Physiology, vol. 279, No. 4, Oct. 2000, pp. 111982-111988.

Raillar, S.P. et al., "Preparation and Improved Stability of N-Boc-a-Amino-5-Acyl Meldrum's Acids, a Versatile Class of Building Blocks for Combinatorial Chemistry", In the Journal of Combinatorial Chemistry, vol. 4, No. 5, Sep. 2002, pp. 470-474.

Rastaldo, R. et al., "Cytochrome P-450 Metabolite of Arachidonic Acid Mediates Bradykinin-induced Negative Inotropic Effect", In American Journal of Physiology Heart and Circulatory Physiology, vol. 280, No. 6, Jun. 2001, pp. H2823-H2832.

Simonneau, G. et al., "Updated Clinical Classification of Pulmonary Hypertension", In the Journal of the American College of Cardiology, vol. 54, No. 1s1, Jun. 2009, pp. S43-S54.

Slotwiner-Nie, P.K. and Brandt, L.J., "Infectious Diarrhea in the Elderly", In Gastroenterology Clinics, vol. 30, No. 3, Sep. 2001, pp. 625-635.

Stoyanovsky, D.A. et al., "Effects of pH on the Cytotoxicity of Sodium Trioxodinitrate (Angeli's Salt)", In the Journal of Medicinal Chemistry, vol. 47, No. 1, Dec. 2003, pp. 210-217.

Thevis, M. et al., "High Speed Determination of Beta-Receptor Blocking Agents in Human Urine by Liquid Chromatography/Tandem Mass Spectrometry", In Biomedical Chromatography, vol. 15, No. 6, Oct. 2001, pp. 393-402.

Timoshinina, L.G. and Vvedenskii, V.M., "Reaction of Dialuric Acid with Hydrazine Derivatives", In Chemistry of Heterocyclic Compounds, vol. 9, No. 2, Feb. 1973, pp. 247-249.

Yranzo, G.I. et al., "Flash Vacuum Pyrolysis of 2-Alkoxyiminated alkyl a-pyrone and 1,3-diazine Derivatives", In Journal of Analytical and Applied Pyrolysis, vol. 46, No. 2, Aug. 1998, pp. 101-112.

Andrei, D. et al., "Dual Mechanisms of HNO Generation by a Nitroxyl Prodrug of the Diazeniumdiolate (NONOate) Class", In Journal of the American Chemical Society, vol. 132, No. 46, Nov. 24, 2010, pp. 16526-16532.

Bodor, N. and Buchwald, P., "Soft Drugs", In Retrometabolic Drug Design and Targeting, John Wiley & Sons, Oct. 2012.

Bonner, F.T. and Ko, Y., "Kinetic, isotopic, and nitrogen-15 NMR study of N-hydroxybenzenesulfonamide decomposition: an nitrosyl hydride (HNO) source reaction", In Inorganic Chemistry, vol. 31, No. 12, Jun. 1, 1992, pp. 2514-2519.

Choe, C.U. et al., "Nitroxyl in the central nervous system", In Antioxidants & Redox Signaling, vol. 14, No. 9, May 1, 2011, pp. 1699-1711.

Cline, M.R. and Toscano, J.P., "Detection of nitroxyl (HNO) by a prefluorescent probe", In Journal of Physical Organic Chemistry, vol. 24, No. 10, Oct. 2011, pp. 993-998.

Cline, M.R. et al., "Oxidation of N-hydroxy-l-arginine by hypochlorous acid to form nitroxyl (HNO)", In Journal of Inorganic Biochemistry, vol. 118, Jan. 2013, pp. 148-154.

Cline, M.R., "Detection of nitroxyl (HNO) by membrane inlet mass spectrometry", In Free Radical Biology & Medicine, vol. 50, No. 10, May 2011, pp. 1274-1279.

Cohen, A.D. et al., "Direct Observation of an Acyl Nitroso Species in Solution by Time-Resolved IR Spectrocopy", In Journal of the American Chemical Society, vol. 125, No. 6, Jan. 16, 2003, pp. 1444-1445.

Corrie, J.E.T. et al., "Reactions of transient C-nitrosocarbonyl compounds with dienes, mono-olefins, and nucleophiles", In Journal of the Chemical Society, Perkin Transactions 1, 1985, pp. 883-886.

Evans, A.S. and Toscano, J.P., "The chemistry of NO- and HNO-producing diazeniumdiolates", In PATAI's Chemistry of Functional Groups, John Wiley & Sons, Ltd., Nov. 2010, pp. 1-16.

Evans, A.S. et al., "Photogeneration and reactivity of acyl nitroso compounds", In Canadian Journal of Chemistry, vol. 89, No. 2, Feb. 2011, pp. 130-138.

(56) References Cited

OTHER PUBLICATIONS

Flores-Santana, W. et al., "The Specificity of Nitroxyl Chemistry is Unique Among Nitrogen Oxides in Biological Systems", In Antioxidants & Redox Signaling, vol. 14, No. 9, May 1, 2011, pp. 1659-1674.
Freelisch, M., "Nitroxyl gets to the heart of the matter", In Proceedings of the National Academy of Sciences, vol. 100, No. 9, Apr. 2003, pp. 4978-4980.
Froehlich, J.P. et al., "Phospholamban thiols play a central role in activation of the cardiac muscle sarcoplasmic reticulum calcium pump by nitroxyl", In Biochemistry, vol. 47, No. 50, Dec. 16, 2008, pp. 13150-13152.
Gladwin, M.T. et al., "Nitrite as a vascular endocrine nitric oxide reservoir that contributes to hypoxic signaling, cytoprotection, and vasodilation", In American Journal of Physiology Heart and Circulatory Physiology, vol. 291, No. 5, Nov. 2006, pp. H2026-H2035.
Gladwin, M.T. et al., "The emerging biology of the nitrite anion", In Nature Chemical Biology, vol. 1, No. 6, Nov. 2005, pp. 308-314.
Guthrie, D.A. et al., "Development of N-Substituted Hydroxylamines as Efficient Nitroxyl (HNO) Donors", In Journal of the American Chemical Society, vol. 134, No. 4, Jan. 9, 2012, pp. 1962-1965.
Higashi, Y. et al., "Edaravone (3-methyl-1-phenyl-2-pyrazolin-5-one), a novel free radical scavenger, for treatment of cardiovascular diseases", In Recent Patents on Cardiovascular Drug Discovery, vol. 1, No. 1, Jan. 2006, pp. 85-93.
Hughes, M.N. and Cammack, R., "Synthesis, chemistry, and applications of nitroxyl ion releasers sodium trioxodinitrate or Angeli's salt and Piloty's acid", In Methods in Enzymology, vol. 301, 1999, pp. 279-287.
International Preliminary Report on Patentability dated May 1, 2014 in International Patent Application No. PCT/US2012/060425.
Keceli, G. and Toscano, J.P., "Reactivity of Nitroxyl-Derived Sulfinamides", In Biochemistry, vol. 51, No. 20, May 2012, pp. 4206-4216.
Keceli, G. et al., "NMR Detection and Study of Hydrolysis of HNO-Derived Sulfinamides", In Biochemistry, vol. 52, No. 42, Oct. 2013, pp. 7387-7396.
Kemp-Harper, B.K., "Nitroxyl (HNO): A Novel Redox Signaling Molecule", In Andioxidants & Redox Signaling, vol. 14, No. 9, May 1, 2011, pp. 1609-1613.
Miranda, K.M. et al., "Comparison of the NO and HNO donating properties of diazeniumdiolates: primary amine adducts release HNO in Vivo", In Journal of Medicinal Chemistry, vol. 48, No. 26, Dec. 29, 2005, pp. 8220-8228.
Miranda, K.M. et al., "Donors of HNO", In Current Topics in Medicinal Chemistry, vol. 5, No. 7, 2005, pp. 649-664.
Office Action dated Jan. 23, 2015 in Chinese Patent Application No. 201280051009.4.
Office Action dated Mar. 12, 2014 in Australian Patent Application No. 2013201929.
Paolocci, N. et al., "Nitroxyl anion exerts redox-sensitive positive cardiac inotropy in vivo by calcitonin gene-related peptide signaling", In Proceedings of the National Academy of Sciences, vol. 98, No. 18, Aug. 28, 2001, pp. 10463-10468.
Paolocci, N. et al., "Positive inotropic and lusitropic effects of HNO/NO- in failing hearts: Independence from β-adrenergic signaling", In Proceedings of the National Academy Sciences, vol. 100, No. 9, Apr. 29 2003 pp. 5537-5542.
Paolocci, N. et al., "The pharmacology of nitroxyl (HNO) and its therapeutic potential: Not just the janus face of NO", In Pharmacology & Therapeutics, vol. 113, No. 2, Feb. 2007, pp. 442-458.
Porcheddu, A. et al., "A Straightforward Route to Piloty's Acid Derivatives: A Class of Potential Nitroxyl-Generating Prodrugs", In Synlett, vol. 2009, No. 13, Aug. 2009, pp. 2149-2153.
Rehse, K. and Hahrouri, T., "New NO donors with antithrombotic and vasodilating activities, part 25. Hydroxylamine derivatives", In Archiv der Pharmazie, vol. 331, No. 11, Nov. 1998, pp. 365-367.
Sabbah, H.N. et al., "Nitroxyl (HNO) a Novel Approach for the Acute Treatment of Heart Failure", In Circulation: Heart Failure, vol. 6, No. 6, Nov. 2013, pp. 1250-1258.
Salmon, D.J. et al., "HNO and NO release from a primary amine-based diazeniumdiolate as a function of pH", In Inorganic Chemistry, vol. 50. No. 8, Apr. 18, 2011, pp. 3262-3270.
Sha, X. et al., "Hydrolysis of Acyloxy Nitroso Compounds Yields Nitroxyl (HNO)", In Journal of the American Chemical Society, vol. 128, No. 30, Jul. 2006, pp. 9687-9692.
Shoman, M.E. et al., "Acyloxy nitroso compounds as nitroxyl (HNO) donors: kinetics, reactions with thiols, and vasodilation properties", In Journal of Medicinal Chemistry, vol. 54, No. 4, Feb. 24, 2011, pp. 1059-1070.
Sutton, A.D. et al., "Optimization of HNO production from N,O-bis-acylated hydroxylamine derivatives", In Organic Letters, vol. 14, No. 2, Jan. 20, 2012, pp. 472-475.
Tocchetti, C.G. et al., "Nitroxyl improves cellular heart function by directly enhancing cardiac sarcoplasmic reticulum Ca2+ cycling", In Circulation Research, vol. 100, No. 1, Jan. 5, 2007, pp. 96-104.
Tocchetti, C.G. et al., "Playing with Cardiac "Redox Switches": The "HNO Way" to Modulate Cardiac Function", In Antioxidants & Redox Signaling, vol. 14, No. 9, May 1, 2011, pp. 1687-1698.
Watanabe, K. et al. "Structure-activity relationship of 3-methyl-1-phenyl-2-pyrazolin-5-one (edaravone)", In Redox Report, vol. 8, No. 3, Jun. 1, 2003, pp. 151-155.
Watanabe, T. et al., "The Novel Antioxidant Edaravone: From Bench to Bedside", In Cardiovascular Therapeutics, vol. 26, No. 2, Jun. 2008, pp. 101-114.
Xu, Y. et al., "Production of nitroxyl (HNO) at biologically relevant temperatures from the retro-Diels-Alder reaction of N-hydroxyurea-derived acyl nitroso-9,10-dimethylanthracene cycloadducts", In Tetrahedron Letters, vol. 41, No. 22, Jun. 8, 2000, pp. 4265-4269.
Zamora, R. et al., "Oxidative release of nitric oxide accounts for guanylyl cyclase stimulating, vasodilator and anti-platelet activity of Piloty's acid: a comparison with Angeli's salt", In Biochemistry Journal, vol. 312, No. 2, Dec. 1995, pp. 333-339.
Office Action dated Jun. 9, 2015 in European Patent Application No. 12781538.9.
Guthrie, D.A. et al., "Curtailing the Hydroxylaminobarbituric Acid-Hydantoin Rearrangement to Favor HNO Generation", In the Journal of Organic Chemistry, vol. 80, No. 3, Jan. 13, 2015, pp. 1349-1356.
International Search Report and Written Opinion dated Sep. 30, 2015 in International Patent Application No. PCT/US2015/032493.
Guthrie, D.A. et al., "'Catch-and-Release' of HNO with Pyrazolones", In the Journal of Organic Chemistry, vol. 80, No. 3, Jan. 16, 2015, pp. 1338-1348.
International Search Report and Written Opinion dated Sep. 18, 2015 in International Patent Application No. PCT/US2015/032496.
Notice of Allowance dated Jun. 7, 2016 in U.S. Appl. No. 14/926,607.
Tate et al., "Preparation of 5-Substituted Benzylbarburituric Acid and Investigation of the Effects of the Benzyl and Substituted Benzyl Groups on the Acidity of Barituric Acid", In the Journal of Heterocyclic Chemistry, Jan. 1986, pp. 9-11.

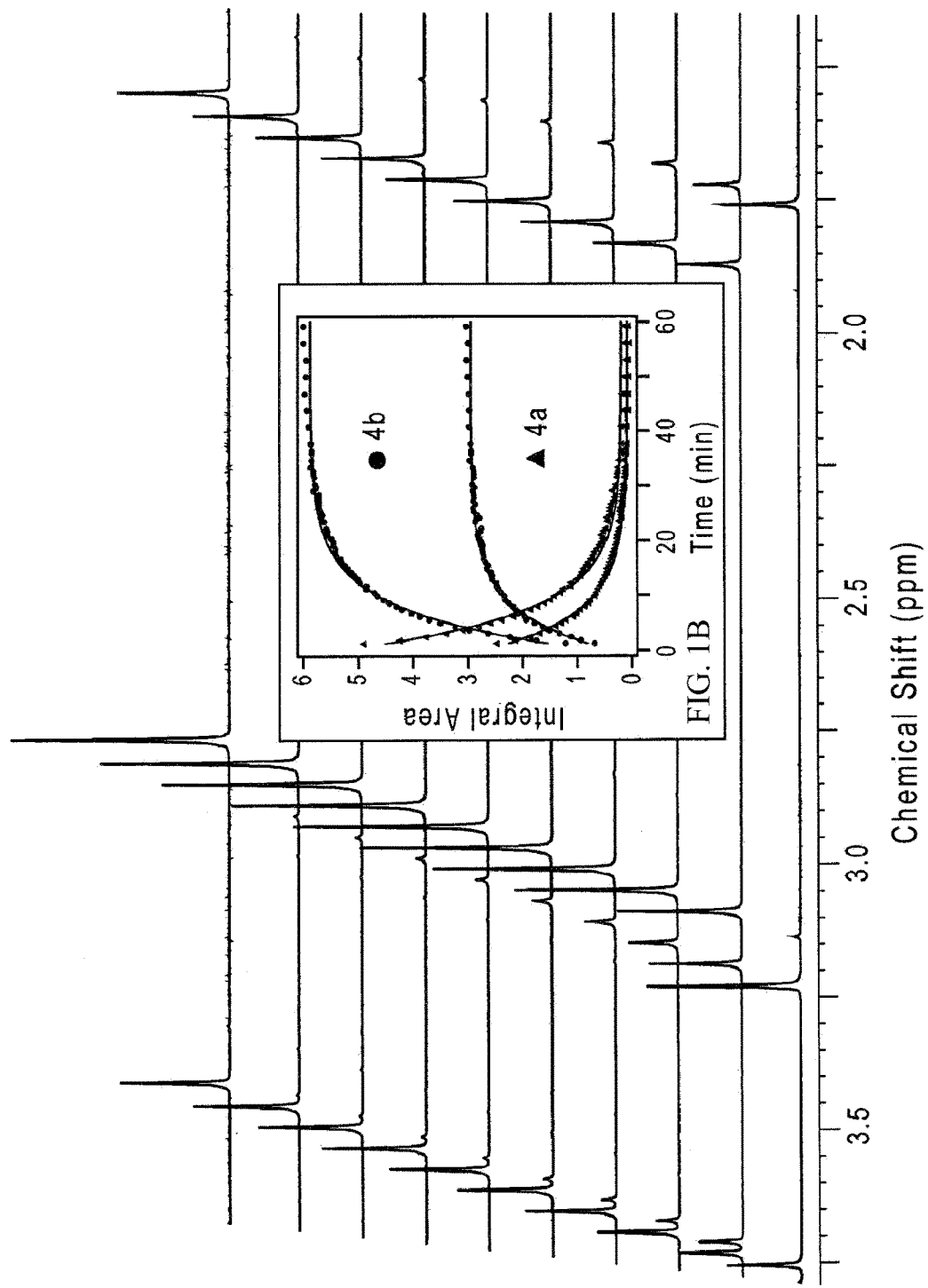

MELDRUM'S ACID, BARBITURIC ACID AND PYRAZOLONE DERIVATIVES SUBSTITUTED WITH HYDROXYLAMINE AS HNO DONORS This application is a divisional application of U.S. application Ser. No. 14/927,039, filed Oct. 29, 2015, which is a divisional application of U.S. application Ser. No. 14/352,399, filed Apr. 17, 2014, now U.S. Pat. No. 9,181,213, issued Nov. 10, 2015, which is a National Stage of International Application No. PCT/US2012/060425, filed Oct. 16, 2012, which claims the benefit under 35 U.S.C. §119(e) of U.S. Provisional Patent Application No. 61/548,036, filed Oct. 17, 2011, entitled "N-Substituted Hydroxylamine Derivatives with Carbon-Based Leaving Groups as Physiologically Useful Nitroxyl (HNO) Donors", the contents of all of which are incorporated herein by reference.

This invention was made in part with government support under Grant No. CHE-0911305 awarded by the National Science Foundation (NSF). The government may have certain rights in this invention.

Nitroxyl (HNO) has been shown to have biological activity distinct from that of its redox cousin, nitric oxide (NO), and related nitrogen oxides.[1-11] Much of the recent interest in HNO has been catalyzed by research suggesting that it may be a novel therapeutic for the treatment of heart failure.[1-5] At neutral pH in the absence of chemical traps, HNO efficiently dimerizes ($k=8\times10^6$ M$^{-1}$ s$^{-1}$) to hyponitrous acid (HON=NOH), which subsequently dehydrates to nitrous oxide ($N_2O$).[12] Given this inherent reactivity, HNO cannot be used directly; donor molecules are required for the generation of HNO in situ. However, beyond Angeli's salt, derivatives of Piloty's acid, and acyloxy nitroso compounds, few physiologically useful HNO donors exist.

N-hydroxycyanamide is a hydroxylamine derivative with a carbon-based leaving group and a proposed intermediate in the oxidative bioactivation of cyanamide by catalase, which can disproportionate to HNO and cyanide. N-Hydroxycyanamide has never been isolated to substantiate its reactivity. Evidence exist that further oxidation of N-hydroxycyanamide yields intermediates that can also generate HNO. Nagasawa and co-workers have synthesized an N,O-bis-acylated derivative of N-hydroxycyanamide, but this derivative releases HNO along with cyanide via an acyl nitroso intermediate only under enzymatic or basic conditions. Given the toxicity of cyanide, alternative carbon-based leaving groups are desired.

Described herein are N-substituted hydroxylamine derivatives with carbon-based leaving groups suitable for HNO generation at neutral pH without enzymatic activation. In addition, these derivatives avoid the release of toxic cyanide.

BRIEF DESCRIPTION OF THE DRAWINGS

FIG. 1A and FIG. 1C show $^1$H NMR analysis of the decomposition of 4a to 4b (FIG. 1A) and 6a to 6b (FIG. 1C) in 10% $D_2O$, phosphate buffered saline (PBS), pH 7.4 at room temperature. In each case, the bottom spectrum was collected at the start of the experiment, and the top spectrum after complete decomposition. In FIG. 1B, the kinetics of decomposition are shown. The triangles represent the N—CH$_3$'s (6H) and the oxime C—CH$_3$ (3H) of 4a, and the circles represent the N—CH$_3$'s (6H) and the oxime C—CH$_3$ (3H) of carbanion 4b. The solid curves are calculated best fits to a single exponential function ($k=2.4\times10^{-3}$ s$^{-1}$ for each fit). In FIG. 1C, the asterisks (*) indicate signals due to the minor anti-6b isomer.

In FIG. 2A, the squares represent 4b-H$^+$ ($\lambda_{max}$=298 nm), and the circles represent carbanion 4b ($\lambda_{max}$=261 nm). In FIG. 2B, the squares represent 6b-H$^+$ ($\lambda_{max}$=270 nm), where the last three data points were omitted due to spectral overlap, and the circles represent carbanion 6b ($\lambda_{max}$=253 nm).

DETAILED DESCRIPTION OF THE INVENTION

Definitions

Figure 1C:
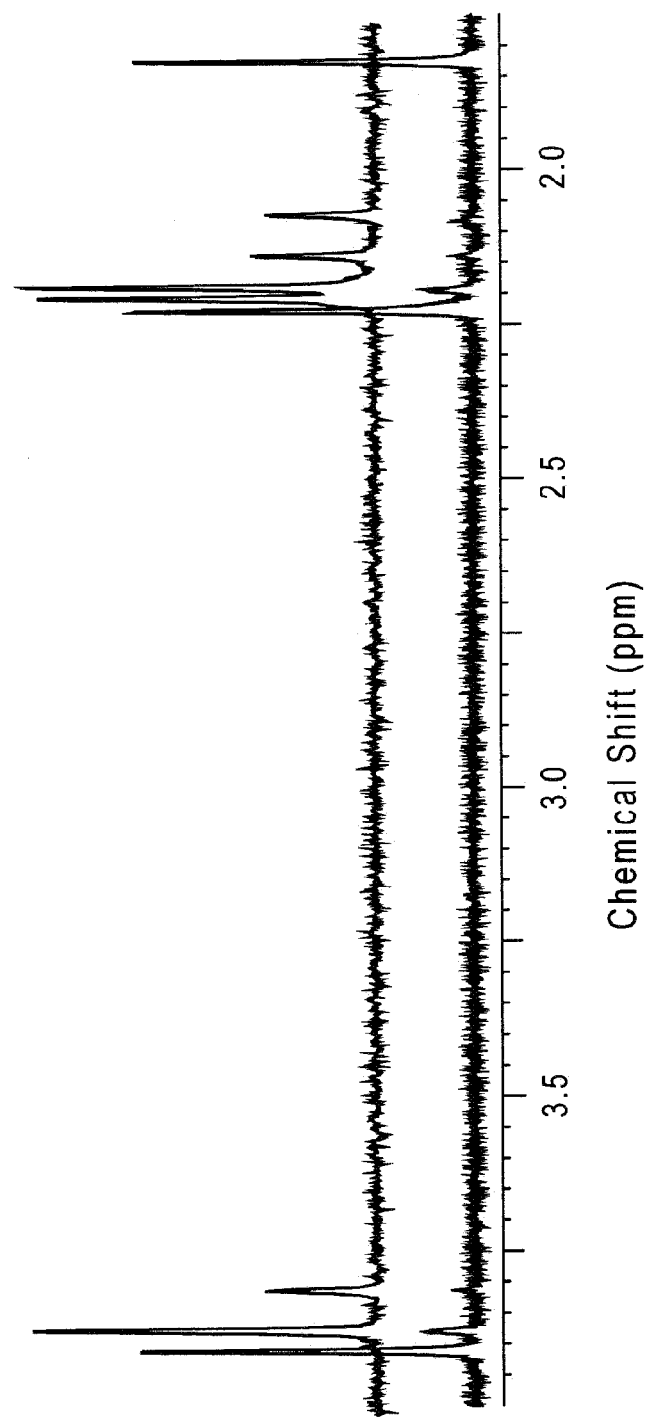

"Hr" or "h" refers to hour.
"Min" or "m" refers to minute.
"Sec" or " " refers to seconds.
"D" refers to day.
"Substituted" refers to a group or compound having one or more hydrogen atoms replaced with one or more substituents which may be the same or different. In some embodiments, the one or more substituents are those which do not substantially impair the stability or activity of the compound.

"Alkyl" refers to a monovalent hydrocarbon group containing only single carbon-carbon bonds. An alkyl group may be straight, branched, cyclic, or any combination thereof.

Unless indicated otherwise, any use of the term "alkyl" embraces all variations and geometric isomers, as if each alkyl group, or range of alkyl groups as measured by a specified number of carbon atoms, was explicitly and individually listed. For instance, $C_1$-$C_8$ alkyl encompasses $C_1$-$C_6$ alkyl, $C_1$-$C_4$, $C_1$-$C_2$ alkyl, methyl, ethyl, propyl, n-propyl, iso-propyl, n-butyl, sec-butyl, isobutyl and tert-butyl, n-pentyl, sec-pentyl, iso-pentyl, neopentyl, n-hexyl, sec-hexyl, n-heptyl, n-octyl, cyclohexyl, (cyclohexyl)methyl, and (cyclopropyl)methyl. In some embodiments, the alkyl is $C_1$-$C_{20}$ alkyl. In some embodiments, the alkyl is $C_1$-$C_8$ alkyl. In some embodiments, the alkyl is $C_1$-$C_4$ alkyl.

"Alkenyl" refers to an alkyl group having one or more carbon-carbon double bonds in place of one or more carbon-carbon single bonds. Examples of alkenyl groups include without limitation ethenyl, propenyl, butenyl, 1-methyl-2-buten-1-yl, 1,3-butadienyl, pentenyl, hexenyl, octenyl, cyclopropenyl, cyclobutenyl, cyclopentenyl, 1-cyclohexenyl, 3-cyclohexenyl and 1,3-cyclohexadienyl.

"Alkynyl" refers to an alkyl group having one or more carbon-carbon triple bonds in place of one or more carbon-carbon single bonds. Examples of alkynyl groups include without limitation ethynyl, 2-propynyl, 1-propynyl, pentynyl, 2-hexynyl, heptynyl.

"Heterocycloalkyl" refers to a monocyclic, bicyclic or polycyclic alkyl group having one or more annular heteroatoms independently selected from oxygen, nitrogen and sulfur, wherein the nitrogen and sulfur heteroatoms may optionally be oxidized and the nitrogen heteroatom may optionally be quaternized. A heterocycloalkyl group can be attached to the parent structure through a carbon or heteroatom. Examples of heterocycloalkyl groups include without limitation aziridinyl, oxiranyl, thiiranyl, azetidinyl, oxetanyl, thietanyl, pyrrolidinyl, tetrahydrofuranyl, oxalanyl, thiolanyl, imidazolidinyl, pyrazolidinyl, oxazolidinyl, isoxazolidinyl, thiazolidinyl, isothiazolidinyl, dioxolanyl, dithiolanyl, piperidinyl, oxanyl, thianyl, piperazinyl, morpholino, thiomorpholino, dioxanyl, dithianyl, trioxanyl, 1-piperidinyl, 2-piperidinyl, 3-piperidinyl, 4-morpholino, 3-morpholino, tetrahydrofuran-2-yl, tetrahydrofuran-3-yl, tetrahydrothien-2-yl, tetrahydrothien-3-yl, 1-piperazinyl, 2-piperazinyl. In some embodiments, the heterocycloalkyl contains one to three heteroatoms. In some embodiments, the heterocycloalkyl contains one to two heteroatoms. In some embodiments, the heterocycloalkyl is fused to an aryl or heteroaryl group. In some embodiments, the heterocycloalkyl is $C_5$-$C_{10}$ heterocycloalkyl. In some embodiments, the heterocycloalkyl is $C_5$-$C_6$ heterocycloalkyl.

"Heterocycloalkenyl" refers to a monocyclic, bicyclic or polycyclic alkenyl group having one or more annular heteroatoms independently selected from, oxygen, nitrogen and sulfur, wherein the nitrogen and sulfur heteroatoms may optionally be oxidized and the nitrogen heteroatom may optionally be quaternized. A heterocycloalkenyl group can be attached to the parent structure through a carbon or heteroatom. Examples of heterocycloalkenyl groups include without limitation pyranyl, thiopyranyl and tetrahydropyridyl. In some embodiments, the heterocycloalkenyl contains one to three heteroatoms. In some embodiments, the heterocycloalkyl contains one to two heteroatoms. In some embodiments, the heterocycloalkenyl is fused to an aryl or heteroaryl group. In some embodiments, the heterocycloalkenyl is $C_5$-$C_{10}$ heterocycloalkenyl. In some embodiments, the heterocycloalkenyl is $C_5$-$C_6$ heterocycloalkenyl.

"Aryl" refers to a monovalent aromatic hydrocarbon group which may be monocyclic, bicyclic or polycyclic. Examples of aryl groups include without limitation phenyl, naphthyl, indanyl, indenyl and tetralinyl. In some embodiments, the aryl is $C_5$-$C_6$ aryl. In some embodiments, the aryl is a bicyclic $C_9$-$C_{10}$ aryl. In some embodiments, the aryl is a tricyclic $C_{13}$-$C_{14}$ aryl. In some embodiments, the aryl is phenyl. In some embodiments, the aryl is naphthyl.

"Heteroaryl" refers to an aryl group having one or more annular heteroatoms independently selected from oxygen, nitrogen and sulfur. A heteroaryl group can be attached to the parent structure through a carbon or heteroatom. Examples of heteroaryl groups include without limitation imidazolyl, pyridinyl, pyrrolyl, indolyl, thiophenyl, benzopyrano, thiazolyl, furanyl, benzimidazolyl, benzoxazolyl, benzothiazolyl, quinolinyl, isoquinolinyl, quinoxalinyl, pyrimidinyl, pyrazinyl, tetrazolyl and pyrazolyl. In some embodiments, the heteroaryl is $C_5$-$C_6$ heteroaryl. In some embodiments, the heteroaryl is a bicyclic $C_9$-$C_{10}$ heteroaryl. In some embodiments, the heteroaryl is a tricyclic $C_{13}$-$C_{14}$ heteroaryl. In some embodiments, the heteroaryl is pyridinyl.

"Alkoxy" refers to an alkyl group that is connected to the parent structure through an oxygen atom (—O-alkyl). Examples of alkoxy groups include without limitation methoxy, ethoxy, propoxy, isopropoxy, cyclopropyloxy and cyclohexyloxy.

"Pharmaceutically acceptable" refers to those properties and/or substances that are acceptable to the patient from a pharmacological and/or toxicological point of view, and/or to the manufacturing pharmaceutical chemist from a physical and/or chemical point of view regarding composition, formulation, stability, patient acceptance, bioavailability and compatibility with other ingredients.

"Pharmaceutically acceptable salt" refers to pharmaceutically acceptable salts of a compound described herein, such as a compound of formula (I), (Ia) or (II) or other nitroxyl donors, which salts may be derived from a variety of organic and inorganic counter ions well known in the art and include, by way of example, sodium, potassium, calcium, magnesium, ammonium, tetraalkylammonium, and the like; when the molecule contains a basic functionality, salts of organic or inorganic acids, such as hydrochloride, hydrobromide, tartrate, mesylate, acetate, maleate, oxalate and the like. Illustrative salts include, but are not limited, to sulfate, citrate, acetate, chloride, bromide, iodide, nitrate, bisulfate, phosphate, acid phosphate, lactate, salicylate, acid citrate, tartrate, oleate, tannate, pantothenate, bitartrate, ascorbate, succinate, maleate, besylate, fumarate, gluconate, glucaronate, saccharate, formate, benzoate, glutamate, methanesulfonate, ethanesulfonate, benzenesulfonate, and p-toluenesulfonate salts. Accordingly, a salt may be prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl) amine, or tri-(2-hydroxyethyl) amine; N-methyl-D-glucamine; and amino acids such as arginine, lysine, and the like. A salt may also be prepared from a compound of any one of the formulae disclosed herein having a basic functional group, such as an amino functional group, and a pharmaceutically acceptable inorganic or organic acid. Suitable acids include hydrogen sulfate, citric acid, acetic acid, hydrochloric acid (HCl), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

"Pharmaceutically acceptable excipient" refers to any substance, not itself a therapeutic agent, used as a carrier, diluent, adjuvant, binder, and/or vehicle for delivery of a therapeutic agent to a patient, or added to a pharmaceutical composition to improve its handling or storage properties or to permit or facilitate formation of a compound or composition into a unit dosage form for administration. Pharmaceutically acceptable excipients are well known in the pharmaceutical arts and are described, for example, in Remington's Pharmaceutical Sciences, Mack Publishing Co., Easton, Pa. (e.g., $20^{th}$ Ed., 2000), and Handbook of Pharmaceutical Excipients, American Pharmaceutical Association, Washington, D.C., (e.g., $1^{st}$, $2^{nd}$ and $3^{rd}$ Eds., 1986, 1994 and 2000, respectively). As will be known to those skilled in the art, pharmaceutically acceptable excipients may provide a variety of functions and may be described as wetting agents, buffering agents, suspending agents, lubricating agents, emulsifiers, disintegrants, absorbents, preservatives, surfactants, colorants, flavorants, and sweeteners. Examples of pharmaceutically acceptable excipients include without limitation: (1) sugars, such as lactose, glucose and sucrose; (2) starches, such as corn starch and potato starch; (3) cellulose and its derivatives, such as sodium carboxymethyl cellulose, ethyl cellulose, cellulose acetate, hydroxypropylmethylcellulose, and hydroxypropylcellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

"Unit dosage form" refers to a physically discrete unit suitable as a unitary dosage for human or other animal patients. Each unit dosage form may contain a predetermined amount of an active substance (e.g., a compound of formula (I), (Ia) or (II)) calculated to produce a desired effect.

Unless clearly indicated otherwise, an "individual" or "patient" refers to an animal, such as a mammal, including but not limited, to a human. Hence, the methods described herein can be useful in human therapy and veterinary applications. In some embodiments, the individual or patient is a mammal. In some embodiments, the individual or patient is a human.

"Effective amount" refers to such amount of a compound or a pharmaceutically acceptable salt thereof, which in combination with its parameters of efficacy and toxicity, as well as based on the knowledge of the practicing specialist should be effective in a given therapeutic form. As is understood in the art, an effective amount may be in one or more doses.

"Treatment" or "treating" is an approach for obtaining a beneficial or desired result, including clinical results. For purposes of this invention, beneficial or desired results include but are not limited to inhibiting and/or suppressing the onset and/or development of a disease or condition or reducing the severity of such disease or condition, such as reducing the number and/or severity of symptoms associated with the disease or condition, increasing the quality of life of those suffering from the disease or condition, decreasing the dose of other medications required to treat the disease or condition, enhancing the effect of another medication an individual is taking for the disease or condition, and prolonging survival of individuals having the disease or condition.

"Preventing" refers to reducing the probability of developing a disorder or condition in an individual who does not have, but is at risk of developing a disorder or condition. An individual "at risk" may or may not have a detectable disease or condition, and may or may not have displayed a detectable disease or condition prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s).

"Nitroxyl" refers to the species HNO.

"Nitroxyl donor" or "HNO donor" refers to a compound that donates nitroxyl under physiological conditions. As used herein, nitroxyl donors may alternatively be referred to as "a compound" or "the compound." In some embodiments, the nitroxyl donor is capable of donating an effective amount of nitroxyl in vivo and has a safety profile indicating the compound would be tolerated by an individual in the amount necessary to achieve a therapeutic effect. One of ordinary skill in the art would be able to determine the safety of administering particular compounds and dosages to live subjects. One of skill in the art may also determine whether a compound is a nitroxyl donor by evaluating whether it releases HNO under physiological conditions. Compounds are easily tested for nitroxyl donation with routine experiments. Although it is impractical to directly measure whether nitroxyl is donated, several tests are accepted for determining whether a compound donates nitroxyl. For example, the compound of interest can be placed in solution, for example in phosphate buffered saline (PBS) or phosphate buffered solution at a pH of about 7.4, in a sealed container. After sufficient time for disassociation has elapsed, such as from several minutes to several hours, the headspace gas is withdrawn and analyzed to determine its composition, such as by gas chromatography and/or mass spectroscopy. If the gas $N_2O$ is formed (which occurs by HNO dimerization), the test is positive for nitroxyl donation and the compound is a nitroxyl donor. The level of nitroxyl donating ability may be expressed as a percentage of a compound's theoretical maximum. A compound that donates a "significant level of nitroxyl" intends a compound that donates 40% or more or 50% or more of its theoretical maximum amount of nitroxyl. In some embodiments, the compounds herein donate 60% or more of the theoretical maximum amount of nitroxyl. In some embodiments, the compounds herein donate 70% or more of the theoretical maximum amount of nitroxyl. In some embodiments, the compounds herein donate 80% or more of the theoretical maximum amount of nitroxyl. In some embodiments, the compounds herein donate 90% or more of the theoretical maximum amount of nitroxyl. In some embodiments, the compounds herein donate between about 70% and about 90% of the theoretical maximum amount of nitroxyl. In some embodiments, the compounds herein donate between about 85% and about 95% of the theoretical maximum amount of nitroxyl. In some embodiments, the compounds herein donate between about 90% and about 95% of the theoretical maximum amount of nitroxyl. Compounds that donate less than 40% or less than 50% of their theoretical amount of nitroxyl are still nitroxyl donors and may be used in the methods described. A compound that donates less than 50% of the theoretical amount of nitroxyl may be used in the methods described, and may require higher dosing levels as compared to compounds that donate a significant level of nitroxyl. Nitroxyl donation also can be detected by exposing the test compound to metmyoglobin ($Mb^{3+}$). Nitroxyl reacts with $Mb^{3+}$ to form an $Mb^{2+}$-NO complex, which can be detected by changes in the ultraviolet/visible spectrum or by Electron Paramagnetic Resonance (EPR). The $Mb^{2+}$-NO complex has an EPR signal centered around a g-value of about 2. Nitric oxide, on the other hand, reacts with $Mb^{3+}$ to form an $Mb^{3+}$-NO complex that is EPR silent. Accordingly, if the candidate compound reacts with $Mb^{3+}$ to form a complex detectable by common methods, such as ultraviolet/visible or EPR, then the test is positive for nitroxyl donation. Testing for nitroxyl donation may be performed at physiologically relevant pH.

"Positive inotrope" refers to an agent that causes an increase in myocardial contractile function. Such an agent includes a beta-adrenergic receptor agonist, an inhibitor of phosphodiesterase activity, and calcium-sensitizers. Beta-adrenergic receptor agonists include, among others, dopamine, dobutamine, terbutaline, and isoproterenol. Analogs and derivatives of such compounds are also intended. For example, U.S. Pat. No. 4,663,351 describes a dobutamine prodrug that can be administered orally. One of ordinary skill in the art would be able to determine if a compound is capable of causing positive inotropic effects and also additional beta-agonist compounds. In particular embodiments, the beta-receptor agonist is selective for the beta-1 receptor. In other embodiments the beta-agonist is selective for the beta-2 receptor, or is not selective for any particular receptor.

Diseases or conditions that are "responsive to nitroxyl therapy" includes any disease or condition in which administration of a compound that donates an effective amount of nitroxyl under physiological conditions treats and/or prevents the disease or condition, as those terms are defined herein. A disease or condition whose symptoms are suppressed or diminished upon administration of nitroxyl donor is a disease or condition responsive to nitroxyl therapy. Non-limiting examples of diseases or conditions that are responsive to nitroxyl therapy include coronary obstructions, coronary artery disease (CAD), angina, heart attack, myocardial infarction, high blood pressure, ischemic cardiomyopathy and infarction, diastolic heart failure, pulmonary congestion, pulmonary edema, cardiac fibrosis, valvular heart disease, pericardial disease, circulatory congestive states, peripheral edema, ascites, Chagas' disease, ventricular hypertrophy, heart valve disease, heart failure, including but not limited to congestive heart failure such as acute congestive heart failure and acute decompensated heart failure. Other cardiovascular diseases or conditions are also intended, as are diseases or conditions that implicate ischemia/reperfusion injury. Cancer is another example of disease or condition that is responsive to nitroxyl therapy.

"Pulmonary hypertension" or "PH" refers to a condition in which the pulmonary arterial pressure is elevated. The current hemodynamic definition of PH is a mean pulmonary arterial pressure (MPAP) at rest of greater than or equal to 25 mmHg.[1] Examples of PH include, but are not limited to, the conditions listed in the updated classification of PH (Table 1).[2]

[1] Badesch D. et al. Diagnosis and assessment of pulmonary arterial hypertension. *J Am Coll Cardiol* 2009; 54(Suppl.): S55-S66.
[2] Simonneau G. et al. Updated clinical classification of pulmonary hypertension. *J Am Coll Cardiol* 2009; 54(1 Suppl): S43-54.

TABLE 1

Classification of Pulmonary hypertension (PH)

1. Pulmonary artery hypertension (PAH)
　1.1. Idiopathic PAH
　1.2. Heritable
　　1.2.1. BMPR2
　　1.2.2. ALK1, endoglin (with or without hereditary hemorrhagic telangiectasia
　　1.2.3. Unknown
　1.3. Drug- and toxin-induced
　1.4. Associated with:
　　1.4.1. Connective tissue diseases
　　1.4.2. Human immunodeficiency virus (HIV) infection
　　1.4.3. Portal hypertension TABLE 1-continued Classification of Pulmonary hypertension (PH)

1.4.4. Congenital heart diseases
　　1.4.5. Schistosomiasis
　1.5 Persistent pulmonary hypertension of the newborn
　1'. Pulmonary veno-occlusive disease (PVOD) and/or pulmonary capillary hemangiomatosis (PCH)
2. Pulmonary hypertension owing to left heart disease
　2.1. Systolic dysfunction
　2.2. Diastolic dysfunction
　2.3. Valvular disease
3. Pulmonary hypertension owing to lung disease and/or hypoxemia
　3.1. Chronic obstructive pulmonary disease
　3.2. Interstitial lung disease
　3.3. Other pulmonary diseases with mixed restrictive and obstructive pattern
　3.4. Sleep-disordered breathing
　3.5. Alveolar hypoventilation disorders
　3.6. Chronic exposure to high altitude
　3.7. Developmental abnormalities
4. Chronic thromboembolic pulmonary hypertension (CTEPH)
5. Pulmonary hypertension with unclear multifactorial mechanisms
　5.1. Hematologic disorders: myeoloproliferative disorders, splenectomy
　5.2. Systemic disorders: sarcoidosis, pulmonary Langerhans cell histiocytosis: lymphangioleiomyomatosis, neurofibromatosis, vasculitis
　5.3. Metabolic disorders: glycogen storage disease, Gaucher disease, thyroid disorders
　5.4. Others: tumoral obstruction, fibrosing mediastinitis, chronic renal failure on dialysis The disclosed subject matter provides certain N-substituted hydroxylamine derivative compounds, methods of using such compounds, and pharmaceutical compositions and kits comprising such compounds.

N-Substituted Hydroxylamine Derivative Compounds

In some embodiments, the disclosed subject matter provides a compound of formula (I) or (II)

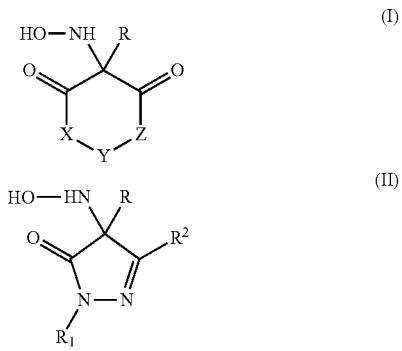

or a pharmaceutically acceptable salt or hydrate thereof, wherein:

X and Z are independently selected from —O—, —NR$^3$—, —S—, —CR$^3$—, and —CR$^3$R$^4$—;

Y is selected from —C(=O)—, —C(=S)—, —C(=NR$^5$)—, and —CR$^5$R$^6$—;

R is $C_1$-$C_8$ alkyl, $C_2$-$C_8$ alkenyl, $C_2$-$C_8$ alkynyl, $C_1$-$C_8$ alkoxy, $C_5$-$C_{10}$ aryl, —C(=O)R$^7$, —C(=S)R$^7$, —C(=NR$^7$)R$^8$, and —C(=NOR$^7$)R$^8$, wherein the alkyl, alkenyl, alkynyl, alkoxy and aryl are unsubstituted or substituted with one or more substituents;

R$^1$ is selected from —H, $C_1$-$C_8$ alkyl, $C_2$-$C_8$ alkenyl, $C_2$-$C_8$ alkynyl, $C_5$-$C_{10}$ aryl, $C_5$-$C_{10}$ heterocycloalkyl, $C_5$-$C_{10}$ heterocycloalkenyl, and $C_5$-$C_{10}$ heteroaryl, wherein the alkyl, alkenyl, alkynyl, aryl, heterocycloalkyl, heterocycloalkenyl and heteroaryl are unsubstituted or substituted with one or more substituents; and $R^2$, $R^3$, $R^4$, $R^5$, $R^6$, $R^7$ and $R^8$ are independently selected from —H, $C_1$-$C_8$ alkyl, $C_2$-$C_8$ alkenyl, $C_2$-$C_8$ alkynyl, $C_5$-$C_{10}$ aryl, $C_5$-$C_{10}$ heterocycloalkyl, $C_5$-$C_{10}$ heterocycloalkenyl, $C_5$-$C_{10}$ heteroaryl, wherein the alkyl, alkenyl, alkynyl, aryl, heterocycloalkyl, heterocycloalkenyl and heteroaryl are unsubstituted or substituted with one or more substituents.

Examples of substituents include, without limitation, halo (fluoro, chloro, bromo or iodo), hydroxyl (—OH), amino (—$NH_2$), cyano (—C≡N), nitro (—$NO_2$), mercapto (—SH), oxo (═O), thioxo (═S), imino (—N-alkyl), alkyl, alkenyl, alkynyl, alkoxy, alkenyloxy, alkynyloxy, aryl, heteroaryl, heterocycloalkyl, heterocycloalkenyl, formyl (—C(═O)H), carbamoyl (—C(═O)$NH_2$), carboxyl (—C(O)OH), ureido (—NH—C(═O)—$NH_2$), thioureido (—NH—C(═S)—$NH_2$), thiocyanato (—SC≡N), sulfonamido (—$SO_2NH_2$), —COR', —C(O)OR', —C(O)NHR', —C(O)NR'R", —NHR', —NR'R", —SR', —SOR', —$SO_2$R', and —OR', wherein R' and R" are independently selected from alkyl, alkenyl, alkynyl, aryl, heteroaryl, heterocycloalkyl and heterocycloalkenyl, and wherein the alkyl, alkenyl, alkynyl, aryl, heteroaryl, heterocycloalkyl and heterocycloalkenyl are unsubstituted or substituted with one or more substituents.

Compounds of Formula (I)

In some embodiments, the disclosed subject matter provides a compound of formula (I)

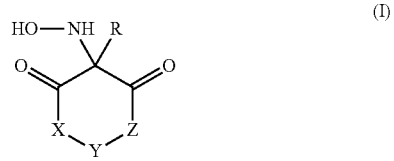

(I)

or a pharmaceutically acceptable salt or hydrate thereof, wherein:

X and Z are independently selected from —O—, —$NR^3$—, —S—, —$CR^3$—, and —$CR^3R^4$—;

Y is selected from —C(═O)—, —C(═S)—, —C(═$NR^5$)—, and —$CR^5R^6$—;

R is $C_1$-$C_5$ alkyl, $C_2$-$C_8$ alkenyl, $C_2$-$C_8$ alkynyl, $C_1$-$C_8$ alkoxy, $C_5$-$C_{10}$ aryl, —C(═O)$R^7$, —C(═S)$R^7$, —C(═$NR^7$)$R^8$, and —C(═$NOR^7$)$R^8$, wherein the alkyl, alkenyl, alkynyl, alkoxy and aryl are unsubstituted or substituted with one or more substituents; and $R^3$, $R^4$, $R^5$, $R^6$, $R^7$ and $R^8$ are independently selected from —H, $C_1$-$C_8$ alkyl, $C_2$-$C_8$ alkenyl, $C_2$-$C_8$ alkynyl, $C_5$-$C_{10}$ aryl, $C_5$-$C_{10}$ heterocycloalkyl, $C_5$-$C_{10}$ heterocycloalkenyl, $C_5$-$C_{10}$ heteroaryl, wherein the alkyl, alkenyl, alkynyl, aryl, heterocycloalkyl, heterocycloalkenyl and heteroaryl are unsubstituted or substituted with one or more substituents.

In some embodiments, at least one of X and Z is —O—. In some embodiments, at least one of X and Z is —$NR^3$—. In some embodiments, at least one of X and Z is —$CR^3$—. In some embodiments, at least one of X and Z is —$CR^3R^4$—.

In some embodiments, X and Z are the same moiety. In some embodiments, X and Z are each —O—. In some embodiments, X and Z are independently —$NR^3$—. In some embodiments, X and Z are each —$NR^3$—; and $R^3$ is —H. In some embodiments, X and Z are independently —$NR^3$—; and $R^3$ is $C_1$-$C_8$ alkyl wherein the alkyl is unsubstituted or substituted with one or more substituents. In some embodiments, X and Z are independently —$NR^3$—; and $R^3$ is $C_1$-$C_8$ alkyl. In some embodiments, X and Z are independently —$NR^3$—; and $R^3$ is methyl. In some embodiments, X and Z are independently —$CR^3$—. In some embodiments, X and Z are each —$CR^3$—; and $R^3$ is —H. In some embodiments, X and Z are independently —$CR^3$—; and $R^3$ is $C_1$-$C_8$ alkyl wherein the alkyl is unsubstituted or substituted with one or more substituents. In some embodiments, X and Z are independently —$CR^3$—; and $R^3$ is $C_1$-$C_8$ alkyl. In some embodiments, X and Z are independently —$CR^3$—; and $R^3$ is $C_5$-$C_{10}$ aryl wherein the aryl is unsubstituted or substituted with one or more substituents. In some embodiments, X and Z are independently —$CR^3$—; and $R^3$ is phenyl or naphthyl wherein the phenyl or naphthyl is unsubstituted or substituted with one or more substituents. In some embodiments, X and Z are independently —$CR^3R^4$—. In some embodiments, X and Z are independently —$CR^3R^4$—; and $R^3$ and $R^4$ are independently selected from —H, $C_1$-$C_8$ alkyl and $C_5$-$C_{10}$ aryl, wherein the alkyl and aryl are unsubstituted or substituted with one or more substituents.

In some embodiments, Y is —C(═O)—. In some embodiments, Y is —C(═S)—. In some embodiments, Y is —C(═$NR^5$)—. In some embodiments, Y is —C(═$NR^5$)—; and $R^5$ is selected from —H and $C_1$-$C_8$ alkyl. In some embodiments, Y is —$CR^5R^6$—. In some embodiments, Y is —$CR^5R^6$—; and $R^5$ and $R^6$ are independently selected from —H and $C_1$-$C_8$ alkyl. In some embodiments, Y is —$CR^5R^6$—; and at least one of $R^5$ and $R^6$ is $C_1$-$C_8$ alkyl. In some embodiments, Y is —$CR^5R^6$—; and $R^5$ and $R^6$ are independently $C_1$-$C_8$ alkyl. In some embodiments, Y is —$CR^5R^6$—; and at least one of $R^5$ and $R^6$ is $C_1$-$C_4$ alkyl. In some embodiments, Y is —$CR^5R^6$—; and $R^5$ and $R^6$ are independently $C_1$-$C_4$ alkyl. In some embodiments, Y is —$CR^3R^4$—; and at least one of $R^3$ and $R^4$ is methyl. In some embodiments, Y is —$CR^3R^4$—; and $R^3$ and $R^4$ are each methyl.

In some embodiments, R is $C_1$-$C_8$ alkyl wherein the alkyl is unsubstituted or substituted with one or more substituents. In some embodiments, R is $C_1$-$C_8$ alkyl. In some embodiments, R is $C_1$-$C_4$ alkyl. In some embodiments, R is methyl or ethyl. In some embodiments, R is methyl. In some embodiments, R is ethyl. In some embodiments, R is trifluoromethyl. In some embodiments, R is $C_1$-$C_8$ alkoxy wherein the alkoxy is unsubstituted or substituted with one or more substituents. In some embodiments, R is $C_5$-$C_{10}$ aryl wherein the aryl is unsubstituted or substituted with one or more substituents. In some embodiments, R is phenyl or naphthyl wherein the phenyl and naphthyl are unsubstituted or substituted with one or more substituents. In some embodiments, R is —C(═O)$R^7$. In some embodiments, R is —C(═O)$R^7$; and $R^7$ is —H. In some embodiments, R is —C(═O)$R^7$; and $R^7$ is $C_1$-$C_8$ alkyl. In some embodiments, R is —C(═S)$R^7$. In some embodiments, R is —C(═S)$R^7$; and $R^7$ is —H. In some embodiments, R is —C(═S)$R^7$; and $R^7$ is $C_1$-$C_8$ alkyl. In some embodiments, R is —C(═$NR^7$)$R^8$. In some embodiments, R is —C(═$NR^7$)$R^8$; and $R^7$ and $R^8$ are independently selected from —H and $C_1$-$C_8$ alkyl. In some embodiments, R is —C(═$NOR^7$)$R^8$. In some embodiments, R is —C(═$NOR^7$)$R^8$; and $R^7$ and $R^8$ are independently selected from —H and $C_1$-$C_8$ alkyl. In some embodiments, R is —C(═$NOR^7$)$R^8$; and $R^7$ and $R^8$ are independently selected from $C_1$-$C_8$ alkyl. In some embodiments, R is —C(═$NOR^7$)$R^8$ and $R^7$ and $R^8$ are independently selected from $C_1$-$C_4$ alkyl. In some embodiments, R is —C(=NOR$^7$)R$^8$ and R$^7$ and R$^8$ are each methyl.

In some embodiments, R is $C_1$-$C_8$ alkyl; and X and Z are each —O—. In some embodiments, R is $C_1$-$C_8$ alkyl; and Y is —CR$^5$R$^6$—. In some embodiments, R is $C_1$-$C_8$ alkyl; X and Z are each —O—; and Y is —CR$^5$R$^6$—. In some embodiments, R is $C_1$-$C_4$ alkyl; X and Z are each —O—; Y is —CR$^5$R$^6$—; and R$^5$ and R$^6$ are independently $C_1$-$C_4$ alkyl. In some embodiments, R is methyl; X and Z are each —O—; Y is —CR$^5$R$^6$—. In some embodiments, R is $C_1$-$C_4$ alkyl; X and Z are each —O—; Y is —CR$^5$R$^6$—; and R$^5$ and R$^6$ are each methyl.

In some embodiments, R is $C_1$-$C_8$ alkyl; and X and Z are independently —NR$^3$—. In some embodiments, R is $C_1$-$C_8$ alkyl; and Y is —C(=O)—. In some embodiments, R is $C_1$-$C_8$ alkyl; X and Z are independently —NR$^3$—; and Y is —C(=O)—. In some embodiments, R is $C_1$-$C_8$ alkyl; X and Z are independently —NR$^3$—; R$^3$ is $C_1$-$C_8$ alkyl; and Y is —C(=O)—. In some embodiments, R is $C_1$-$C_4$ alkyl; X and Z are independently —NR$^3$—; R$^3$ is $C_1$-$C_4$ alkyl; and Y is —C(=O)—. In some embodiments, R is ethyl; X and Z are independently —NR$^3$—; R$^3$ is $C_1$-$C_4$ alkyl; and Y is —C(=O)—. In some embodiments, R is $C_1$-$C_4$ alkyl; X and Z are each —NCH$_3$; and Y is —C(=O)—.

In some embodiments, R is —C(=NOR$^7$)R$^8$; and X and Z are each —O—. In some embodiments, R is —C(=NOR$^7$)R$^8$; and Y is —CR$^5$R$^6$—. In some embodiments, R is —C(=NOR$^7$)R$^8$; X and Z are each —O—; and Y is —CR$^5$R$^6$—. In some embodiments, R is —C(=NOR$^7$)R$^8$; R$^7$ and R$^8$ are independently $C_1$-$C_4$ alkyl; X and Z are each —O—; Y is —CR$^5$R$^6$—; and R$^5$ and R$^6$ are independently $C_1$-$C_4$ alkyl. In some embodiments, R is —C(=NOR$^7$)R$^8$; R$^7$ and R$^8$ are each methyl; X and Z are each —O—; Y is —CR$^5$R$^6$—; and R$^5$ and R$^6$ are independently $C_1$-$C_4$ alkyl. In some embodiments, R is —C(=NOR$^7$)R$^8$; R$^7$ and R$^8$ are independently $C_1$-$C_4$ alkyl; X and Z are each —O—; Y is —CR$^5$R$^6$—; and R$^5$ and R$^6$ are each methyl.

In some embodiments, R is —C(=NOR$^7$)R$^8$; and X and Z are independently —NR$^3$—. In some embodiments, R is —C(=NOR$^7$)R$^8$; and Y is —C(=O)—. In some embodiments, R is —C(=NOR$^7$)R$^8$; X and Z are independently —NR$^3$—; R$^3$ is $C_1$-$C_8$ alkyl; and Y is —C(=O)—. In some embodiments, R is —C(=NOR$^7$)R$^8$; R$^7$ and R$^8$ are independently $C_1$-$C_4$ alkyl; X and Z are independently —NR$^3$—; R$^3$ is $C_1$-$C_4$ alkyl; and Y is —C(=O)—. In some embodiments, R is —C(=NOR$^7$)R$^8$; R$^7$ and R$^8$ are each methyl; X and Z are independently —NR$^3$—; R$^3$ is $C_1$-$C_4$ alkyl; and Y is —C(=O)—. In some embodiments, R is —C(=NOR$^7$)R$^8$; R$^7$ and R$^8$ are independently $C_1$-$C_4$ alkyl; X and Z are each —N(CH$_3$)—; and Y is —C(=O)—.

Representative compounds of formula I include without limitation the compounds listed in Table 2.

TABLE 2

Representative compounds of formula (I)

1

TABLE 2-continued

Representative compounds of formula (I)

2

3

4

In some embodiments, the compound is

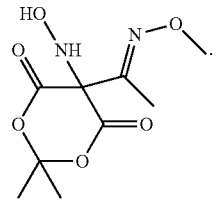 [SMILES: CO/N=C(\C)C1(NO)C(=O)OC(C)(C)OC1=O]

In some embodiments, the compound is

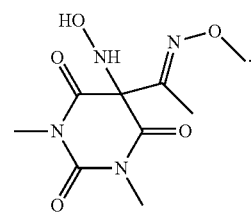

Compounds of Formula (II)

In some embodiments, the disclosed subject matter provides a compound of formula (II)

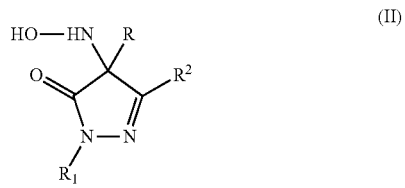

or a pharmaceutically acceptable salt or hydrate thereof, wherein:

R is $C_1$-$C_8$ alkyl, $C_2$-$C_8$ alkenyl, $C_2$-$C_8$ alkynyl, $C_1$-$C_8$ alkoxy, $C_5$-$C_{10}$ aryl, —C(=O)$R^7$, —C(=S)$R^7$, —C(=N$R^7$)$R^8$, and —C(=NO$R^7$)$R^8$, wherein the alkyl, alkenyl, alkynyl, alkoxy and aryl are unsubstituted or substituted with one or more substituents;

$R^1$ is selected from —H, $C_1$-$C_8$ alkyl, $C_2$-$C_8$ alkenyl, $C_2$-$C_8$ alkynyl, $C_5$-$C_{10}$ aryl, $C_5$-$C_{10}$ heterocycloalkyl, $C_5$-$C_{10}$ heterocycloalkenyl, and $C_5$-$C_{10}$ heteroaryl, wherein the alkyl, alkenyl, alkynyl, aryl, heterocycloalkyl, heterocycloalkenyl and heteroaryl are unsubstituted or substituted with one or more substituents; and $R^2$, $R^7$ and $R^8$ are independently selected from —H, $C_1$-$C_8$ alkyl, $C_2$-$C_8$ alkenyl, $C_2$-$C_8$ alkynyl, $C_5$-$C_{10}$ aryl, $C_5$-$C_{10}$ heterocycloalkyl, $C_5$-$C_{10}$ heterocycloalkenyl, $C_5$-$C_{10}$ heteroaryl, wherein the alkyl, alkenyl, alkynyl, aryl, heterocycloalkyl, heterocycloalkenyl and heteroaryl are unsubstituted or substituted with one or more substituents.

In some embodiments, R is $C_1$-$C_8$ alkyl wherein the alkyl is unsubstituted or substituted with one or more substituents. In some embodiments, R is $C_1$-$C_8$ alkyl. In some embodiments, R is $C_1$-$C_4$ alkyl. In some embodiments, R is methyl. In some embodiments, R is trifluoromethyl. In some embodiments, R is $C_1$-$C_8$ alkoxy wherein the alkoxy is unsubstituted or substituted with one or more substituents. In some embodiments, R is $C_5$-$C_{10}$ aryl wherein the aryl is unsubstituted or substituted with one or more substituents. In some embodiments, R is phenyl or naphthyl wherein the phenyl and naphthyl are unsubstituted or substituted with one or more substituents. In some embodiments, R is phenyl wherein the phenyl is unsubstituted or substituted with one or more substituents independently selected from fluoro, chloro, bromo and iodo. In some embodiments, R is phenyl wherein the phenyl is unsubstituted or substituted with fluoro, chloro, bromo or iodo.

In some embodiments, R is phenyl. In some embodiments, R is phenyl substituted with chloro. In some embodiments, R is o-chlorophenyl. In some embodiments, R is m-chlorophenyl. In some embodiments, R is p-chlorophenyl. In some embodiments, R is —C(=O)$R^7$. In some embodiments, R is —C(=O)$R^7$; and $R^7$ is —H. In some embodiments, R is —C(=O)$R^7$; and $R^7$ is $C_1$-$C_8$ alkyl. In some embodiments, R is —C(=S)$R^7$. In some embodiments, R is —C(=S)$R^7$; and $R^7$ is —H. In some embodiments, R is —C(=S)$R^7$; and $R^7$ is $C_1$-$C_8$ alkyl. In some embodiments, R is —C(=N$R^7$)$R^8$. In some embodiments, R is —C(=N$R^7$)$R^8$; and $R^7$ and $R^8$ are independently selected from —H and $C_1$-$C_8$ alkyl. In some embodiments, R is —C(=NO$R^7$)$R^8$. In some embodiments, R is —C(=NO$R^7$)$R^8$; and $R^7$ and $R^8$ are independently selected from —H and $C_1$-$C_8$ alkyl wherein the alkyl is unsubstituted or substituted with one or more substituents. In some embodiments, R is —C(=NO$R^7$)$R^8$; and at least one of $R^7$ and $R^8$ is $C_1$-$C_4$ alkyl. In some embodiments, R is —C(=NO$R^7$)$R^8$; and $R^7$ and $R^8$ are independently selected from $C_1$-$C_8$ alkyl. In some embodiments, R is —C(=NO$R^7$)$R^8$; and $R^7$ and $R^8$ are independently selected from $C_1$-$C_4$ alkyl. In some embodiments, R is —C(=NO$R^7$)$R^8$; and at least one of $R^7$ and $R^8$ is methyl. In some embodiments, R is —C(=NO$R^7$)$R^8$; and $R^7$ and $R^8$ are each methyl. In some embodiments, R is $C_2$-$C_8$ alkenyl wherein the alkenyl is unsubstituted or substituted with one or more substituents. In some embodiments, R is $C_2$-$C_8$ alkynyl wherein the alkynyl is unsubstituted or substituted with one or more substituents. In some embodiments, R is $C_1$-$C_8$ alkoxy wherein the alkoxy is unsubstituted or substituted with one or more substituents. In some embodiments, R is $C_5$-$C_{10}$ aryl wherein the aryl is unsubstituted or substituted with one or more substituents. In some embodiments, R is phenyl or naphthyl wherein the phenyl and naphthyl are unsubstituted or substituted with one or more substituents. In some embodiments, R is —C(=O)$R^7$. In some embodiments, R is —C(=S)$R^7$. In some embodiments, R is —C(=N$R^7$)$R^8$. In some embodiments, R is —C(=O)$R^7$, —C(=S)$R^7$ or —C(=N$R^7$)$R^8$, wherein $R^7$ and $R^8$ are independently selected from —H and $C_1$-$C_8$ alkyl.

In some embodiments, $R^1$ is —H. In some embodiments, $R^1$ is $C_1$-$C_8$ alkyl, wherein the alkyl is unsubstituted or substituted with one or more substituents. In some embodiments, $R^1$ is $C_1$-$C_8$ alkyl wherein the alkyl is unsubstituted or substituted with one or more substituents independently selected from fluoro, chloro, bromo and iodo. In some embodiments, $R^1$ is $C_1$-$C_8$ alkyl. In some embodiments, $R^1$ is $C_1$-$C_4$ alkyl. In some embodiments, $R^1$ is methyl. In some embodiments, $R^1$ is $C_2$-$C_8$ alkenyl wherein the alkenyl is unsubstituted or substituted with one or more substituents. In some embodiments, $R^1$ is $C_2$-$C_8$ alkynyl wherein the alkynyl is unsubstituted or substituted with one or more substituents. In some embodiments, $R^1$ is $C_5$-$C_{10}$ aryl, wherein the aryl is unsubstituted or substituted with one or more substituents. In some embodiments, $R^1$ is $C_5$-$C_{10}$ aryl, wherein the aryl is unsubstituted or substituted with one or more substituents independently selected from fluoro, chloro, bromo and iodo. In some embodiments, $R^1$ is phenyl wherein the phenyl is unsubstituted or substituted with one or more substituents independently selected from fluoro, chloro, bromo and iodo. In some embodiments, $R^1$ is phenyl. In some embodiments, $R^1$ is phenyl substituted with one or more substituents independently selected from fluoro, chloro, bromo and iodo. In some embodiments, $R^1$ is phenyl substituted with chloro. In some embodiments, $R^1$ is $C_5$-$C_{10}$ heterocycloalkyl wherein the heterocycloalkyl is unsubstituted or substituted with one or more substituents. In some embodiments, $R^1$ is $C_5$-$C_{10}$ heterocycloalkenyl wherein the heterocycloalkenyl is unsubstituted or substituted with one or more substituents. In some embodiments, $R^1$ is $C_5$-$C_{10}$ heteroaryl wherein the heteroaryl is unsubstituted or substituted with one or more substituents. In some embodiments, $R^1$ is pyridinyl wherein the pyridinyl is unsubstituted or substituted with one or more substituents. In some embodiments, $R^1$ is pyridinyl.

In some embodiments, $R^2$ is —H. In some embodiments, $R^2$ is $C_1$-$C_8$ alkyl wherein the alkyl is unsubstituted or substituted with one or more substituents. In some embodiments, $R^2$ is $C_1$-$C_8$ alkyl. In some embodiments, $R^2$ is $C_1$-$C_4$ alkyl. In some embodiments, $R^2$ is methyl. In some embodiments, $R^2$ is $C_2$-$C_8$ alkenyl wherein the alkenyl is unsubstituted or substituted with one or more substituents. In some embodiments, $R^2$ is $C_2$-$C_8$ alkynyl wherein the alkynyl is unsubstituted or substituted with one or more substituents. In some embodiments, $R^2$ is $C_5$-$C_{10}$ aryl wherein the aryl unsubstituted or substituted with one or more substituents. In some embodiments, $R^2$ is $C_5$-$C_{10}$ heterocycloalkyl wherein the heterocycloalkyl is unsubstituted or substituted with one or more substituents. In some embodiments, $R^2$ is $C_5$-$C_{10}$ heterocycloalkenyl wherein the heterocycloalkenyl is unsubstituted or substituted with one or more substituents. In some embodiments, $R^2$ is $C_5$-$C_{10}$ heteroaryl wherein the heteroaryl is unsubstituted or substituted with one or more substituents.

In some embodiments, R is $C_1$-$C_8$ alkyl wherein the alkyl is unsubstituted or substituted with one or more substituents; and $R^1$ is —H. In some embodiments, R is $C_1$-$C_8$ alkyl; and $R^1$ is —H. In some embodiments, R is $C_1$-$C_4$ alkyl; and $R^1$ is —H. In some embodiments, R is methyl; and $R^1$ is —H.

In some embodiments, R and $R^1$ are independently $C_1$-$C_8$ alkyl, wherein the alkyl is unsubstituted or substituted with one or more substituents. In some embodiments, R and $R^1$ are independently $C_1$-$C_8$ alkyl. In some embodiments, R and $R^1$ are independently $C_1$-$C_4$ alkyl. In some embodiments, R is $C_1$-$C_4$ alkyl; and $R^1$ is methyl. In some embodiments, R is methyl; and $R^1$ is $C_1$-$C_4$ alkyl. In some embodiments, R and $R^1$ are each methyl.

In some embodiments, R is $C_1$-$C_8$ alkyl; and $R^1$ is $C_5$-$C_{10}$ aryl, wherein the alkyl and aryl are independently unsubstituted or substituted with one or more substituents. In some embodiments, R is $C_1$-$C_8$ alkyl; and $R^1$ is $C_5$-$C_{10}$ aryl wherein the aryl is unsubstituted or substituted with one or more substituents independently selected from fluoro, chloro, bromo and iodo. In some embodiments, R is $C_1$-$C_8$ alkyl; and $R^1$ is phenyl wherein the phenyl is unsubstituted or substituted with one or more substituents independently selected from fluoro, chloro, bromo and iodo. In some embodiments, R is $C_1$-$C_8$ alkyl; and $R^1$ is phenyl wherein the phenyl is unsubstituted or substituted with chloro. In some embodiments, R is methyl; and $R^1$ is phenyl wherein the phenyl is unsubstituted or substituted with chloro. In some embodiments, R is $C_1$-$C_4$ alkyl; and $R^1$ is phenyl. In some embodiments, R is methyl; and $R^1$ is phenyl. In some embodiments, R is $C_1$-$C_4$ alkyl; and $R^1$ is o-chlorophenyl, m-chlorophenyl or p-chlorophenyl. In some embodiments, R is methyl; and $R^1$ is o-chlorophenyl, m-chlorophenyl or p-chlorophenyl. In some embodiments, R is methyl and $R^1$ is o-chlorophenyl. In some embodiments, R is methyl and $R^1$ is o-chlorophenyl. In some embodiments, R is methyl and $R^1$ is m-chlorophenyl. In some embodiments, R is methyl and $R^1$ is p-chlorophenyl.

In some embodiments, R and $R^2$ are independently $C_1$-$C_8$ alkyl wherein the alkyl is unsubstituted or substituted with one or more substituents; and $R^1$ is —H or $C_1$-$C_8$ alkyl wherein the alkyl is unsubstituted or substituted with one or more substituents. In some embodiments, R and $R^2$ are independently $C_1$-$C_8$ alkyl; and $R^1$ is —H or $C_1$-$C_8$ alkyl. In some embodiments, R and $R^2$ are independently $C_1$-$C_4$ alkyl; and $R^1$ is —H. In some embodiments, R is methyl; $R^1$ is —H; and $R^2$ is $C_1$-$C_4$ alkyl. In some embodiments, R is $C_1$-$C_4$ alkyl; $R^1$ is —H; and $R^2$ is methyl. In some embodiments, R, $R^1$ and $R^2$ are independently $C_1$-$C_8$ alkyl, wherein the alkyl is unsubstituted or substituted with one or more substituents. In some embodiments, R, $R^1$ and $R^2$ are independently $C_1$-$C_8$ alkyl. In some embodiments, R, $R^1$ and $R^2$ are independently $C_1$-$C_4$ alkyl. In some embodiments, R, $R^1$ and $R^2$ are independently $C_1$-$C_4$ alkyl; and at least one of R, $R^1$ and $R^2$ is methyl. In some embodiments, R and $R^1$ are independently $C_1$-$C_4$ alkyl; and $R^2$ is methyl. In some embodiments, R is $C_1$-$C_4$ alkyl; and $R^1$ and $R^2$ are each methyl. In some embodiments, R, $R^1$ and $R^2$ are each methyl.

In some embodiments, R and $R^2$ are independently $C_1$-$C_8$ alkyl wherein the alkyl is unsubstituted or substituted with one or more substituents; and $R^1$ is $C_5$-$C_{10}$ aryl wherein the aryl is unsubstituted or substituted with one or more substituents. In some embodiments, R and $R^2$ are independently $C_1$-$C_8$ alkyl; and $R^1$ is $C_5$-$C_{10}$ aryl wherein the aryl is unsubstituted or substituted with one or more substituents. In some embodiments, R and $R^2$ are independently $C_1$-$C_8$ alkyl; and $R^1$ is phenyl wherein the phenyl is unsubstituted or substituted with one or more substituents. In some embodiments, R and $R^2$ are independently $C_1$-$C_8$ alkyl; and $R^1$ is phenyl wherein the phenyl is unsubstituted or substituted with one or more substituents independently selected from fluoro, chloro, bromo and iodo. In some embodiments, R and $R^2$ are independently $C_1$-$C_8$ alkyl; and $R^1$ is phenyl wherein the phenyl is unsubstituted or substituted with fluoro, chloro, bromo or iodo. In some embodiments, R and $R^2$ are independently $C_1$-$C_4$ alkyl; and $R^1$ is phenyl wherein the phenyl is unsubstituted or substituted with chloro. In some embodiments, R and $R^2$ are each methyl; and $R^1$ is phenyl wherein the phenyl is unsubstituted or substituted with chloro. In some embodiments, R is $C_1$-$C_4$ alkyl; and $R^1$ is phenyl. In some embodiments, R and $R^2$ are each methyl; and $R^1$ is phenyl. In some embodiments, R and $R^2$ are independently $C_1$-$C_4$ alkyl; and $R^1$ is o-chlorophenyl, m-chlorophenyl or p-chlorophenyl. In some embodiments, R and $R^2$ are each methyl; and $R^1$ is o-chlorophenyl, m-chlorophenyl or p-chlorophenyl. In some embodiments, R and $R^2$ are each methyl and $R^1$ is o-chlorophenyl. In some embodiments, R and $R^2$ are each methyl and $R^1$ is o-chlorophenyl. In some embodiments, R and $R^2$ are each methyl and $R^1$ is m-chlorophenyl. In some embodiments, R and $R^2$ are each methyl and $R^1$ is p-chlorophenyl.

In some embodiments, R is —C(=NOR$^5$)R$^6$; and $R^1$ and $R^2$ are independently $C_1$-$C_8$ alkyl wherein the alkyl is unsubstituted or substituted with one or more substituents. In some embodiments, R is —C(=NOR$^5$)R$^6$; and $R^1$ and $R^2$ are independently $C_1$-$C_8$ alkyl. In some embodiments, R is —C(=NOR$^5$)R$^6$; $R^1$, $R^2$, $R^5$ and $R^6$ are independently $C_1$-$C_8$ alkyl. In some embodiments, R is —C(=NOR$^5$)R$^6$; and $R^1$, $R^2$, $R^5$ and $R^6$ are independently $C_1$-$C_4$ alkyl. In some embodiments, R is —C(=NOR$^5$)R$^6$; $R^5$ and $R^6$ are independently $C_1$-$C_4$ alkyl; and $R^1$ and $R^2$ are each methyl. In some embodiments, R is —C(=NOR$^5$)R$^6$; $R^5$ and $R^6$ are each methyl; and $R^1$ and $R^2$ are independently $C_1$-$C_4$ alkyl. In some embodiments, R is —C(=NOR$^5$)R$^6$; and $R^1$, $R^2$, $R^5$ and $R^6$ are each methyl.

In some embodiments, R is —C(=NOR$^5$)R$^6$; $R^1$ is $C_5$-$C_{10}$ aryl wherein the aryl is unsubstituted or substituted with one or more substituents; and $R^2$ is $C_1$-$C_8$ alkyl wherein the alkyl is unsubstituted or substituted with one or more substituents. In some embodiments, R is —C(=NOR$^5$)R$^6$; $R^5$ and $R^6$ are independently $C_1$-$C_8$ alkyl; $R^1$ is $C_5$-$C_{10}$ aryl; and $R^2$ is $C_1$-$C_8$ alkyl, wherein the alkyl and aryl are unsubstituted or substituted with one or more substituents. In some embodiments, R is —C(=NOR$^5$)R$^6$; $R^2$, $R^5$ and $R^6$ are independently $C_1$-$C_8$ alkyl; and $R^1$ is $C_5$-$C_{10}$ aryl wherein the aryl is unsubstituted or substituted with one or more substituents. In some embodiments, R is —C(=NOR$^5$)R$^6$; $R^2$, $R^5$ and $R^6$ are independently $C_1$-$C_4$ alkyl; and $R^1$ is $C_5$-$C_{10}$ aryl wherein the aryl is unsubstituted or substituted with one or more substituents. In some embodiments, R is —C(=NOR$^5$)R$^6$; $R^2$, $R^5$ and $R^6$ are independently $C_1$-$C_4$ alkyl; and $R^1$ is phenyl wherein the phenyl is unsubstituted or substituted with one or more substituents. In some embodiments, R is —C(=NOR$^5$)R$^6$; $R^2$, $R^5$ and $R^6$ are independently $C_1$-$C_4$ alkyl; and $R^1$ is phenyl wherein the phenyl is unsubstituted or substituted with one or more substituents independently selected from fluoro, chloro, bromo and iodo. In some embodiments, R is —C(=NOR$^5$)R$^6$; $R^2$, $R^5$ and $R^6$ are each methyl; and $R^1$ is phenyl wherein the phenyl is unsubstituted or substituted with one or more substituents independently selected from fluoro, chloro, bromo and iodo. In some embodiments, R is —C(=NOR$^5$)R$^6$; $R^2$, $R^5$ and $R^6$ are each methyl; and $R^1$ is phenyl wherein the phenyl is unsubstituted or substituted with fluoro, chloro, bromo or iodo. In some embodiments, R is —C(=NOR$^5$)R$^6$; $R^2$, $R^5$ and $R^6$ are each methyl; and $R^1$ is phenyl or chlorophenyl. In some embodiments, R is —C(=NOR$^5$)R$^6$; $R^2$, $R^5$ and $R^6$ are independently $C_1$-$C_4$ alkyl; and $R^1$ is phenyl. In some embodiments, R is —C(=NOR$^5$)R$^6$; $R^2$, $R^5$ and $R^6$ are independently $C_1$-$C_4$ alkyl; and $R^1$ is o-chlorophenyl, m-chlorophenyl or p-chlorophenyl.

Representative compounds of formula II include without limitation the compounds listed in Table 3.

TABLE 3

Representative compounds of formula II

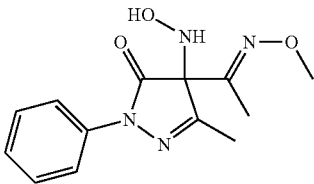 [SMILES: CO/N=C(\C)C1(NO)C(=O)N(c2ccccc2)N=C1C]
6

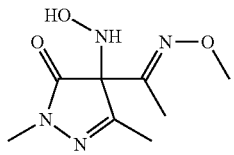
7

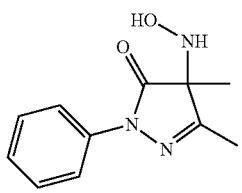 [SMILES: CC1=NN(c2ccccc2)C(=O)C1(C)NO]
8

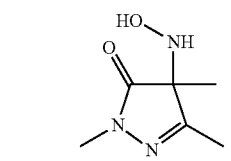
9

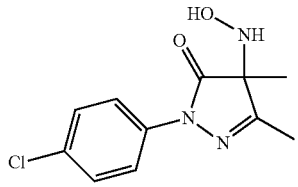 [SMILES: CC1=NN(c2ccc(Cl)cc2)C(=O)C1(C)NO]
10

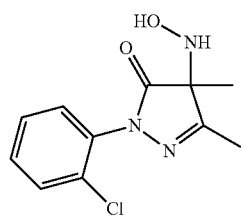 [SMILES: CC1=NN(c2ccccc2Cl)C(=O)C1(C)NO]
11

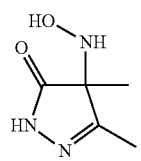
12

In some embodiments, the compound is

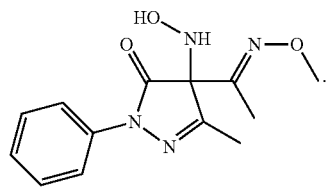 [SMILES: CO/N=C(\C)C1(NO)C(=O)N(c2ccccc2)N=C1C]

In some embodiments, the compound is one that donates nitroxyl under physiological conditions, such as at a pH of 7.4 and/or at a temperature of 37° C. In some embodiments, the compound is one that donates 40% or more of its theoretical maximum amount of nitroxyl under physiological conditions. In some embodiments, the compound is one that donates 50% or more of the theoretical maximum amount of nitroxyl under physiological conditions. In some embodiments, the compound is one that donates 60% or more of the theoretical maximum amount of nitroxyl under physiological conditions. In some embodiments, the compound is one that donates 70% or more of the theoretical maximum amount of nitroxyl under physiological conditions. In some embodiments, the compound is one that donates 80% or more of the theoretical maximum amount of nitroxyl under physiological conditions. In some embodiments, the compound is one that donates 90% or more of the theoretical maximum amount of nitroxyl under physiological conditions.

For all compounds disclosed herein, where applicable due to the presence of a stereocenter, the compound is intended to embrace all possible stereoisomers of the compound depicted or described. Compositions comprising a compound with at least one stereocenter are also embraced by the disclosed subject matter, and include racemic mixtures or mixtures containing an enantiomeric excess of one enantiomer or single diastereomers or diastereomeric mixtures. All such isomeric forms of these compounds are expressly included herein the same as if each and every isomeric form were specifically and individually listed. The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are also expressly included in the disclosed subject matter. The compounds herein may also be represented in multiple tautomeric forms, and in such instances, the disclosed subject matter expressly includes all tautomeric forms of the compounds described herein, even though only a single tautomeric form may be represented.

In some embodiments, the disclosed subject matter provides a substantially pure compound. "Substantially pure" intends a preparation of the compound that contains no more than 25% of impurity (e.g. by weight %), which impurity maybe another compound altogether or a different form of the compound (e.g. a different salt or isomer). Percent purity may be assessed by methods known in the art. In some embodiments, a preparation of substantially pure compound is provided where the preparation contains no more than 15% of impurity. In some embodiments, a preparation of substantially pure compound is provided where the preparation contains no more than 10% impurity. In some embodiments, a preparation of substantially pure compound is provided where the preparation contains no more than 5% impurity. In some embodiments, a preparation of substantially pure compound is provided where the preparation contains no more than 3% impurity. In some embodiments, a preparation of substantially pure compound is provided where the preparation contains no more than 1% impurity.

In some embodiments, the disclosed subject matter provides a compound in purified and/or isolated form, for example following column chromatography, high-pressure liquid chromatography, recrystallization, or other purification techniques. Where particular stereoisomers of compounds of the disclosed subject matter are denoted, such stereoisomers may be substantially free of other stereoisomers.

Pharmaceutical Compositions

In some embodiments, the disclosed subject matter provides a pharmaceutical composition comprising an effective amount of a compound described herein or a pharmaceutically acceptable salt thereof, together with a pharmaceutically acceptable excipient.

Examples of pharmaceutically acceptable excipients include those described above, such as carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of pharmaceutically acceptable excipients are taught in "Remington: The Science and Practice of Pharmacy", 21st Ed. (Lippincott Williams & Wilkins 2005), the disclosure of which is incorporated herein by reference.

The pharmaceutical compositions may be formulated for administration in solid or liquid form, including those adapted for the following: (1) oral administration, for example, drenches (for example, aqueous or non-aqueous solutions or suspensions), tablets (for example, those targeted for buccal, sublingual and systemic absorption), caplets, boluses, powders, granules, pastes for application to the tongue, hard gelatin capsules, soft gelatin capsules, mouth sprays, troches, lozenges, pellets, syrups, suspensions, elixirs, liquids, emulsions and microemulsions; (2) parenteral administration, for example, by subcutaneous, intramuscular, intravenous or epidural injection as, for example, a sterile solution or suspension; (3) topical application, for example, as a cream, ointment, patch, pad or spray applied to the skin; (4) intravaginally or intrarectally, for example, as a pessary, cream or foam; (5) sublingually; (6) ocularly; (7) transdermally; or (8) nasally. The pharmaceutical compositions may be for immediate, sustained or controlled release.

In some embodiments, the pharmaceutical compositions are formulated for oral administration. In some embodiments, the pharmaceutical compositions are formulated for intravenous administration.

The compounds and pharmaceutical compositions described herein may be prepared as any appropriate unit dosage form, such as capsules, sachets, tablets; powder, granules, solution, suspension in an aqueous liquid or a non-aqueous liquid, oil-in-water liquid emulsion, water-in-oil liquid emulsion, liposomes and bolus.

Tablets may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets may be optionally coated or scored and may be formulated so as to provide slow or controlled release of the active ingredient therein. Methods of formulating such slow or controlled release compositions of pharmaceutically active ingredients, such as those herein and other compounds known in the art, are known in the art and described in several issued US patents, some of which include, but are not limited to, U.S. Pat. Nos. 4,369,174 and 4,842,866, and references cited therein. Coatings can be used for delivery of compounds to the intestine (see, e.g. U.S. Pat. Nos. 6,638,534, 5,217,720 and 6,569,457, and references cited therein). A skilled artisan will recognize that in addition to tablets, other dosage forms can be formulated to provide slow or controlled release of the active ingredient. Such dosage forms include, but are not limited to, capsules, granulations and gel-caps.

Pharmaceutical compositions suitable for topical administration include, without limitation, lozenges comprising the ingredients in a flavored basis, such as sucrose, acacia and tragacanth; and pastilles comprising the active ingredient in a flavored basis or in an inert basis, such as gelatin and glycerin.

Pharmaceutical compositions suitable for parenteral administration include, without limitation, aqueous and non-aqueous sterile injection solutions containing, for example, anti-oxidants, buffers, bacterio stats and solutes that render the formulation isotonic with the blood of the intended recipient; and aqueous and non-aqueous sterile suspensions containing, for example, suspending agents and thickening agents. The formulations may be presented in unit-dose or multi-dose containers, for example, sealed ampules and vials, and may be stored in a freeze dried (lyophilized) condition requiring only the addition of a sterile liquid carrier, such as water, immediately prior to use. In some embodiments, the aqueous composition is acidic, having a pH of about 5.5 to about 7.

Extemporaneous injection solutions and suspensions may be prepared from sterile powders, granules and tablets.

Methods of Using the Compounds and Pharmaceutical Compositions

In some embodiments, the disclosed subject matter provides a method of modulating (such as increasing or reducing) in vivo nitroxyl levels, comprising administering to an individual in need thereof a compound or pharmaceutical composition as described herein. In some embodiments, the individual has, is suspected of having, or is at risk of having or developing a disease or condition that is responsive to nitroxyl therapy.

In some embodiments, the disclosed subject matter provides a method of treating, preventing or delaying the onset and/or development of a disease or condition, comprising administering to an individual (including an individual identified as in need of such treatment, prevention or delay) an effective amount of a compound or pharmaceutical composition as described herein. Identifying an individual in need thereof can be in the judgment of a physician, clinical staff, emergency response personnel or other health care professional and can be subjective (e.g. opinion) or objective (e.g. measurable by a test or diagnostic method).

Particular diseases or conditions embraced by the methods described herein include, without limitation, cardiovascular diseases, ischemia, reperfusion injury, cancerous diseases, pulmonary hypertension and conditions responsive to nitroxyl therapy.

Cardiovascular Diseases

In some embodiments, the disclosed subject matter provides a method of treating a cardiovascular disease, comprising administering an effective amount of a compound or pharmaceutical composition as described herein to an individual in need thereof.

Examples of cardiovascular diseases include, without limitation, cardiovascular diseases that are responsive to nitroxyl therapy, coronary obstructions, coronary artery disease (CAD), angina, heart attack, myocardial infarction, high blood pressure, ischemic cardiomyopathy and infarction, pulmonary congestion, pulmonary edema, cardiac fibrosis, valvular heart disease, pericardial disease, circulatory congestive states, peripheral edema, ascites, Chagas' disease, ventricular hypertrophy, heart valve disease, heart failure, diastolic heart failure, congestive heart failure, acute congestive heart failure, acute decompensated heart failure, and cardiac hypertrophy.

In some embodiments, the individual is experiencing heart failure. In some embodiments, the individual is experiencing heart failure and/or undergoing treatment with a positive inotrope. In some embodiments, the individual is experiencing heart failure and/or undergoing treatment with a beta-andrenergic receptor antagonist (also referred to herein as beta-antagonist or beta-blocker). A beta-antagonist includes any compound that effectively acts as an antagonist at an individual's beta-adrenergic receptors, and provides desired therapeutic or pharmaceutical results, such as diminished vascular tone and/or heart rate. An individual that is undergoing treatment with a beta-antagonist is any individual to whom a beta-antagonist has been administered, and in whom the beta-antagonist continues to act as an antagonist at the individual's beta-adrenergic receptors. Examples of beta-antagonists include, without limitation, propranolol, metoprolol, bisoprolol, bucindolol, and carvedilol.

In some embodiments, the individual is experiencing heart failure and/or undergoing treatment with a beta-adrenergic receptor agonist (also referred to herein as beta-agonist). Examples of beta-agonists include, without limitation, dopamine, dobutamine, isoproterenol, and analogs and derivatives of such compounds.

The determination of whether an individual is undergoing treatment with a positive inotrope, beta-antagonist or beta-agonist may be made by examination of the individual's medical history, or screening of the individual for the presence of such agents by chemical tests, such as high-speed liquid chromatography, as described in Thevis et al., *Biomed. Chromatogr.* 2001, 15, 393-402.

In some embodiments, the method further comprises administering an effective amount of at least one other positive inotrope to the individual. In some embodiments, the method further comprises administering an effective amount of a beta-antagonist to the individual. In some embodiments, the method further comprises administering an effective amount of a beta-agonist to the individual.

In some embodiments, the cardiovascular disease is heart failure. The heart failure may be of any type or form, including any of the heart failures described herein. Non-limiting examples of heart failure include early stage heart failure, Class I, II, III or IV heart failure, acute heart failure, congestive heart failure (CHF) and acute congestive heart failure. In some embodiments, the heart failure is acute decompensated heart failure.

In some embodiments, the cardiovascular disease is CHF, and the method further comprises administering an effective amount of at least one other positive inotropic agent to the individual. In some embodiments, the individual is experiencing heart failure. In some embodiments, the at least one other positive inotrope is a beta-adrenergic agonist. In some embodiments, the beta-adrenergic agonist is dobutamine.

Ischemia or Reperfusion Injury

In some embodiments, the disclosed subject matter provides a method of treating, preventing or delaying the onset and/or development of ischemia or reperfusion injury, comprising administering an effective amount of a compound or pharmaceutical composition as described herein to a subject in need thereof.

In some embodiments, the method is for preventing ischemia or reperfusion injury. In some embodiments, the compound or pharmaceutical composition is administered prior to the onset of ischemia. In some embodiments, the pharmaceutical composition is administered prior to procedures in which myocardial ischemia may occur, for example an angioplasty or surgery, such as a coronary artery bypass graft surgery. In some embodiments, the compound or pharmaceutical composition is administered after ischemia but before reperfusion. In some embodiments, the compound or pharmaceutical composition is administered after ischemia and reperfusion.

In some embodiments, the subject is an individual. In some embodiments, the subject is an individual at risk for an ischemic event. In some embodiments, the individual is at risk for a future ischemic event, but has no present evidence of ischemia. The determination of whether an individual is at risk for an ischemic event can be performed by any method known in the art, such as examining the individual or the individual's medical history. In some embodiments, the individual has had a prior ischemic event. Thus, the individual may be at risk of a first or subsequent ischemic event. Examples of individuals at risk for an ischemic event include individuals with known hypercholesterolemia, EKG changes associated with ischemia (e.g., peaked or inverted T-waves or ST segment elevations or depression in an appropriate clinical context), abnormal EKG not associated with active ischemia, elevated CKMB, clinical evidence of ischemia (e.g., crushing sub-sternal chest pain or arm pain, shortness of breath and/or diaphoresis), prior history of myocardial infarction, elevated serum cholesterol, sedentary lifestyle, angiographic evidence of partial coronary artery obstruction, echocardiographic evidence of myocardial damage, or any other evidence of a risk for a future ischemic event. Examples of ischemic events include, without limitation, myocardial infarction (MI) and neurovascular ischemia, such as a cerebrovascular accident CVA).

In some embodiments, the subject is an organ that is to be transplanted. In some embodiments, the compound or pharmaceutical composition is administered prior to reperfusion of the organ in a transplant recipient. In some embodiments, the compound or pharmaceutical composition is administered prior to removal of the organ from the donor, for example through the perfusion cannulas used in the organ removal process. If the organ donor is a live donor, for example a kidney donor, the compound or pharmaceutical composition can be administered to the organ donor. In some embodiments, the compound or pharmaceutical composition is administered by storing the organ in a solution comprising the compound or pharmaceutical composition. For example, the compound or pharmaceutical composition can be included in the organ preservation solution, such as the University of Wisconsin "UW" solution, which is a solution comprising hydroxyethyl starch substantially free of ethylene glycol, ethylene chlorohydrin and acetone (see, U.S. Pat. No. 4,798,824). In some embodiments, the amount of the compound or pharmaceutical composition is such that ischemia or reperfusion injury to the tissues of the organ is reduced upon reperfusion in the recipient of transplanted organ. In some embodiments, the method reduces tissue necrosis (the size of infarct) in at-risk tissues.

Ischemia or reperfusion injury may damage tissues other than those of the myocardium and the disclosed subject matter embraces methods of treating or preventing such damage. In some embodiments, the ischemia or reperfusion injury is non-myocardial. In some embodiments, the method reduces injury from ischemia or reperfusion in the tissue of the brain, liver, gut, kidney, bowel, or any part of the body other than the myocardium. In some embodiments, the individual is at risk for such injury. Selecting a person at risk for non-myocardial ischemia could include a determination of the indicators used to assess risk for myocardial ischemia. However, other factors may indicate a risk for ischemia/reperfusion in other tissues. For example, surgery patients often experience surgery related ischemia. Thus, individuals scheduled for surgery could be considered at risk for an ischemic event. The following risk factors for stroke (or a subset of these risk factors) could demonstrate an individual's risk for ischemia of brain tissue: hypertension, cigarette smoking, carotid artery stenosis, physical inactivity, diabetes mellitus, hyperlipidemia, transient ischemic attack, atrial fibrillation, coronary artery disease, congestive heart failure, past myocardial infarction, left ventricular dysfunction with mural thrombus, and mitral stenosis. Ingall, *Postgrad. Med.* 2000, 107(6), 34-50. Further, complications of untreated infectious diarrhea in the elderly can include myocardial, renal, cerebrovascular and intestinal ischemia. Slotwiner-Nie et al., *Gastroenterol. Clin. N. Am.* 2001, 30(3), 625-635. Alternatively, individuals could be selected based on risk factors for ischemic bowel, kidney or liver disease. For example, treatment would be initiated in elderly individuals at risk of hypotensive episodes (such as surgical blood loss). Thus, individuals presenting with such an indication would be considered at risk for an ischemic event. In some embodiments, the individual has any one or more of the conditions listed herein, such as diabetes mellitus or hypertension. Other conditions that may result in ischemia, such as cerebral arteriovenous malformation, could demonstrate an individual's risk for an ischemic event.

In some embodiments, the method further comprises administering an additional therapeutic agent. The therapeutic agent may be, for example, a nitroxyl-donating compound, such as Angeli's salt or another compound described herein, a beta-blocker, a calcium channel blocker, an anti-platelet agent or any other therapeutic agent for reducing ischemic injury or for protecting myocardium in the individual.

Cancerous Diseases

In some embodiments, the disclosed subject matter provides a method of treating, preventing or delaying the onset and/or development of a cancerous disease, comprising administering an effective amount of a compound or pharmaceutical composition as described herein to an individual in need thereof.

In some embodiments, the individual has or is suspected of having a cancerous disease, e.g. cancer.

Cancers that may be treated by the methods described herein include, without limitation, cancers of the head and neck, which include tumors of the head, neck, nasal cavity, paranasal sinuses, nasopharynx, oral cavity, oropharynx, larynx, hypopharynx, salivary glands, and paragangliomas; cancers of the liver and biliary tree, such as hepatocellular carcinoma; intestinal cancers, such as colorectal cancer; ovarian cancer; small cell and non-small cell lung cancer; breast cancer sarcomas, such as fibrosarcoma, malignant fibrous histiocytoma, embryonal rhabdomysocarcoma, leiomysosarcoma, neurofibrosarcoma, osteosarcoma, synovial sarcoma, liposarcoma, and alveolar soft part sarcoma; neoplasms of the central nervous systems, such as brain cancer; lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma.

In some embodiments, the method further comprises administering an effective amount of an additional therapeutic agent to the individual. In some embodiments, the additional therapeutic agent is an anti-cancer agent or a cytotoxic agent. Examples of such agents include, without limitation, alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, microtubule stabilizers, nucleoside (purine or pyrimidine) analogs, nuclear export inhibitors, proteasome inhibitors, topoisomerase (I or II) inhibitors, tyrosine kinase inhibitors. Specific anti-cancer or cytotoxic agents include, for example, beta.-lapachone, ansamitocin P3, auristatin, bicalutamide, bleomycin, bleomycin, bortezomib, busulfan, calicheamycin, callistatin A, camptothecin, capecitabine, cisplatin, cryptophycins, daunorubicin, docetaxel, doxorubicin, duocarmycin, dynemycin A, etoposide, floxuridine, floxuridine, fludarabine, fluoruracil, gefitinib, gemcitabine, hydroxyurea, imatinib, interferons, interleukins, irinotecan, methotrexate, mitomycin C, oxaliplatin, paclitaxel, spongistatins, suberoylanilide hydroxamic acid (SAHA), thiotepa, topotecan, trichostatin A, vinblastine, vincristine and vindesine.

Pulmonary Hypertension

In some embodiments, the disclosed subject matter provides a method of treating, preventing or delaying the onset and/or development of pulmonary hypertension, comprising administering an effective amount of a compound or pharmaceutical composition as described herein to an individual in need thereof. In some embodiments, the pulmonary hypertension is selected from the diseases and conditions listed above in Table 1. In some embodiments, the pulmonary hypertension is pulmonary arterial hypertension (PAH). In some embodiments, the pulmonary hypertension is pulmonary hypertension owing to left heart disease. In some embodiments, the left heart disease is left heart failure. In some embodiments, the left heart failure is systolic heart failure. In some embodiments, the left heart failure is diastolic heart failure. In some embodiments, the left heart failure is chronic or acutely decompensated. In some embodiments, the pulmonary hypertension is chronic thromboembolic pulmonary hypertension.

In some embodiments, the disclosed subject matter provides a method of reducing mean pulmonary arterial pressure (MPAP), comprising administering an effective amount of a compound or a pharmaceutical composition described herein to an individual in need thereof. In some embodiments, the MPAP is reduced by up to about 50%. In some embodiments, the MPAP is reduced by up to about 25%. In some embodiments, the MPAP is reduced by up to 20%. In some embodiments, the MPAP is reduced by up to 15%. In some embodiments, the MPAP is reduced by up to 10%. In some embodiments, the MPAP is reduced by up to 5%. In some embodiments, the MPAP is reduced to about 12 to 16 mmHg. In some embodiments, the MPAP is reduced to about 15 mmHg.

Administration Modes, Regimens and Dose Levels

Any administration regimen well known to those skilled in the art for regulating the timing and sequence of drug delivery can be used and repeated as necessary to effect treatment in the methods described herein. For example, the compound or pharmaceutical composition may be administered 1, 2, 3 or 4 times daily, by a single dose, multiple discrete doses or continuous infusion.

The compound or pharmaceutical composition may be administered prior to, at substantially the same time with, or after administration of an additional therapeutic agent. The administration regimen may include pretreatment and/or co-administration with the additional therapeutic agent. In such case, the compound or pharmaceutical composition and the additional therapeutic agent may be administered simultaneously, separately, or sequentially.

Examples of administration regimens include without limitation:

administration of each compound, pharmaceutical composition and therapeutic agent in a sequential manner; and co-administration of each compound, pharmaceutical composition and therapeutic agent in a substantially simultaneous manner (e.g., as in a single unit dosage form) or in multiple, separate unit dosage forms for each compound, pharmaceutical composition and therapeutic agent.

Administration of the compound or pharmaceutical composition may be via any accepted mode known to one skilled in the art, for example, orally, parenterally, by inhalation spray, topically, rectally, nasally, buccally, vaginally, intraocularly, intrapulmonarily, or via an implanted reservoir. The term "parenterally" includes without limitation subcutaneously, intravenously, intramuscularly, intraperitoneally, intrathecally, intraventricularly, intrasternally, intracranially, by intraosseous injection and by infusion techniques. Administration may involve systemic exposure or may be local, such as when a compound or pharmaceutical composition is administered at the site of interest. Various tools can be used for administering at the site of interest, such as catheters, trocars, projectiles, pluronic gels, stems, sustained drug release polymers or other devices which provide for internal access. Where the compound or pharmaceutical composition is administered to an organ to be donated, such organ may be bathed in a medium containing the compound or pharmaceutical composition. Alternatively, the compound or pharmaceutical composition may be painted onto the organ, or may be applied in any suitable manner.

It will be appreciated by those skilled in the art that the "effective amount" or "dose level" will depend on various factors such as the particular administration mode, administration regimen, compound, and composition selected, and the particular disease and patient being treated. For example, the appropriate dose level may vary depending upon the activity, rate of excretion and possible toxicity of the specific compound or composition employed; the age, body weight, general health, gender and diet of the patient being treated; the frequency of administration; the other therapeutic agent(s) being co-administered; and the type and severity of the disease.

The compounds and pharmaceutical compositions described herein may be administered at suitable dose level. In some embodiments, the compound or pharmaceutical composition is administered at a dose level of about 0.0001 to 4.0 grams once per day (or multiple doses per day in divided doses) for adults. Thus, in some embodiments, the compound or pharmaceutical composition is administered at a dose level range in which the low end of the range is any amount between 0.1 mg/day and 400 mg/day and the high end of the range is any amount between 1 mg/day and 4000 mg/day (e.g., 5 mg/day and 100 mg/day, 150 mg/day and 500 mg/day). In some embodiments, the compound or pharmaceutical composition is administered at a dose level range in which the low end of the range is any amount between 0.1 mg/kg/day and 90 mg/kg/day and the high end of the range is any amount between 1 mg/kg/day and 100 mg/kg/day (e.g., 0.5 mg/kg/day and 2 mg/kg/day, 5 mg/kg/day and 20 mg/kg/day).

In some embodiments, the compound or pharmaceutical composition is administered at a weight base dose. In some embodiments, the dose level is about 0.001 to about 10,000 mg/kg/d. In some embodiments, the dose level is about 0.01 to about 1,000 mg/kg/d. In some embodiments, the dose level is about 0.01 to about 100 mg/kg/d. In some embodiments, the dose level is about 0.01 to about 10 mg/kg/d. In some embodiments, the dose level is about 0.1 to about 1 mg/kg/d. In some embodiments, the dose level is less than about 1 g/kg/d.

The dose level can be adjusted for intravenous administration. In such case, the compound or pharmaceutical composition can be administered in an amount of between about 0.01 µg/kg/min to about 100 µg/kg/min, about 0.05 µg/kg/min to about 95 µg/kg/min, about 0.1 µg/kg/min to about 90 µg/kg/min, about 1.0 µg/kg/min to about 80 µg/kg/min, about 10.0 µg/kg/min to about 70 µg/kg/min, about 20 µg/kg/min to about 60 µg/kg/min, about 30 g/kg/min to about 50 µg/kg/min, about 0.01 µg/kg/min to about 1.0 µg/kg/min, about 0.01 g/kg/min to about 10 µg/kg/min, about 0.1 µg/kg/min to about 1.0 µg/kg/min, about 0.1 g/kg/min to about 10 µg/kg/min, about 1.0 µg/kg/min to about 5 µg/kg/min, about 70 g/kg/min to about 100 µg/kg/min, about 80 µg/kg/min to about 90 µg/kg/min.

The dosing interval can be adjusted according to the needs of the individual. For longer intervals of administration, extended release or depot formulations can be used.

Kits Comprising the Compounds or Pharmaceutical Compositions

In some embodiments, the disclosed subject matter provides a kit comprising a compound or a pharmaceutical composition described herein.

In some embodiments, the kit further comprises instructions for using the compound or pharmaceutical composition. The instructions may be in any appropriate form, such as written or electronic form. In some embodiments, the instructions may be written instructions. In some embodiments, the instructions are contained in an electronic storage medium (e.g., magnetic diskette or optical disk). In some embodiments, the instructions include information as to the compound or pharmaceutical composition and the manner of administering the compound or pharmaceutical composition to an individual. In some embodiments, the instructions relate to a method of use described herein (e.g., treating, preventing and/or delaying onset and/or development of a disease or condition selected from cardiovascular diseases, ischemia, reperfusion injury, cancerous disease, pulmonary hypertension and conditions responsive to nitroxyl therapy).

In some embodiments, the kit further comprises suitable packaging. Where the kit comprises more than one compound or pharmaceutical composition, the compounds or pharmaceutical compositions may be packaged individually in separate containers, or combined in one container where cross-reactivity and shelf life permit.

Other than in the working examples, or where otherwise indicated, all numbers expressing quantities of ingredients, reaction conditions, and so forth used in the specification and claims are to be understood as being modified by the term "about". Accordingly, unless indicated to the contrary, such numbers are approximations that may vary depending upon the desired properties sought to be obtained by the disclosed subject matter. At the very least, and not as an attempt to limit the application of the doctrine of equivalents to the scope of the claims, each numerical parameter should be construed in light of the number of significant digits and ordinary rounding techniques.

While the numerical ranges and parameters setting forth the broad scope of the disclosed subject matter are approximations, the numerical values set forth in the working examples are reported as precisely as possible. Any numerical value, however, inherently contains certain errors necessarily resulting from the standard deviation found in their respective testing measurements.

EXAMPLES

The following examples are presented for illustrative purposes and should not serve to limit the scope of the disclosed subject matter.

Example 1: Synthesis of Compounds

The compounds described herein can be made according to the general methods described in Schemes 1 to 3 or by procedures known in the art. Starting materials for the reactions may be commercially available or may be prepared by known procedures or obvious modifications thereof. For example, 5-bromo-5-methyl-Meldrum's acid[1] was obtained through bromination of 5-methyl-Meldrum's acid (sodium bicarbonate, bromine, water). 5-Acetyl-Meldrum's acid[2] was obtained through acylation of Meldrum's acid (acetic acid, N,N'-dicyclohexylcarbodiimide, 4-dimethylaminopyridine, dichloromethane). 5-Acetyl-N,N-dimethylbarbituric acid[2,3] was obtained through acylation of N,N-dimethylbarbituric acid (acetyl chloride, pyridine, dichloromethane). 5-Ethyl-barbituric acid[4] was obtained through reduction of 5-acetyl-Meldrum's acid (sodium cyanoborohydride, acetic acid). 4-Acetyl-N-phenyl-5-methyl-pyrazolone[5] was obtained through acylation of N-phenyl-5-methyl-pyrazolone (acetyl chloride, calcium hydroxide, dioxane). N,O-bis(t-butoxycarbonyl)-hydroxylamine[6] was obtained through N,O diBoc protection of hydroxylamine hydrochloride (di-t-butyl dicarbonate, triethylamine, petroleum ether, t-butyl methyl ether, water). All starting materials were of reagent grade and used without further purification.

NMR spectra were obtained on a Bruker Avance 400 MHz FT-NMR spectrometer. All chemical shifts are reported in parts per million (ppm) relative to residual $CHCl_3$ (7.26 ppm for $^1H$, 77.23 ppm for $^{13}C$), residual DMSO (2.50 ppm for $^1H$, 39.52 for $^{13}C$), or residual $H_2O$ (4.8 ppm for $^1H$). High-resolution mass spectra were obtained on a VG Analytical VG70SE magnetic sector mass spectrometer operating in fast atom bombardment (FAB) mode. Ultraviolet-Visible (UV-Vis) absorption spectra were obtained using a Hewlett Packard 8453 diode array spectrometer. Phosphate-buffered saline (PBS) solutions (0.1 M) were prepared with 140 mM NaCl and 3 mM KCl, with 100 μM diethylenetriaminepentaacetic acid (DTPA), adjusted to pH 7.4. Buffered solutions (0.1 M) for UV-Vis experiments were prepared from HCl/NaCl (pH 1.7), AcOH/AcONa (pH 3.0, 3.5, 4.0, 4.5, 5.0, 5.5), or $NaPO_3H_2/Na_2PO_3H$ (pH 6.0, 6.5, 7.0, 8.0, 9.0, 9.5, 9.8, 10.0, 10.5, 10.6).

Scheme 1. Synthesis of Meldrum's acid donors 1a and 2a

General Scheme:

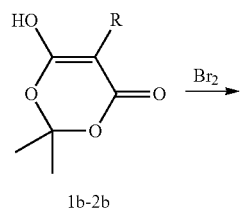

1b-2b

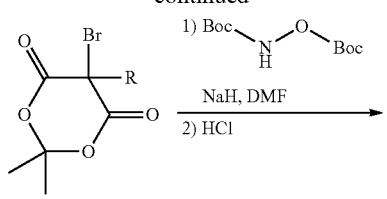

1 R = Me
2 R = C(=N—OMe)CH₃

Specific Examples:

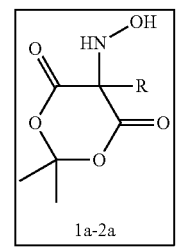

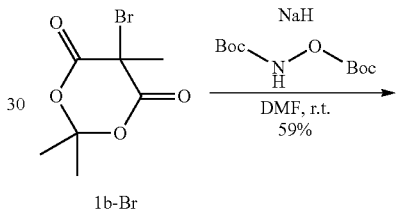

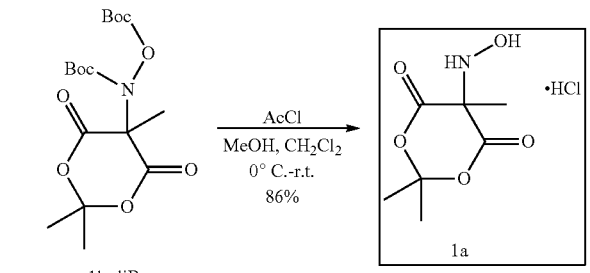

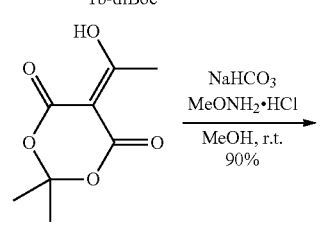

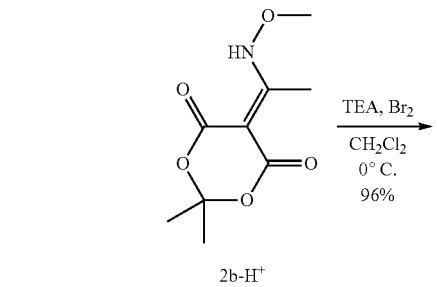

2b-H⁺

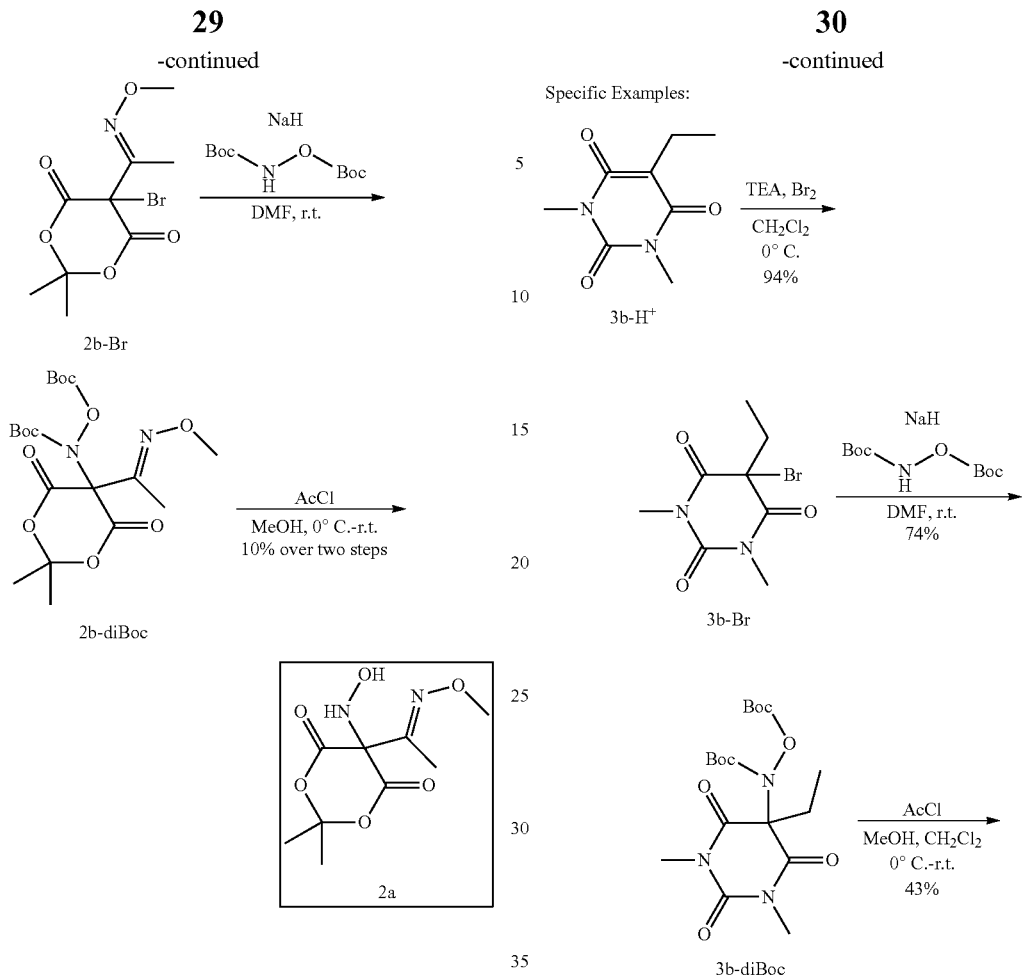
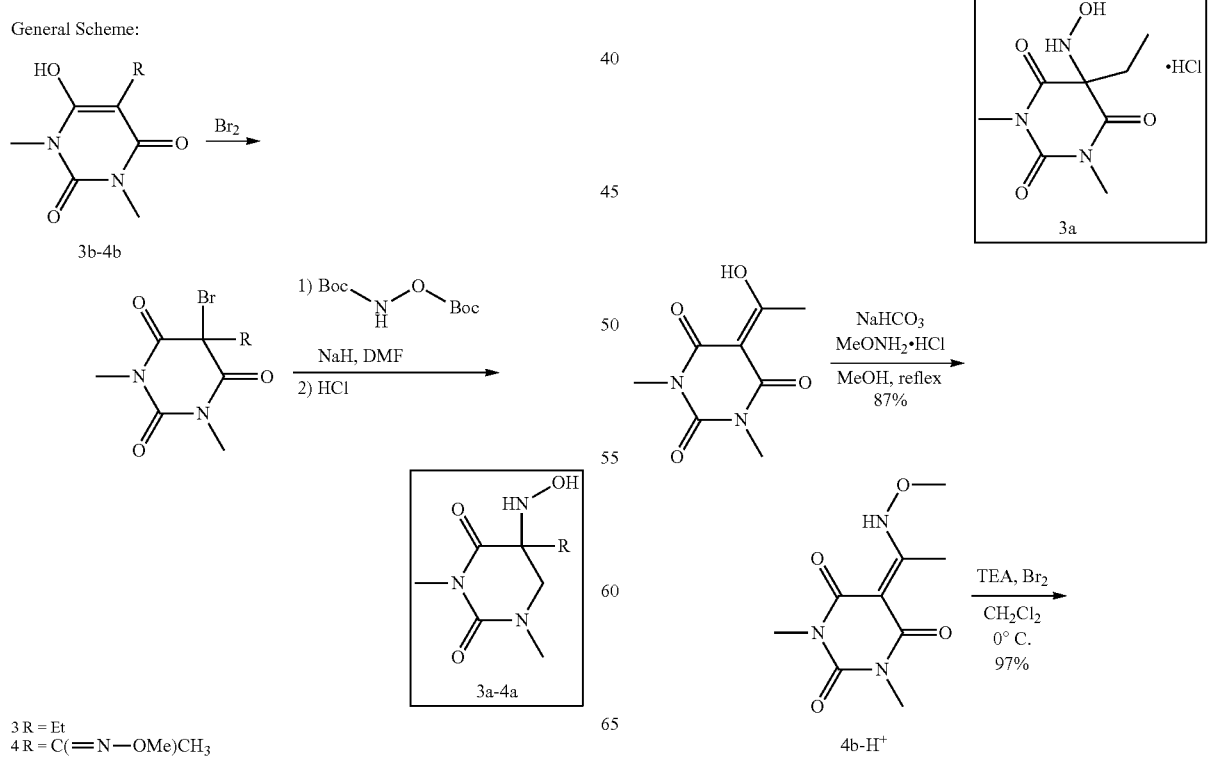

-continued

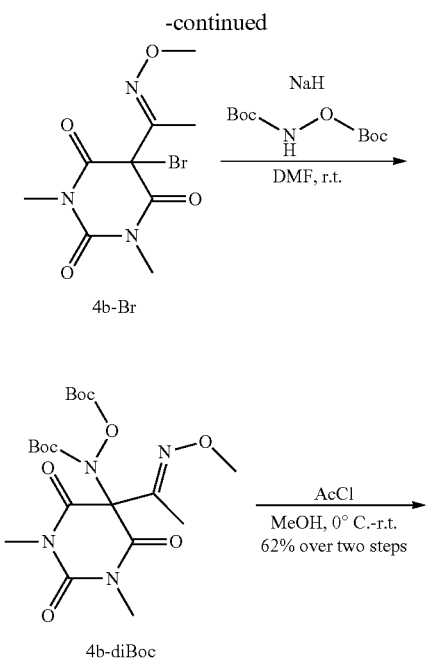

4b-Br 4b-diBoc

4a

Scheme 3. Synthesis of pyrazolone donors 6a-12a

General Scheme: Method A

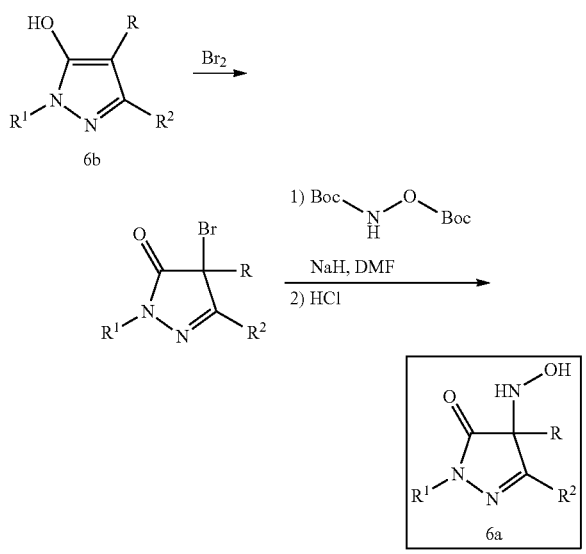

6 R¹ = Ph, R² = Me, R = C(=N—OMe)CH₃

-continued

Specific Example:

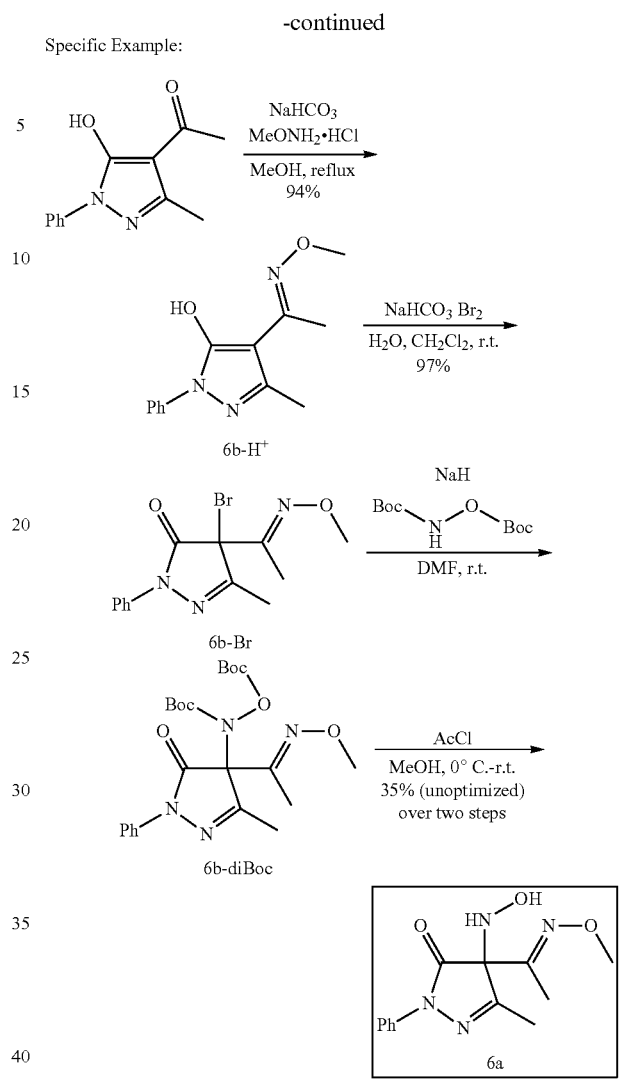

6b-H⁺

6b-Br 6b-diBoc

6a

General Scheme: Method B

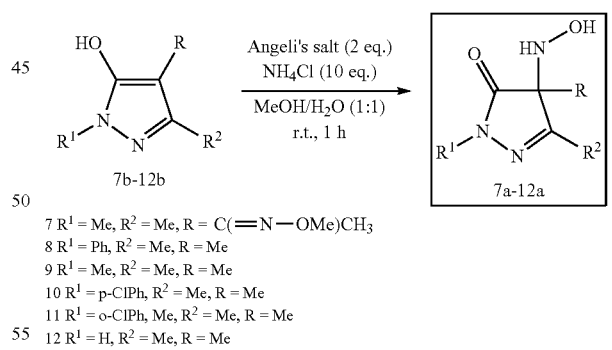

7b-12b → 7a-12a

7 R¹ = Me, R² = Me, R = C(=N—OMe)CH₃
8 R¹ = Ph, R² = Me, R = Me
9 R¹ = Me, R² = Me, R = Me
10 R¹ = p-ClPh, R² = Me, R = Me
11 R¹ = o-ClPh, R² = Me, R = Me
12 R¹ = H, R² = Me, R = Me

General Procedure for Compounds 1a-6a

Bromides of 1b-4b, 6b.

Compound 1b was commercially available and 2b-5b were synthesized by known literature methods.[1-3] Raillar, S. P.; Chen, W.; Sullivan, E.; Bajjalieh, W.; Bhandari, A.; Baer, T. A. *J. Comb. Chem.* 2002, 4, 470-474; Yranzo, G. I.; Reartes, N. R.; Perez, J. D.; Iwataki, I.; Adachi, H. *J. Anal. Appl. Pyrolysis* 1998, 46, 101-112; and Nutaitis, C. F.; Schultz, R. A.; Obaza, J.; Smith, F. X. *J. Org. Chem.* 1980, 45, 4606-4608.

5-(N—(N,O-bis(t-butoxycarbonyl))-hydroxylamine)-5-methyl-Meldrum's acid (1b-diBoc)

To a solution of N,O-bis(t-butoxycarbonyl)-hydroxylamine (1.81 g, 7.75 mmol) in dimethylformamide (25 mL) at room temperature was added sodium hydride, 60% (0.340 g, 8.52 mmol), and the reaction stirred for one hour. To this solution was added 1b-Br (1.84 g, 7.75 mmol), and the reaction proceeded at room temperature for an additional 17 hours. The reaction was diluted with ether (50 mL) and washed with ammonium chloride (×2), water, and brine. The solvent was removed via rotary evaporation, which gave the title compound as an oil that aerated and solidified in vacuo. Recrystallization from dichloromethane and hexanes gave the title compound as a white solid (1.79 g, 59%). $^1$H NMR (400 MHz, CDCl$_3$) δ: 1.90 (s, 3H), 1.83 (s, 3H), 1.80 (s, 3H). $^{13}$C NMR (100 MHz, CDCl$_3$) δ: 167.04, 163.92, 154.77, 151.91, 107.49, 85.51, 84.88, 64.80, 28.78, 28.00, 27.59, 21.84.

5-(N-hydroxylamine)-5-methyl-Meldrum's acid hydrochloride monohydrate (1a)

To a solution of 1b-diBoc (0.190 g, 0.488 mmol) in dichloromethane (10 mL) and methanol (0.99 mL) at 0° C. was added acetyl chloride (1.7 mL, 24 mmol) over two minutes. The reaction was allowed warm to room temperature in the ice bath, and continued to stir overnight. The white precipitate was filtered and characterized as the title compound (0.094 g, 86%). Recrystallization from methanol and dichloromethane gave X-ray quality crystals. $^1$H NMR (400 MHz, d$_6$-DMSO) δ: 10.32 (s, 1H), 8.40 (br. s, 3H), 1.73 (s, 3H), 1.71 (s, 3H), 1.44 (s, 3H). $^{13}$C NMR (100 MHz, d$_6$-DMSO) δ: 168.99, 105.57, 66.14, 28.88, 28.33, 20.96.

5-(acetyl-O-methoxyoxime)-Meldrum's acid (2b-H$^+$)

To a solution of 5-acetyl-Meldrum's acid (1.644 g, 8.831 mmol) in methanol (50 mL) at room temperature was added O-methoxyhydroxylamine hydrochloride (0.738 g, 8.84 mmol) and sodium bicarbonate (0.743 g, 8.84 mmol), and the reaction continued at room temperature for 24 hours. The reaction was concentrated in vacuo, redissolved in dichloromethane, filtered, and concentrated in vacuo to give the title compound as a light yellow solid (1.714 g, 90%). $^1$H NMR (400 MHz, CDCl$_3$) δ: 13.11 (s, 1H), 3.88 (s, 3H), 2.71 (s, 3H), 1.69 (6H). $^{13}$C NMR (100 MHz, CDCl$_3$) δ: 169.77, 166.95, 162.58, 103.12, 80.79, 64.68, 26.46, 14.86. HR-MS (FAB). found m/z=216.08696 (MH$^+$); calc. for C$_9$H$_{13}$NO$_5$: 216.08720.

5-(acetyl-O-methoxyoxime)-5-bromo-Meldrum's acid (2b-Br)

To a solution of 4b-H$^+$ (0.681 g, 2.87 mmol) and triethylamine (0.40 mL, 2.87 mmol) in dichloromethane (20 mL) at 0° C. was added a solution of bromine (0.15 mL, 2.87 mmol) in dichloromethane (2 mL). The reaction was stirred for five minutes then extracted with water and brine, dried over magnesium sulfate, and concentrated in vacuo to give the title compound as an orange solid (0.810 g, 96%). $^1$H NMR (400 MHz, CDCl$_3$) δ: 3.94 (s, 3H), 2.19 (s, 3H), 1.85 (s, 3H), 1.78 (s, 3H). $^{13}$C NMR (100 MHz, CDCl$_3$) δ: 161.53, 151.23, 107.27, 63.19, 55.82, 28.74, 28.38, 12.71. HR-MS (FAB). found m/z=295.99537 (MH$^+$); calc. for C$_9$H$_{12}$BrNO$_5$: 295.99566.

5-(acetyl-O-methoxyoxime)-5-(N—(N,O-bis(t-butoxycarbonyl))-hydroxylamine)-Meldrum's acid (2b-diBoc)

To a solution of N,O-bis(t-butoxycarbonyl)-hydroxylamine (0.642 g, 2.75 mmol) in dimethylformamide (20 mL) at room temperature was added sodium hydride, 60% (0.121 g, 3.03 mmol), and the reaction stirred for one hour. To this solution was added 2b-Br (0.810 g, 2.75 mmol), and the reaction proceeded at room temperature for an additional 24 hours. The reaction was diluted with ether (50 mL) and washed with ammonium chloride (×2), water, and brine then concentrated in vacuo to give crude 2b-diBoc ~30-40% pure by $^1$H NMR, which was used without further purification. $^1$H NMR (400 MHz, CDCl$_3$) δ: 3.94 (s, 3H), 1.99 (br. s., 3H), 1.82 (br. s., 3H), 1.73 (s, 3H), 1.51 (s, 9H), 1.48 (s, 9H).

5-(N-hydroxylamine)-5-(acetyl-O-methoxyoxime)-Meldrum's acid (2a)

To a solution of 2b-diBoc from the previous reaction in methanol (20 mL) at 0° C. was added acetyl chloride (4 mL) over three minutes. The reaction was allowed warm to room temperature in the ice bath, and continued to stir overnight. The reaction was concentrated in vacuo, redissolved in dichloromethane, filtered, and the filtrate was concentrated in vacuo. Recrystallization from dichloromethane and hexanes gave the title compound as pale orange needles (0.68 g, 10% over two steps). $^1$H NMR (400 MHz, d$_6$-DMSO) δ: 8.38 (d, 1H, J=2.3 Hz), 6.94 (d, 1H, J=2.4 Hz), 3.81 (s, 3H), 1.91 (s, 3H), 1.74 (s, 3H), 1.71 (s, 3H). HR-MS (FAB). found m/z=247.09360 (MH$^+$); calc. for C$_9$H$_{14}$N$_2$O$_6$: 247.09301.

5-bromo-5-ethyl-N,N-dimethylbarbituric acid (3b-Br)

To a solution of 3b-H$^+$ (1.06 g, 5.74 mmol) and triethylamine (0.81 mL, 5.74 mmol) in dichloromethane (50 mL) at 0° C. was added a solution of bromine (0.30 mL, 5.74 mmol) in dichloromethane (2 mL). The reaction was stirred for five minutes then extracted with water and brine, dried over magnesium sulfate, and concentrated in vacuo to give the title compound as a white solid (1.42 g, 94%). $^1$H NMR (400 MHz, CDCl$_3$) δ: 3.38 (s, 6H), 2.61 (q, 2H), 0.85 (t, 3H). $^{13}$C NMR (100 MHz, CDCl$_3$) δ: 166.07, 150.09, 49.93, 30.30, 29.66, 10.70. HR-MS (FAB). found m/z=265.00118 (MH$^+$); calc. for C$_8$H$_{11}$BrN$_2$O$_3$: 265.00108.

5-(N—(N,O-bis(t-butoxycarbonyl))-hydroxylamine)-5-ethyl-N,N-dimethylbarbituric acid (3b-diBoc)

To a solution of N,O-bis(t-butoxycarbonyl)-hydroxylamine (1.26 g, 5.41 mmol) in dimethylformamide (50 mL) at room temperature was added sodium hydride, 60% (0.238 g, 5.95 mmol), and the reaction stirred for one hour. To this solution was added 3b-Br (1.42 g, 5.41 mmol), and the reaction proceeded at room temperature for an additional 20 hours. The reaction was diluted with ether (50 mL) and washed with ammonium chloride (×2), water, and brine. The solvent was removed via rotary evaporation, which gave the title compound as an oil that aerated and solidified in vacuo. Recrystallization from dichloromethane and hexanes gave the title compound as a white solid (1.67 g, 74%). $^1$H NMR (400 MHz, CDCl$_3$) δ: 3.35 (s, 3H), 3.33 (s, 3H), 2.17 (m, 2H), 1.54 (s, 9H), 1.41 (br.s., 9H), 0.89 (t, 3H). $^{13}$C NMR (100 MHz, CDCl$_3$) δ: 169.60, 166.47, 151.81, 150.74, 85.20, 84.40, 70.70, 29.41, 29.03, 28.82, 27.99, 27.94, 27.61, 27.57, 7.88. HR-MS (FAB). found m/z=416.20253 (MH$^+$); calc. for C$_{18}$H$_{29}$N$_3$O$_8$: 416.20329.

5-(N-hydroxylamine)-5-ethyl-N,N-dimethylbarbituric acid hydrochloride (3a)

To a solution of 3b-diBoc (0.415 g, 1 mmol) in dichloromethane (20 mL) and methanol (2.0 mL) at 0° C. was added acetyl chloride (3.5 mL, 50 mmol) over three minutes. The reaction was allowed warm to room temperature in the ice bath, and continued to stir overnight. The white precipitate was filtered and characterized as the title compound (0.109 g, 43%). Recrystallization from methanol and dichloromethane gave X-ray quality crystals. $^1$H NMR (400 MHz, d$_6$-DMSO) δ: 10.27 (s, 1H), 7.24 (t, 1H, J=50.8 Hz), 3.21 (s, 6H), 1.78 (q, 2H, J=7.4 Hz), 0.72 (t, 3H, J=7.7 Hz). Rearrangement to 5 precluded the collection of $^{13}$C NMR. HR-MS (FAB). found m/z=216.09879 (MH$^+$); calc. for C$_8$H$_{13}$N$_3$O$_4$: 216.09843.

5-(acetyl-O-methoxyoxime)-N,N-dimethylbarbituric acid (4b-H$^+$)

To a suspension of 5-acetyl-N,N-dimethylbarbituric acid (15.43 g, 77.8 mmol) in methanol (125 mL) was added O-methoxyhydroxylamine hydrochloride (6.50 g, 77.8 mmol) and sodium bicarbonate (6.54 g, 77.8 mmol). The reaction was heated to reflux for one hour then allowed to cool on ice. The precipitate was filtered, re-dissolved in dichloromethane, filtered, and the solution was concentrated in vacuo to give the title compound as a white solid (15.36 g, 87%). $^1$H NMR (400 MHz, CDCl$_3$) δ: 14.54 (s, 1H), 3.88 (s, 3H), 3.32 (s, 3H), 3.30 (s, 3H), 2.76 (s, 3H). $^{13}$C NMR (100 MHz, CDCl$_3$) δ: 169.63, 166.11, 162.55, 151.42, 86.97, 64.55, 27.87, 14.75. HR-MS (FAB). found m/z=228.09857 (MH$^+$); calc. for C$_9$H$_{13}$N$_3$O$_4$: 228.09843.

5-(acetyl-O-methoxyoxime)-5-bromo-N,N-dimethylbarbituric acid-N,N-dimethylbarbituric acid (4b-Br)

To a solution of 4b-H$^+$ (7.27 g, 32 mmol) and triethylamine (4.5 mL, 32 mmol) in dichloromethane (50 mL) at 0° C. was added a solution of bromine (1.65 mL, 32 mmol) in dichloromethane (10 mL). The reaction was stirred for five minutes then extracted with water and brine, dried over magnesium sulfate, and concentrated in vacuo to give the title compound as a white solid (9.51 g, 97%). $^1$H NMR (400 MHz, CDCl$_3$) δ: 3.87 (s, 3H), 3.35 (s, 6H), 2.06 (s, 3H). $^{13}$C NMR (100 MHz, CDCl$_3$) δ: 163.77, 151.70, 150.02, 62.87, 60.13, 30.00, 12.69. HR-MS (FAB). found m/z=308.00717 (MH$^+$); calc. for C$_9$H$_{12}$BrN$_3$O$_4$: 308.00690.

5-(acetyl-O-methoxyoxime)-5-(N—(N,O-bis(t-butoxycarbonyl))-hydroxylamine-N,N-dimethylbarbituric acid (4b-diBoc)

To a solution of N,O-bis(t-butoxycarbonyl)-hydroxylamine (5.83 g, 25 mmol) in dimethylformamide (100 mL) at room temperature was added sodium hydride, 60% (1.1 g, 27.5 mmol), and the reaction stirred for one hour. To this solution was added 4b-Br (7.65 g, 25 mmol), and the reaction proceeded at room temperature for an additional 20 hours. The reaction was diluted with ether (150 mL) and washed with ammonium chloride (×2), water, and brine. The solvent was removed via rotary evaporation, which gave the title compound as an oil that aerated and solidified in vacuo. This material was used without further purification. $^1$H NMR (400 MHz, CDCl$_3$) δ: 3.84 (s, 3H), 3.32 (s, 6H), 1.94 (br. m., 3H), 1.52 (s, 9H), 1.46 (br. m., 9H). HR-MS (FAB). found m/z=459.20898 (MH$^+$); calc. for C$_{19}$H$_{30}$N$_3$O$_9$: 459.20910.

5-(N-hydroxylamine)-5-(acetyl-O-methoxyoxime)-N,N-dimethylbarbituric acid (4a)

Methanol (100 mL) at 0° C. was charged with acetyl chloride (25 mL) over 10 minutes then stirred for an additional five minutes. To this acidic solution was added a solution of 4b-diBoc in methanol (70 mL), and the cloudy reaction was allowed to warm to room temperature in the ice bath over night. The reaction was concentrated in vacuo, re-dissolved in dichloromethane, filtered, and the filtrate was concentrated in vacuo to give the title compound as a sticky solid. Recrystallization from dichloromethane and hexanes gave white needles (3.98 g, 62% over two steps). $^1$H NMR (400 MHz, CDCl$_3$) δ: 6.38 (d, 1H, J=4.0 Hz), 5.32 (d, 1H, J=4.0 Hz), 3.82 (s, 3H), 3.36 (s, 6H), 1.89 (s, 3H). $^{13}$C NMR (100 MHz, CDCl$_3$) δ: 167.10, 152.47, 150.86, 74.93, 62.80, 29.38, 10.93. HR-MS (FAB). found m/z=259.10454 (MH$^+$); calc. for C$_9$H$_{14}$N$_4$O$_5$: 259.10424.

4-(acetyl-O-methoxyoxime)-N-phenyl-5-methyl-pyrazolone (6b-H$^+$)

To a suspension of 4-acetyl-N-phenyl-5-methyl-pyrazolone (3.69 g, 17.1 mmol) in methanol (50 mL) was added O-methoxyhydroxylamine hydrochloride (1.43 g, 17.1 mmol) and sodium bicarbonate (1.44 g, 17.1 mmol). The reaction was heated to reflux for one hour then allowed to cool to room temperature. The reaction was concentrated in vacuo, redissolved in dichloromethane, filtered, and the filtrate was concentrated in vacuo to give the title compound as a red brown oil that solidified upon standing (4.15 g, 99%). $^1$H NMR (400 MHz, CDCl$_3$) δ: 7.85 (m, 2H), 7.44 (m, 2H), 7.26 (m, 1H), 3.92 (s, 3H), 2.43 (s, 3H), 2.29 (s, 3H). $^{13}$C NMR (100 MHz, CDCl$_3$) δ: 170.58, 156.30, 155.54, 154.44, 146.17, 138.22, 128.93, 125.89, 120.67, 120.62, 118.75, 96.46, 62.15, 43.06, 16.94, 15.75, 12.95. HR-MS (FAB). found m/z=246.12350 (MH$^+$); calc. for C$_{13}$H$_{15}$N$_3$O$_2$: 246.12425.

4-(acetyl-O-methoxyoxime)-4-bromo-N-phenyl-5-methyl-pyrazolone (6b-Br)

To a biphasic mixture of 6b-H$^+$ (1.078 g, 4.4 mmol) and sodium bicarbonate (0.369 g, 4.4 mmol) in dichloromethane (20 mL) and water (20 mL) at room temperature was added bromine (0.23 mL, 4.4 mmol) at once. The reaction was vigorously stirred for five minutes, transferred to a separatory funnel and shaken until a clear, colorless aqueous layer resulted. The organic layer was separated, dried over magnesium sulfate, filtered, and concentrated in vacuo to give the title compound as a brown oil (1.38 g, 97%). $^1$H NMR (400 MHz, CDCl$_3$) δ: 7.88 (m, 2H), 7.40 (m, 2H), 7.22 (m, 1H), 3.90 (s, 3H), 2.44 (s, 3H), 2.22 (s, 3H). $^{13}$C NMR (100 MHz, CDCl$_3$) δ: 167.06, 157.83, 151.27, 137.69, 129.11, 125.78, 119.08, 62.73, 56.61, 15.71, 11.70. HR-MS (FAB). found m/z=326.03272 (MH$^+$); calc. for C$_{13}$H$_{14}$BrN$_3$O$_2$: 326.03219.

4-(acetyl-O-methoxyoxime)-4-(N—(N,O-bis(t-butoxycarbonyl))-hydroxylamine-N-phenyl-5-methyl-pyrazolone (6b-diboc)

To a solution of N,O-bis(t-butoxycarbonyl)-hydroxylamine (0.992 g, 4.25 mmol) in dimethylformamide (20 mL) at room temperature was added sodium hydride, 60% (0.187 g, 4.68 mmol), and the reaction stirred for one hour. To this solution was added 6b-Br (1.38 g, 4.25 mmol), and the reaction proceeded at room temperature for 30 minutes. The reaction was diluted with ether (50 mL) and washed with ammonium chloride (×2), water, and brine. The solvent was removed via rotary evaporation, which gave the title compound as an oil that aerated and solidified in vacuo. This material was used without further purification. $^1$H NMR (400 MHz, CDCl$_3$) δ: 7.89 (m, 2H), 7.37 (m, 2H), 7.16 (m, 1H), 3.85 (s, 3H), 2.24 (br. s., 3H), 2.05 (br. m., 3H), 1.52 (s, 9H), 1.40 (br. m., 9H).

4-(N-hydroxylamine)-4-(acetyl-O-methoxyoxime)-N-phenyl-5-methyl-pyrazolone (6a)

To a solution of 6b-diBoc from the previous reaction in methanol (50 mL) at 0° C. was added acetyl chloride (3 mL) over three minutes. The reaction was allowed warm to room temperature in the ice bath, and continued to stir overnight. The reaction was concentrated in vacuo, redissolved in dichloromethane, filtered, and the filtrate was concentrated in vacuo to give the title compound as a sticky solid. Recrystallization from dichloromethane and hexanes gave the title compound as white needles (0.412 g, 35% over two steps). $^1$H NMR (400 MHz, CDCl$_3$) δ: 7.92 (m, 2H), 7.41 (m, 2H), 7.20 (m, 1H), 6.25 (d, 1H, J=2.5 Hz), 4.68 (d, 1H, J=2.5 Hz), 3.92 (s, 3H), 2.23 (s, 3H), 1.79 (s, 3H). $^{13}$C NMR (100 MHz, CDCl$_3$) δ: 170.23, 159.62, 148.66, 137.85, 129.07, 125.59, 119.03, 78.10, 62.59, 14.43, 11.05. HR-MS (FAB). found m/z=277.12953 (MH$^+$); calc. for C$_{13}$H$_{16}$N$_4$O$_3$: 277.13007.

General Procedure for 7a-12a

To a solution of pyrazolones 7b-12b (1 mmol) and ammonium chloride (10 mmol) in methanol (10 mL) and water (10 mL) at room temperature was added Angeli's salt (2 mmol) at once, and the reaction stirred for one hour. The resulting solution was extracted with dichloromethane (×2), and the combined organic layers were washed with brine, dried over magnesium sulfate, and concentrated in vacuo to give 7a-12a in 81% (7a) and quantitative (8a-12a) conversions. Recrystallization from dichloromethane and hexanes gave pyrazolone HNO donors 7a-12a as white solids.

4-(N-hydroxylamine)-4-(acetyl-O-methoxyoxime)-N-methyl-5-methyl-pyrazolone (7a)

$^1$H NMR (400 MHz, CDCl$_3$) δ: 3.89 (s, 3H), 3.32 (s, 3H), 2.11 (s, 3H), 1.73 (s, 3H). $^{13}$C NMR (100 MHz, CDCl$_3$) δ: 171.68, 158.97, 76.62, 62.53, 31.77, 14.39, 10.96. HR-MS (FAB). found m/z=215.11454 (MH$^+$); calc. for C$_8$H$_{14}$N$_4$O$_3$: 215.11442 (MH$^+$).

4-(N-hydroxylamine)-4-methyl-N-phenyl-5-methyl-pyrazolone (8a)

$^1$H NMR (400 MHz, CDCl$_3$) δ: 7.93 (dd, 2H), 7.40 (dd, 2H), 7.18 (t, 1H), 5.70 (bs, 1H), 4.77 (s, 1H), 2.21 (s, 3H), 1.28 (s, 3H). $^{13}$C NMR (100 MHz, CDCl$_3$) δ: 174.06, 162.07, 138.12, 129.05, 125.31, 118.86, 71.23, 16.97, 13.33. HR-MS (FAB). found m/z=220.10932 (MH$^+$); calc. for C$_{11}$H$_{13}$N$_3$O$_2$: 220.10860 (MH$^+$).

4-(N-hydroxylamine)-4-methyl-N-methyl-5-methyl-pyrazolone (9a)

$^1$H NMR (400 MHz, CDCl$_3$) δ: 5.59 (bs, 1H), 4.93 (s, 1H), 3.31 (s, 3H), 2.09 (s, 3H), 1.18 (s, 3H). $^{13}$C NMR (100 MHz, CDCl$_3$) δ: 175.58, 162.00, 69.88, 31.50, 16.60, 13.11. HR-MS (FAB). found m/z=158.09320 (MH$^+$); calc. for C$_6$H$_{11}$N$_3$O$_2$: 158.09295 (MH$^+$).

4-(N-hydroxylamine)-4-methyl-N-(4-chlorophenyl)-5-methyl-pyrazolone (10a)

$^1$H NMR (400 MHz, CDCl$_3$) δ: 7.90 (d, 2H), 7.35 (d, 2H), 2.20 (s, 3H), 1.28 (s, 3H). $^{13}$C NMR (100 MHz, CDCl$_3$) δ: 173.96, 162.18, 136.77, 130.36, 129.09, 119.92, 71.19, 16.92, 13.31. HR-MS (FAB). found m/z=254.06968 (MH$^+$, $^{35}$Cl), 256.06703 (MH$^+$, $^{37}$Cl); calc. for C$_{11}$H$_{12}$ClN$_3$O$_2$: 254.06963 (MH$^+$, $^{35}$Cl), 256.06668 (MH$^+$, $^{37}$Cl).

4-(N-hydroxylamine)-4-methyl-N-(2-chlorophenyl)-5-methyl-pyrazolone (11a)

$^1$H NMR (400 MHz, CDCl$_3$) δ: 7.50 (m, 1H), 7.43 (m, 1H), 7.33 (m, 2H), 2.19 (3H), 1.34 (3H). $^{13}$C NMR (100 MHz, CDCl$_3$) δ: 174.71, 162.25, 134.58, 132.09, 130.64, 130.07, 129.14, 127.74, 70.09, 16.97, 13.35. HR-MS (FAB). found m/z=254.06967 (MH$^+$, $^{35}$Cl), 256.06718 (MH$^+$, $^{37}$Cl); calc. for C$_{11}$H$_{12}$ClN$_3$O$_2$: 254.06963 (MH$^+$, $^{35}$Cl), 256.06668 (MH$^+$, $^{37}$Cl).

4-(N-hydroxylamine)-4-methyl-5-methyl-pyrazolone (12a)

$^1$H NMR (400 MHz, CDCl$_3$) δ: 2.09 (s, 3H), 1.21 (s, 3H).

Example 2: HNO Production

The compounds described herein are believed to donate HNO based on the general strategy shown in Scheme 4 wherein X is a leaving group. Piloty's acid and its derivatives, with sulfinate leaving groups, are classic examples of this strategy. The compounds described herein employ carbon-based leaving groups such that HNO is released along with a stable carbanion at neutral pH.

Scheme 4. HNO release

General Scheme:

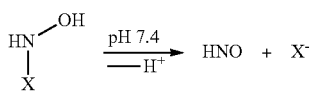

Specific Examples: (a) HNO release from Medrum's acid derivatives 1a and 2a at pH 7.4, 37° C.

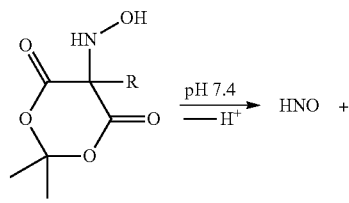

1a R: CH$_3$
2a R: C(CH$_3$)=NOCH$_3$

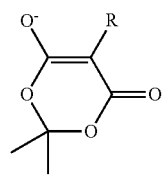

1b R: CH$_3$
2b R: C(CH$_3$)=NOCH$_3$ (b) HNO release from barbituric acids 3a and 4a at pH 7.4, 37° C.

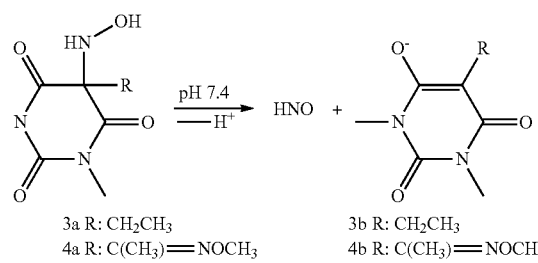

3a R: CH$_2$CH$_3$
4a R: C(CH$_3$)=NOCH$_3$

3b R: CH$_2$CH$_3$
4b R: C(CH$_3$)=NOCH$_3$ (c) HNO release from pyrazolones 6a and 12a at pH 7.4, 37° C.

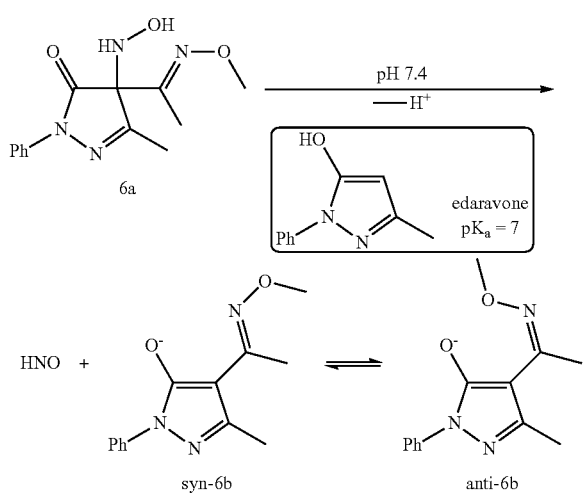

Nitrous oxide is produced via the dimerization and dehydration of HNO, and is the most common marker for HNO production (Fukuto, J. M. et al., *Chem. Res. Toxicol.* 2005, 18, 790-801). HNO, however, can also be partially quenched by oxygen to yield a product that does not produce N$_2$O (see Mincione, F. et al., *J Enzyme Inhibition* 1998, 13, 267-284; and Scozzafava, A. et al., *J. Med. Chem.* 2000, 43, 3677-3687.) Using Angeli's salt (AS) as a benchmark, the relative amounts of N$_2$O released from compounds were examined via gas chromatography (GC) headspace analysis.

Gas chromatography was performed on a Varian CP-3800 instrument equipped with a 1041 manual injector, electron capture detector, and a 25 m 5 Å molecular sieve capillary column. Grade 5.0 nitrogen was used as both the carrier (8 mL/min) and the make-up (22 mL/min) gas. The injector oven and the detector oven were kept at 200° C. and 300° C., respectively. All nitrous oxide analyses were performed with the column oven held constant at 150° C. All gas injections were made using a 100 µL gastight syringe with a sample-lock. Samples were prepared in 15 mL amber headspace vials with volumes pre-measured for sample uniformity (actual vial volume ranges from 15.19-15.20 mL). Vials were charged with 5 mL of PBS buffer containing DTPA, purged with argon, and sealed with a rubber septum. The vials were equilibrated for at least 10 minutes at 37° C. in a dry block heater. A 10 mM stock solution of Angeli's salt (AS) was prepared in 10 mM sodium hydroxide, and HNO donors 1a-4a, 6a (10 mM) were prepared in acetonitrile or methanol and used immediately after preparation. From these stock solutions, 50 µL was introduced into individual thermally-equilibrated headspace vials using a gastight syringe, yielding final substrate concentrations of 0.1 mM. Substrates were then incubated long enough to ensure complete decomposition and equilibration of N$_2$O with the headspace. The headspace (60 µL) was then sampled and injected five successive times using a gastight syringe with a sample lock. This was repeated for n≥3 vials per donor. The nitrous oxide yield was averaged and reported relative to the standard, Angeli's salt. For chemical trapping of HNO, glutathione (100 µL of 10 mM in PBS) was added prior to HNO donor addition to give a final glutathione concentration of 0.2 mM, and headspace sampling for N$_2$O was analogously performed as stated above. Results are provided in Table 4.

TABLE 4

Results of N$_2$O headspace analysis

| Compound | % HNO[a] | % Carbanion[b] | $t_{1/2}$ (min)[c] |
|---|---|---|---|
| 1a | 2 | 4[d] | f |
| 2a | 25 | 34[d] | 0.9 |
| 3a | 2 | 6[e] | f |
| 4a | 110 | >95 | 0.7 |
| 6a | 110 | >95 | 9.5 |

[a]Donor compounds (0.1 mM) were incubated at 37° C. in PBS, pH 7.4. HNO yields are reported relative to the standard HNO donor, Angeli's salt, as determined by N$_2$O headspace analysis (SEM ± 5%; n = 3). N$_2$O production was completely quenched with added glutathione (0.2 mM).
[b]Yields of carbanions 1b-4b, 6b determined by $^1$H NMR spectroscopy.
[c]Determined from UV-Vis kinetic experiments.
[d]Relative to the major byproduct, acetone.
[e]Relative to rearrangement byproduct 5.
f Not determined.

The data presented on compounds 1a-4a and 6a suggest that the ability of these N-substituted hydroxylamines to generate HNO is based mainly on the nature of the leaving group. To produce HNO efficiently, the driving force for the formation of a stabilized carbanion must overcome other non-HNO producing reaction pathways.

With respect to Meldrum's acid derivative 1a, only trace amounts of N$_2$O were observed. Although Meldrum's acid (pK$_a$=4.8) is completely ionized at pH 7.4 and its 2,2-dimethyl derivative has a hydrolysis half-life of about 12 hours under physiological conditions, the major product observed by $^1$H NMR spectroscopy is acetone, indicative of a dominant ring-opening reaction pathway for 1a.

Compared to 1a, an enhanced HNO yield was observed for Meldrum's acid derivative 2a. However, acetone is still the major product, indicating that the non-HNO producing ring-opening reaction pathway remains competitive with the desired pathway.

Similar to 1a, barbiturate 3a produced little HNO. Following a large-scale decomposition, the major organic byproduct was isolated and identified by X-ray crystallography, revealing that barbiturate 3a primarily undergoes an intramolecular rearrangement to compound 5 in pH 7.4 buffer solutions (Scheme 5).

Scheme 5. Major reaction pathway for barbiturate 3a

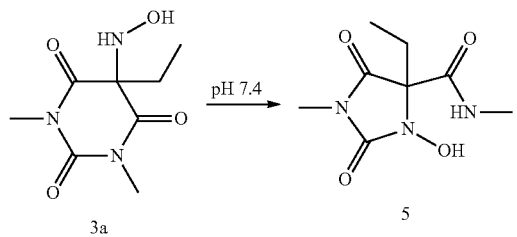

Given the positive impact that an electron deficient O-methyloxime group had on HNO production from Meldrum's acid derivatives 1a and 2a, an analogous substitution on the barbituric acid ring system was analyzed. Exchanging the ethyl group in 3a with an O-methyloxime in barbiturate 4a strongly favors the generation of HNO, as reflected by the high yield of $N_2O$ observed following decomposition (Table 4). HNO was confirmed as the source of $N_2O$ for this and the other precursors examined by quenching with glutathione, a known efficient trap for HNO.

Figure 2A:
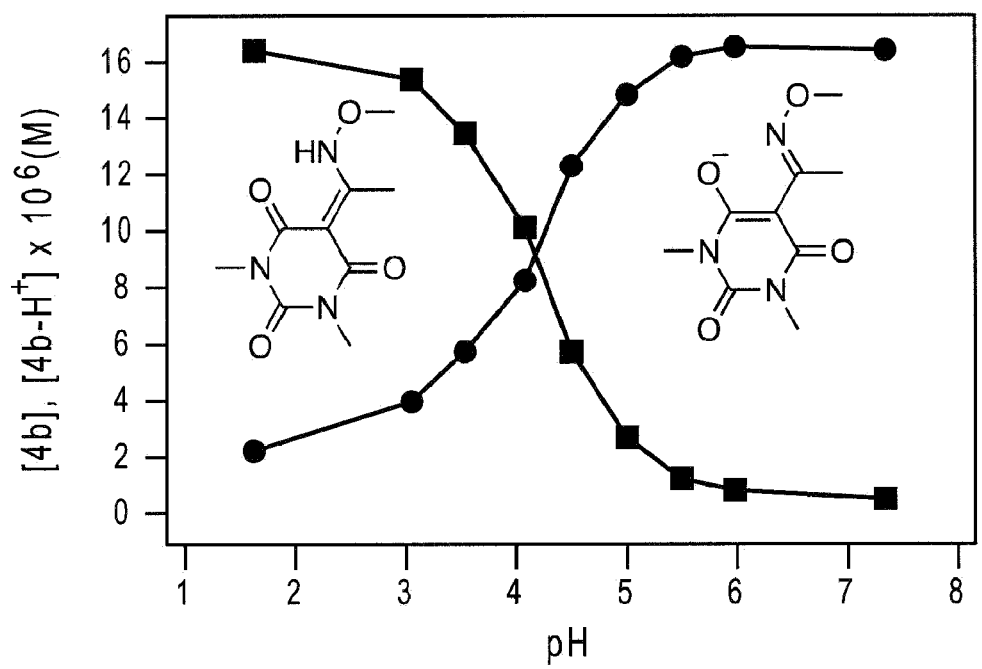
FIG. 2A and FIG. 2B show a graph plotting the concentration of 4b, 4b-H$^+$ (FIG. 2A) and 6b, 6b-H$^+$ (FIG. 2B) as a function of pH.
Figure 3A:
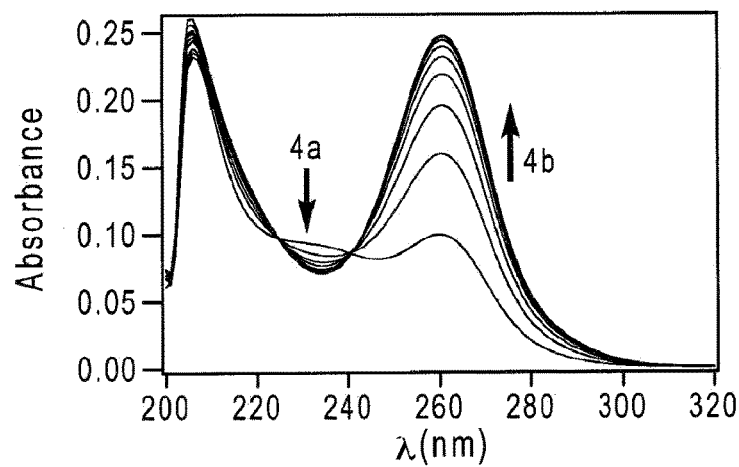
FIG. 3A and FIG. 3B show the UV-Vis spectra of the decomposition of 4a (time between traces=30 s) (FIG. 3A) and 6a (time between traces=240 s) (FIG. 3B), at 37° C. in PBS, pH 7.4.
Figure 3B:
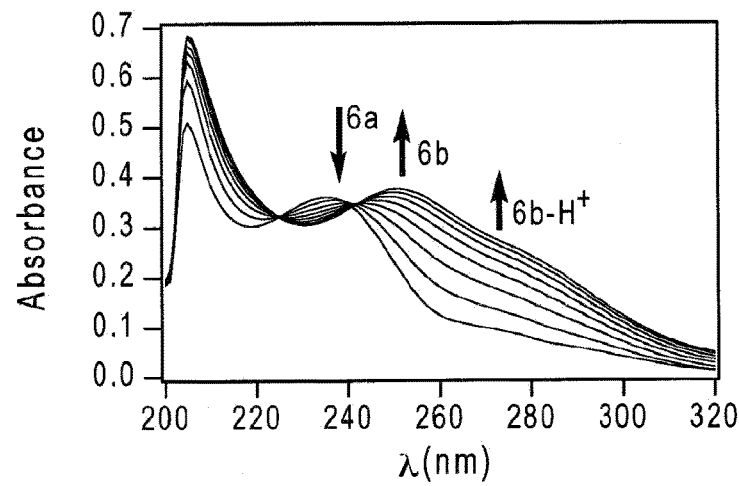

The decomposition of 4a was monitored by $^1$H NMR spectroscopy in PBS (pH 7.4, room temperature), and the only detectable organic byproduct was carbanion 4b (FIG. 1A). With an estimated $pK_a$ of ca. 4.2 (FIG. 2A), the byproduct is completely ionized at neutral pH. Influenced by the O-methyloxime group, this $pK_a$ is slightly lower than that of N,N-dimethyl barbituric acid ($pK_a$=4.7). The kinetics of decomposition from 4a to 4b was monitored by UV-Vis spectroscopy given the distinctive absorbance of anion 4b ($\lambda_{max}$=261 nm) (FIG. 3A). Analysis of the decomposition rate as a function of pH reveals a sharp increase near pH 8 (FIG. 3B). Barbiturate 4a has a half-life of ca. 1 min at pH 7.4 and 37° C. (FIG. 3A), but is relatively stable at pH 4.0 and room temperature, with a half-life of about 1 day under these conditions.

To demonstrate the generality of this approach for HNO generation, another N-substituted hydroxylamine with a suitable carbon-based leaving group was examined. Like barbiturates 3a and 4a, pyrazolone 6a (synthesized analogously to compounds 1a-4a) also takes advantage of the formation of an aromatic byproduct (6b) (Scheme 4c), and efficiently produces HNO with a half-life of ca. 10 min at pH 7.4, 37° C. (Table 4). Another potentially practical benefit enjoyed by precursor 6a is that byproduct 6b, formed along with HNO, is a derivative of edaravone, a potent antioxidant already in clinical use for the treatment of stroke and cardiovascular disease.

Figure 2B:
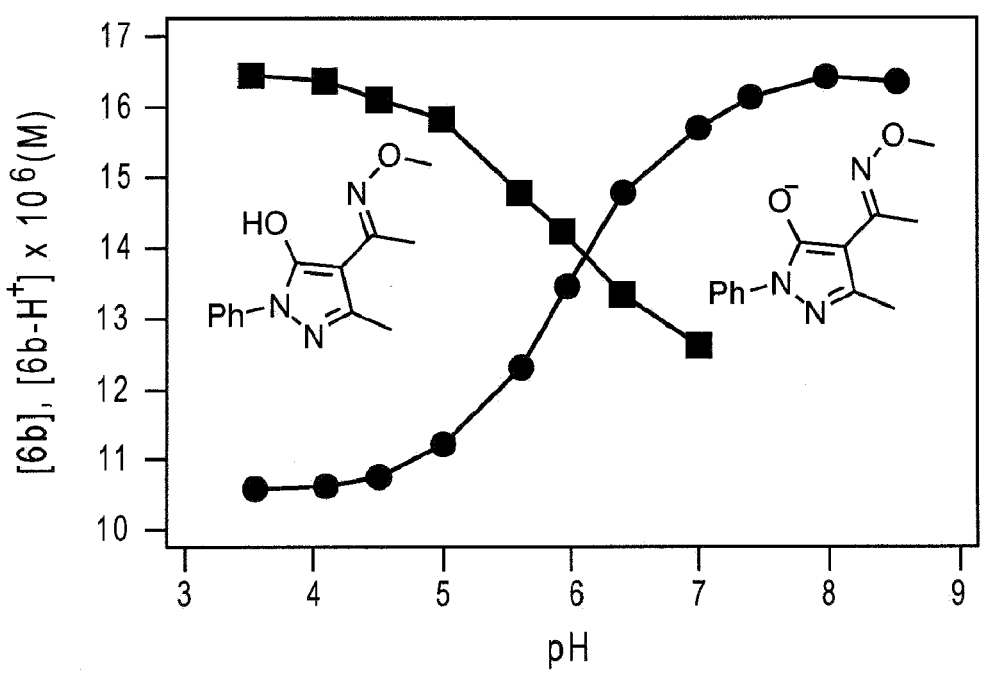
Figure 3C:
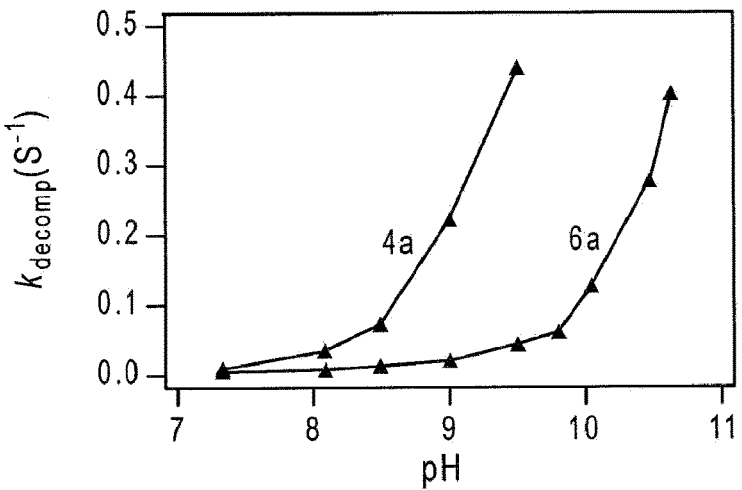
FIG. 3C shows a graph plotting the decomposition rate (as determined by UV-Vis analysis) as a function of pH at 25° C. of 4a (monitored at 261 nm) and 6a (monitored at 253 nm).

The decomposition of 6a was analyzed similarly to that of 4a by $^1$H NMR spectroscopy in PBS (pH 7.4, room temperature) (FIG. 1C). The only organic byproducts observed by this analysis are the syn (major) and anti (minor) isomers of 6b (Scheme 4c), and the relative abundance of these isomers is unchanged at high and low pH. Donor 6a, as well as 2a and 4a, are observed to be all syn by NMR analysis and X-ray crystallography. The $pK_a$ of 6b/6b-H$^+$ is estimated to be ca. 6 (FIG. 2B), shifted below that of edaravone ($pK_a$=7) by O-methyloxime substitution, indicating that nearly all of this byproduct is ionized at pH 7.4. As was the case for precursor 4a, the decomposition rate of pyrazolone 6a is highly pH dependent, here with a sharp increase near pH 10 (FIG. 3C); 6a is much more stable at pH 4.0, with a half-life of about 25 hours at room temperature. The half-lives of compounds 6a, 7a, 8a, 9a, 10a, 11a and 12, and the $pK_a$ of the compounds' byproducts are set forth in Table 5.

TABLE 5

Half-lives and $pK_a$ of byproducts

| Compound | Condition$^a$ | $pK_a$ of byproduct | $t_{1/2}$ |
|---|---|---|---|
| 6a | A | 6.0 (6b) | 9.5 min |
| 7a | A | 6.7 (7b) | 23 min |
| 8a | B | 7.5 (8b) | 16 h |
| 8a | C | | 28 h |
| 8a | D | | 50 h |
| 8a | E | | 100 h |
| 9a | B | 8.5 (9b) | 48 h |
| 9a | F | | 84% remains after 48 h |
| 10a | G | 7.3 (10b) | 3.5 d |
| 11a | G | 7.5 (11b) | 5 d |
| 12a | G | 9.0 (12.b) | 70% remains after 7 d |

$^a$A: pH 7.4, 37° C., 0.1M PBS, 100 μL DTPA, air (UV/Vis); B: pH 7.4, 37° C., 10% D$_2$O, 0.25M PBS, no chelator, air ($^1$H NMR); C: pH 7.4, 37° C., 10% D$_2$O, 0.25M PBS, 100 μL DTPA, BME (20 equiv.), argon ($^1$H NMR); D: pH 7.4, 37° C., 10% D$_2$O, 0.25M PBS, 100 μL DTPA, GSH (2 equiv.), argon ($^1$H NMR); E: pH 7.4, 37° C., 10% D$_2$O, 0.25M PBS, 100 μL DTPA, 12b (1 equiv.), air ($^1$H NMR); F: pH 7.4, 37° C., 10% D$_2$O, 0.25M PBS, no chelator, nitrogen ($^1$H NMR); G: pH 7.4, 37° C., 10% D$_2$O, 0.25M PBS, 100 μL DTPA, air ($^1$H NMR).

Example 3: Acute Cardiovascular Effects

The acute cardiovascular effects of compounds 4a and 6a, when administered intravenously to Sprague-Dawley rats at an infusion rate of 100 μg/kg/min, were examined by means of pressure-volume (PV) curve (loops) analysis. PV families/relationships were generated via pre-load variation and hemodynamic indices were compared to baseline values. Each test article was administered to 5 rats.

Rats were intraperitoneally (IP) anesthetized to effect with pentobarbital (~50 mg/kg), shaved and positioned in dorsal recumbence, endotracheally intubated and ventilated (~90 breaths/min, ~2.5 mL tidal volume with 95% O$_2$/5% CO$_2$) with an adjustable small animal ventilator (Harvard Apparatus). Anesthesia was maintained with a continuous pentobarbital infusion (to effect, ~3 to 5 mg/kg/h, IV) until completion of the experiment via an indwelling catheter placed in a femoral vein. Subsequently, transthoracic needle electrodes forming a single-lead ECG were placed. For LV mechano-energetic evaluation, the right carotid artery was isolated, dissected free from the surrounding tissue, and cannulated with a 2F high-fidelity conductance/microman-ometer catheter (Millar Instruments). This catheter was advanced retrograde across the aortic valve and into the LV chamber in order to simultaneously determine left-ventricu lar pressure and volume (via conductivity). An appropriately sized balloon catheter (filled with distilled water) was placed and advanced into the inferior vena cava, via a femoral vein; brief inflation of this occluder/balloon is used to acutely decrease myocardial preload. Meanwhile, in order to record arterial pressures, a 2F high-fidelity micromanometer catheter (Millar Instruments) was inserted into a femoral artery and advanced towards the abdominal aorta. Finally, an in-dwelling catheter was placed into the jugular vein for administration of test article.

data (PV loops) generated during brief periods of preload reduction:

Pressure volume area (PVA) and stroke work (SW).

End-systolic (ESPVR) and end-diastolic (EDPVR) pressure volume relationships.

End systolic pressure and stroke volume relationship (Arterial Elastance, Ea).

Data are presented as means with standard errors (mean±SEM) in Table 6.

TABLE 6

Acute cardiovascular effects in Sprague-Dawley rats

| Hemodynamic Index | Baseline | | +4a | | Baseline | | +6a | |
|---|---|---|---|---|---|---|---|---|
| | Mean | SEM | Mean | SEM | Mean | SEM | Mean | SEM |
| Systolic Blood Pressure (mmHg) | 147 | 6 | 85 | 7 | 160 | 6 | 130 | 7 |
| Diastolic Blood Pressure (mmHg) | 109 | 5 | 62 | 6 | 121 | 4 | 97 | 5 |
| Mean Blood Pressure (mmHg) | 124 | 5 | 71 | 6 | 138 | 5 | 111 | 6 |
| Heart Rate (bp, m) | 365 | 15 | 350 | 14 | 340 | 15 | 332 | 14 |
| End Diastolic Pressure (mmHg) | 4.7 | 1.4 | 3.4 | 1.3 | 4.4 | 1.4 | 3.6 | 1.5 |
| End Systolic Pressure (mmHg) | 134 | 3 | 71 | 4 | 141 | 5 | 113 | 6 |
| Left Ventricular +dP/dt (mmHg/s) | 6392 | 280 | 3518 | 213 | 7689 | 936 | 6044 | 562 |
| Left Ventricular −dP/dt (mmHg/s) | −7585 | 240 | −4096 | 299 | −8257 | 883 | −6549 | 603 |
| Tau (ms) | 8.5 | 0.3 | 7.8 | 0.4 | 8.7 | 0.7 | 8.6 | 0.4 |
| End Diastolic Volume (relative volume units) | 14.6 | 0.7 | 15 | 0.5 | 19.2 | 0.9 | 20 | 0.9 |
| Stroke Volume (relative volume units) | 1 | 0 | 1.2 | 0.2 | 2.2 | 0.4 | 2.4 | 0.5 |
| Stroke Work (relative volume units × mmHg) | 112 | 4 | 74 | 9 | 227 | 27 | 185 | 25 |
| Pressure Volume Area | 343 | 43 | 151 | 16 | 590 | 62 | 318 | 38 |
| Arterial Elastance | 9.2 | 0.5 | 4.8 | 0.3 | 7.4 | 0.5 | 5.7 | 0.5 |
| End Systolic Pressure Volume Relationship | 28.1 | 3.2 | 34.1 | 4 | 23.7 | 2 | 31 | 4.1 |
| End Diastolic Pressure Volume Relationship | 1.7 | 0.2 | 1.6 | 0.2 | 1.8 | 0.2 | 1.5 | 0.3 |
| Pre-Load Recruitable Stroke Work | 37.6 | 4.2 | 54.3 | 5.9 | 42.8 | 6.8 | 58.2 | 4.8 |

Once a steady hemodynamic state was reached following instrumentation, left-ventricular pre-load was acutely reduced by means of brief vena cava occlusions (via transient inflation of the vessel occluder) in order to generate a family of pressure-volume curves/loops; up to three occlusions were performed, allowing for hemodynamic recovery between tests. Following collection of baseline hemodynamic data, infusion of test article was initiated at an infusion rate of 100 μg/kg/min; at 10 μL/min. Pressure-volume analyses were performed again approximately 30 min and 45 min after the initiation of the dose.

The resulting left-ventricular pressure and volume data was analyzed offline (IOX/ECG Auto; EMKA Technologies) in order to generate relationships representing the contractile and energetic state of the myocardium. Systolic (SAP), diastolic (DAP), and mean (MAP) arterial pressures were collected. Left-ventricular mechanical and/or geometrical indices were obtained from the pressure (ESP, EDP, dP/dt max/min, time-constant of relaxation—tau [based on mono-exponential decay with non-zero asymptote]) and volume (ESV, EDV, SV) signal. In addition, the following measurements were derived from left-ventricular pressure-volume Example 4: In Vitro Model to Determine Ability of Compounds or Pharmaceutical Compositions to Treat, Prevent and/or Delay Onset and/or Development of a Disease or Condition Cardiovascular Diseases or Conditions In vitro models of cardiovascular disease can also be used to determine the ability of any of the compounds and pharmaceutical compositions described herein to treat, prevent and/or delay the onset and/or the development of a cardiovascular disease or condition in an individual. An exemplary in vitro model of heart disease is described below.

In-vitro models could be utilized to assess vasorelaxation properties of the compounds and pharmaceutical compositions. Isometric tension in isolated rat thoracic aortic ring segment can be measured as described previously by Crawford, J. H. et al., *Blood* 2006, 107, 566-575. Upon sacrifice, aortic ring segments are excised and cleansed of fat and adhering tissue. Vessels are then cut into individual ring segments (2-3 mm in width) and suspended from a force-displacement transducer in a tissue bath. Ring segments are bathed at 37° C. in a bicarbonate-buffered, Krebs-Henseleit (K-H) solution of the following composition (mM): NaCl 118; KCl 4.6; NaHCO3 27.2; KH2PO4 1.2; MgSO4 1.2; CaCl2 1.75; Na2EDTA 0.03; and glucose 11.1 and perfused continuously with 21% O2/5% CO2/74% N2. A passive load of 2 g is applied to all ring segments and maintained at this level throughout the experiments. At the beginning of each experiment, indomethacin-treated ring segments are depolarized with KCl (70 mM) to determine the maximal contractile capacity of the vessel. Rings are then washed extensively and allowed to equilibrate. For subsequent experiments, vessels are submaximally contracted (50% of KCl response) with phenylephrine (PE, $3 \times 10^{-8}$-$10^{-7}$ M), and L-NMMA, 0.1 mM, is also added to inhibit eNOS and endogenous NO production. After tension development reaches a plateau, compounds or pharmaceutical compositions are added cumulatively to the vessel bath and effects on tension monitored.

In vitro models can be utilized to determine the effects of the compounds and pharmaceutical compositions in changes in developed force and intracellular calcium in heart muscles. Developed force and intracellular calcium can be measured in rat trabeculae from normal or diseased (i.e. rats with congestive heart failure or hypertrophy) as described previously (Gao W. D. et al., *Circ. Res.* 1995, 76:1036-1048). Rats (Sprague-Dawley, 250-300 g) are used in these experiments. The rats are anesthetized with pentobarbital (100 mg/kg) via intra-abdominal injection, the heart exposed by mid-sternotomy, rapidly excised and placed in a dissection dish. The aorta is cannulated and the heart perfused retrograde (~15 mM/min) with dissecting Krebs-Henseleit (H-K) solution equilibrated with 95% O2 and 5% CO2. The dissecting K-H solution is composed of (mM): NaCl 120, NaHCO3 20, KCl 5, MgCl2 1.2, glucose 10, CaCl2 0.5, and 2,3-butanedione monoximine (BDM) 20, pH 7.35-7.45 at room temperature (21-22° C.). Trabeculae from the right ventricle of the heart are dissected and mounted between a force transducer and a motor arm and superfused with normal K-H solution (KCl, 5 mM) at a rate of ~10 ml/min and stimulated at 0.5 Hz. Dimensions of the muscles are measured with a calibration reticule in the ocular of the dissection microscope (×40, resolution ~10 µm).

Force is measured using a force transducer system and is expressed in millinewtons per square millimeter of cross-sectional area. Sarcomere length is measured by laser diffraction. Resting sarcomere length is set at 2.20-2.30 µm throughout the experiments.

Intracellular calcium is measured using the free acid form of fura-2 as described in previous studies (Gao et al., 1994; Backx et al., 1995; Gao et al., 1998). Fura-2 potassium salt is microinjected iontophoretically into one cell and allowed to spread throughout the whole muscle (via gap junctions). The tip of the electrode (~0.2 µm in diameter) is filled with fura-2 salt (1 mM) and the remainder of the electrode is filled with 150 mM KCl. After a successful impalement into a superficial cell in non-stimulated muscle, a hyperpolarizing current of 5-10 nA is passed continuously for ~15 min. Fura-2 epifluorescence is measured by exciting at 380 and 340 nm. Fluorescent light is collected at 510 nm by a photomultiplier tube. The output of photomultiplier is collected and digitized. Ryanodine (1.0 µM) is used to enable steady-state activation. After 15 min of exposure to ryanodine, different levels of tetanizations are induced briefly (~4-8 seconds) by stimulating the muscles at 10 Hz at varied extracellular calcium (0.5-20 mM). All experiments are performed at room temperature (20-22° C.).

Diseases or Conditions Implicating Ischemia/Reperfusion

In vitro models can also be used to determine the ability of any of the compounds and pharmaceutical compositions described herein to treat, prevent and/or delay the onset and/or the development of a disease or condition implicating ischemia/reperfusion injury in an individual.

Cancer

Antitumor activities of the compounds described herein can be assessed using in vitro proliferation assays of tumor cells using well-known methods, such as described in Norris A. J. et al. *Intl. J. Cancer* 2008, 122:1905-1910.

Cells of an appropriate cell line, e.g. human breast cancer cell line MCF-7, are seeded in 96-well tissue culture microtiter plates at ~4000 cells per well for an overnight incubation. Serial 10-fold dilutions of test compounds are added, and the cells are incubated for 72 h. The cell viability is determined using the CellTiter-Glo™ Luminescent Cell Viability Assay (Promega; Madison, Wis.). $IC_{50}$ is measured as the concentration of drug required for inhibiting cell growth by 50%.

Example 5: In Vivo and/or Ex Vivo Models to Determine Ability of Compounds and Pharmaceutical Compositions to Treat, Prevent and/or Delay Onset and/or Development of a Disease or Condition Cardiovascular Diseases or Condition In vivo models of cardiovascular disease can also be used to determine the ability of any of the compounds and pharmaceutical compositions described herein to treat, prevent and/or delay the onset and/or the development of a cardiovascular disease or condition in an individual. An exemplary animal model of heart disease is described below.

In vivo cardiovascular effects obtained with a compound or pharmaceutical composition may be assessed in a control (normal) dog. The study is conducted in adult (25 kg) mongrel (male) dogs chronically instrumented for conscious hemodynamic analysis and blood sampling, as previously described (Katori, T. et al., *Circ. Res.* 2005, 96, 234-243.). Micromanometer transducers in the left ventricle provide pressure, while right atrial and descending aortic catheters provide fluid-pressures and sampling conduits. Endocardial sonomicrometers (anteriorposterior, septal-lateral) measure short-axis dimensions, a pneumatic occluder around the inferior vena cave facilitated pre-load manipulations for pressure-relation analysis. Epicardial pacing leads are placed on the right atrium, and another pair is placed on the right ventricle free wall linked to a permanent pacemaker to induce rapid pacing-cardiac failure. After 10 days of recovery, animals are evaluated at baseline sinus rhythm and with atrial pacing (120-160 bpm). Measurements include conscious hemodynamic recordings for cardiac mechanics.

Compounds described herein are administrated to a healthy control dog at the dose of 1-5 µg/kg/min and the resulting cardiovascular data is obtained.

Demonstration that a compound described herein improves cardiac hemodynamics in hearts with congestive failure: After completing protocols under baseline conditions, congestive heart failure is induced by tachypacing (210 bpm×3 weeks, 240 bpm×1 week), as previously described (Katori, T. et al., *Circ. Res.* 2005, 96: 234-243.). Briefly, end-diastolic pressure and $dP/dt_{max}$ are measured weekly to monitor failure progression. When animals demonstrate a rise in EDP more than 2×, and dP/dt$_{max}$ of >50% baseline, they are deemed ready for congestive heart failure studies.

The values for test compounds and pharmaceutical compositions are obtained after 15 min continuous i.v. infusion (2.5 or 1.25 µg/kg/min) in control and heart failure preparations, respectively, both in the absence and in the presence of volume restoration. For comparison, the same hemodynamic measurements are obtained with AS in heart failure preparations.

Diseases or Conditions Implicating Ischemia/Reperfusion

Ex-vivo models of ischemia/reperfusion can also be used to determine the ability of any of the compounds described herein to treat, prevent and/or delay the onset and/or the development of a disease or condition implicating ischemia/reperfusion injury in an individual. An exemplary ex vivo model of ischemia/reperfusion injury is described below.

Male Wistar rats are housed in identical cages and allowed access to tap water and a standard rodent diet ad libitum. Each animal is anesthetized with 1 g/kg urethane i.p. 10 min after heparin (2,500 U, i.m.) treatment. The chest is opened, and the heart is rapidly excised, placed in ice-cold buffer solution and weighed. Isolated rat hearts are attached to a perfusion apparatus and retrogradely perfused with oxygenated buffer solution at 37° C. The hearts are instrumented as previously described in Rastaldo et al., Am. J. Physiol. 2001, 280, H2823-H2832, and Paolocci et al., Am. J. Physiol. 2000, 279, H1982-H1988. The flow is maintained constant (approximately 9 mL/min/g wet weight) to reach a typical coronary perfusion pressure of 85-90 mmHg. A constant proportion of 10% of the flow rate is applied by means of one of two perfusion pumps (Terumo, Tokyo, Japan) using a 50 mL syringe connected to the aortic cannula. Drug applications are performed by switching from the syringe containing buffer alone to the syringe of the other pump containing the drug (compound or pharmaceutical composition described herein) dissolved in a vehicle at a concentration 10× to the desired final concentration in the heart. A small hole in the left ventricular wall allows drainage of the thebesian flow, and a polyvinyl-chloride balloon is placed into the left ventricle and connected to an electromanometer for recording of left ventricular pressure (LVP). The hearts are electrically paced at 280-300 bpm and kept in a temperature-controlled chamber (37° C.). Coronary perfusion pressure (CPP) and coronary flow are monitored with a second electromanometer and an electromagnetic flow-probe, respectively, both placed along the perfusion line. Left ventricular pressure, coronary flow and coronary perfusion pressure are recorded using a TEAC R-7 1 recorder, digitized at 1000 Hz and analyzed off-line with DataQ-Instruments/CODAS software, which allow quantification of the maximum rate of increase of LVP during systole (dP/dt$_{max}$).

Hearts are perfused with Krebs-Henseleit solution gassed with 95% O2 and 5% CO2 of the following composition: 17.7 mM sodium bicarbonate, 127 mM NaCl, 5.1 mM KCl, 1.5 mM CaCl2, 1.26 mM MgCl2, 11 mM D-glucose, supplemented with 5 µg/mL lidocaine.

The test compound or pharmaceutical compositions are diluted in buffer immediately prior to use. Hearts are allowed to stabilize for 30 min, and baseline parameters are recorded. Typically, coronary flow is adjusted within the first 10 min and kept constant from thereon. After 30 min stabilization, hearts are randomly assigned to one of the treatment groups, and subjected to 30 min global, no-flow ischemia, followed by 30 min of reperfusion (I/R). Pacing of the hearts is stopped at the beginning of the ischemic period and restarted after the third minute of reperfusion.

Hearts in a control group are perfused with a buffer for an additional 29 min after stabilization. Treated hearts are exposed to a test compound or pharmaceutical composition (e.g., 1 µM final concentration for about 20 min followed by a 10 min buffer wash-out period).

In all hearts, pacing is suspended at the onset of ischemia and restarted 3 minutes following reperfusion. As isolated heart preparations may deteriorate over time (typically after 2-2.5 hours perfusion), the re-flow duration is limited to 30 minutes in order to minimize the effects produced by crystalloid perfusion on heart performance, and consistently with other reports.

Assessment of ventricular function: To obtain the maximal developed LVP, the volume of the intra-ventricular balloon is adjusted to an end-diastolic LVP of 10 mmHg during the stabilization period, as reported in Paolocci, supra, and Hare et al., J. Clin. Invest. 1998, 101, 1424-31. Changes in developed LVP, dP/dt$_{max}$ and the end-diastolic value induced by the I/R protocol are continuously monitored. The difference between the end-diastolic LVP (EDLVP) before the end of the ischemic period and during pre-ischemic conditions is used as an index of the extent of contracture development. Maximal recovery of developed LVP and dP/dt$_{max}$ during reperfusion is compared with respective pre-ischemic values.

Assessment of myocardial injury: Enzyme release is a measure of severe myocardial injury that has yet to progress to irreversible cell injury. Samples of coronary effluent (2 mL) are withdrawn with a catheter inserted into the right ventricle via the pulmonary artery. Samples are taken immediately before ischemia and at 3, 6, 10, 20 and 30 min of reperfusion. LDH release is measured as previously described by Bergmeyer et al., Verlag Chemie 1974. Data are expressed as cumulative values for the entire reflow period.

To corroborate the data relative to myocardial injury, determined by LDH release, infarct areas are also assessed in a blinded fashion. At the end of the course (30 min reperfusion), each heart is rapidly removed from the perfusion apparatus, and the LV dissected into 2-3 mm circumferential slices. Following 15 min of incubation at 37° C. in 0.1% solution of nitro blue tetrazolium in phosphate buffer as described in Ma et al., Proc. Natl. Acad. Sci. 1999, 96, 14617-14622, unstained necrotic tissue is separated from the stained viable tissue. The areas of viable and necrotic tissue are carefully separated by an independent observer who is not aware of the origin of the hearts. The weight of the necrotic and non-necrotic tissues is then determined and the necrotic mass expressed as a percentage of total left ventricular mass.

Data may be subjected to statistical methods such as ANOVA followed by the Bonferroni correction for post hoc t tests.

Cancer

Anticancer activities of compounds described herein can be assessed using in vivo mouse xenograft models using methods described in Norris A. J. et al., Intl. J. Cancer 2008, 122, 1905-1910 and Stoyanovsky, D. A. et al., J. Med. Chem. 2004, 47, 210-217).

Mice are inoculated with appropriate tumor cells by subcutaneous injection into the lower flank. Therapy can be started after 1-3 weeks when the tumors have reached an average volume of ~50-60 mm$^3$. Tumor diameters are measured with digital calipers, and the tumor volume is calculated. The anti-tumor efficacy of test compounds is assessed by comparison of tumor size in test group to that in the control group.

Example 6: In Vivo Animal Studies (Acute Treatment, Intravenous Infusion)

This example demonstrates the efficacy of compounds and pharmaceutical compositions described herein to lower pulmonary artery pressure in rats with monocrotaline-induced PH.

Rats (250-250 g) are anesthetized via an intra-muscular (i.m.) injection of ketamine/xylazine (80/10 mg/kg). A half dose (40 mg/kg ketamine/5 mg/kg xylazine) is given as supplemental anesthesia as needed. Animals are placed on a heating pad set to maintain body temperature at approximately 37° C. Body temperature is monitored throughout the experiment. Once consciousness is lost, a pressure transducer is inserted into a femoral artery to measure arterial blood pressure. A fluid filled catheter is inserted through the right jugular vein into the pulmonary artery to measure pulmonary artery pressure via a pressure transducer. A cannula is placed into the left jugular vein for dosing.

Monocrotaline is administered via a single subcutaneous injection (60 mg/kg) approximately 3 weeks prior to the terminal procedure. A baseline pulmonary artery pressure of >30 mmHg is required to initiate study of the compounds described herein. A nitroxyl donor or a compound or pharmaceutical composition as described herein is administered intravenously in a dose-escalation manner in 20 minute intervals from doses of 10 to 300 µg/kg/min. Hemodynamic indices, including MAP (mean arterial pressure), SAP (systolic arterial pressure), DAP (diastolic arterial pressure), HP (heart rate), MPAP (mean pulmonary arterial pressure), SPAP (systolic arterial pressure), DPAP (diastolic pulmonary arterial pressure), are measured. The results of test compounds are illustrated in FIG. 1A-1C, FIG. 2A-2B and FIG. 3A-3C.

For the terminal procedure, after surgical instrumentation and an approximate 10 minute pre-dose equilibration period, test compound or pharmaceutical composition solutions are infused via jugular vein catheter. At the end of the experiment, rats are euthanized under anesthesia via pentobarbital overdose.

Example 7: In Vivo Animal Studies (Acute Treatment, Intravenous Infusion or Inhaled Administration)

This example demonstrates the efficacy of the compounds and pharmaceutical compositions described herein to lower pulmonary artery pressure in dogs with hypoxia-induced PH.

Healthy dogs (10-15 kg) are anesthetized with pentobarbital (20-40 mg/kg. intravenously) and anesthesia is maintained by continuous infusion of pentobarbital at rate of 5-10 mg/kg/h. Dogs are intubated via a tracheotomy, and artificially respired (while monitoring inspired oxygen and expired $CO_2$). The left femoral vein and artery are cannulated for dose administration and arterial blood pressure recording. The right jugular vein is cannulated with a pulmonary artery pressure catheter (Swan Ganz catheter), to measure both pulmonary arterial pressure (PAP) and pulmonary wedge pressure (PWP). This catheter is also used for measurement of cardiac output via thermodilution techniques following rapid injection of cold 5 mL saline. Electrocardiograms are monitored throughout the experiment.

During the baseline and control measurements inspired oxygen is maintained at 40%. Hypoxia is induced by adding nitrogen to the respiratory gas at a rate sufficient to reduce respired oxygen to 10% ($FiO2=10\%$). Each hypoxic condition is maintained for 15-30 minutes and then normoxic ($FiO2=40\%$) control condition is returned. Each dose of test compound or pharmaceutical composition is intravenously administered during the 30 minute hypoxic condition; no drug is infused during the subsequent normoxia until the next dose is given. Test compounds or pharmaceutical compositions are given intravenously in the range of 1 to 100 µg/kg/min and various hemodynamic indices are recorded. Alternatively, in this experiment test compounds or pharmaceutical compositions are administered using an inhalation nebulizer at dose levels of 0.1-1 g/kg in 5-10 time period during each hypoxia period.

Example 8: In Vivo Animal Studies (Chronic Treatment, Continuous Intravenous Infusion)

This example demonstrates the efficacy of the compounds and pharmaceutical compositions described herein to retard the progression of disease in rats with monocrotaline-induced PH.

Rats (200-250 g) are surgically implanted with a pressure transducer equipped telemetry transmitter. The transmitter assembly is secured internally; the fluid-filled catheter is placed into the jugular vein with the tip of the pressure transducer positioned in the right ventricle for collection of right ventricular pressure (RVP) data. Additionally, all animals, with the exception of the sham group, are implanted with femoral vein cannulas for the purposes of dosing.

Monocrotaline (MCT) is administered to vehicle-control animals by subcutaneous injection. One week following the MCT injection, the vehicle-control animals are administered saline or a low or high dose of a test compound or pharmaceutical composition by continuous intravenous infusion for two weeks. The test and vehicle control article are administered by external pump. Weekly clinical observations are performed on animals.

For cardiovascular evaluations, RVP data is collected with animals allowed free movement in the home cage. The animals are monitored for at least 24 hours prior to MCT administration. RVP is also monitored at 24 hours following the end of the two week infusion, and occurs for at least 24 hours. All animals are necropsied at the end of the study. Weights of lungs and pulmonary artery, heart and each individual chamber are evaluated. The weights of the heart, LV, RV, and ratio to body weight are reported. The small pulmonary arteries from each animal are evaluated for medial thickness, neointima, and smooth muscle hypertrophy.

Example 9: In Vivo Animal Studies (Chronic Treatment, Oral Administration)

This example demonstrates the efficacy of the compounds and pharmaceutical compositions described herein to retard the progression of disease in rats with monocrotaline-induced PH.

The general methodology for this experiment is similar to that of Example 7 above. One difference is that the route of administration is oral, with a dosing regimen of once to four times daily at dose levels of 0.1-1 g/kg.

Example 10: In Vivo Animal Studies (Chronic Treatment, Continuous Intravenous Infusion)

This example demonstrates the efficacy of the compounds and pharmaceutical compositions described herein to reverse the progression of disease in rats with monocrotaline-induced PH.

In this study, rats (200-250 g) rats are surgically implanted with a pressure transducer equipped telemetry transmitter. The transmitter assembly is secured internally; the fluid-filled catheter is placed into the jugular vein with the tip of the pressure transducer positioned in the right ventricle for collection of right ventricular pressure (RVP) data. Additionally, all animals, with exception of sham group, are implanted with femoral vein cannulas for the purposes of dosing.

The vehicle and control article, monocrotaline (MCT), are administered by subcutaneous injection. Three weeks following the MCT injection, animals are administered saline or a low or high dose of a test compound or pharmaceutical composition by continuous intravenous infusion for three weeks. The test compound or pharmaceutical composition and vehicle control article are administered by external pump. Weekly clinical observations are performed on the animals.

For cardiovascular evaluations, RVP data is collected with animals allowed free movement in the home cage. The animals are monitored for at least 24 hours prior to MCT administration. RVP is also monitored for at least 24 hours following the end of the two week infusion. All animals are necropsied at the end of the study. Weights of lungs and pulmonary artery, heart and each individual chamber are evaluated. The weights of the heart, LV, RV, and ratio to body weight are reported. The small pulmonary arteries from each animal are evaluated for medial thickness, neointima, and smooth muscle hypertrophy.

Example 11: In Vivo Animal Studies (Chronic Treatment, Oral Administration)

This example demonstrates the efficacy of the compounds and pharmaceutical compositions described herein to reverse the progression of disease in rats with monocrotaline-induced PH.

The general methodology is similar to that of Example 9, with the exception that the route of administration is oral, with a dosing regimen of one to four times daily at dose levels of 0.1-1 g/kg.

Example 12: In Vivo Animal Studies (Chronic Treatment, Inhaled Administration)

This example demonstrates the efficacy of the compounds and pharmaceutical compositions described herein to retard progression of disease in rats with monocrotaline-induced PH.

The general methodology is similar to that of Example 7 above, with the exception that the route of administration is via inhalation, with a dosing regimen of one to four times daily at dose levels of 0.1-1 g/kg.

Example 13: In Vivo Animal Studies (Chronic Treatment, Inhaled Administration)

This example demonstrates the efficacy of the compounds and pharmaceutical compositions described herein to reverse the progression of disease in rats with monocrotaline-induced PH.

The general methodology is similar to that of Example 7, with the exception that the route of administration is via inhalation, with a dosing regimen of one to four times daily at dose levels of 0.1-1 g/kg.

Example 14: In Vivo Animal Studies (Acute Treatment, Intravenous Infusion and Inhaled Administration)

This example demonstrates the efficacy of the compounds and pharmaceutical compositions described herein to lower pulmonary artery pressure in dogs with thromboxane-induced PH.

Experimental PH is induced by continuous infusion of a thromboxane A2 receptor agonist analog (for example U46619, Tocris Bioscience). The thromboxane A2 receptor agonist analog infusion rate (0.1-1 mg/kg/min) is adjusted to maintain a systolic pulmonary artery pressure (PAP) at 40 mmHg in anesthetized and mechanically ventilated dogs. The left femoral vein and artery are cannulated for dose administration and arterial blood pressure recording. The right jugular vein is cannulated with a pulmonary artery pressure catheter (Swan Ganz catheter), to measure both pulmonary arterial pressure (PAP) and pulmonary wedge pressure (PWP). This catheter is also used for measurement of cardiac output via thermodilution techniques following rapid injection of cold 5 mL saline. Electrocardiograms are monitored throughout the experiment.

Once a stable steady-state in hemodynamic is achieved, various doses of the test compounds or pharmaceutical compositions are given intravenously at dose rates in the range of 1 to 100 µg/kg/min and various hemodynamic indices are recorded. Alternatively, in this experiment the test compounds or pharmaceutical compositions are administered using an inhalation nebulizer at dose levels of 0.1-1 g/kg in 5-10 time period.

Example 15: In Vivo Human Studies (Acute Treatment, Intravenous Infusion and Inhaled Administration)

This example demonstrates the efficacy of HNO donors to lower pulmonary artery pressure in human subjects with various causes of pulmonary hypertension.

Patients (either gender) with various causes of pulmonary hypertension are selected for this study. Baseline hemodynamic characteristics of the patients are assessed by collected various hemodynamic indices utilizing right heart catheterization (e.g. right atrial pressure, mean pulmonary artery pressure, cardiac index), and blood gas profiling. Cardiac rhythm is monitored using continuous electrocardiography, and arterial pressure is monitored using a pressure cuff. Patients are tested for reversibility of pulmonary hypertension using nitric oxide (NO) by inhalation. Hemodynamic indices are then reassessed. Once all indices have returned to baseline upon cessation of NO delivery, and a baseline is established, various doses of HNO donors are given intravenously at dose rates in the range of 1 to 100 µg/kg/min (either continuous dose or in a dose-escalation fashion) and various hemodynamic indices are recorded. Alternatively, in this experiment HNO donors are administered using an inhalation nebulizer at dose levels of 0.1-1 g/kg in 5-10 minute time period. Hemodynamic indices are assessed at various time points during the infusion period. A few patients receive placebo instead of HNO donor in a double-blind randomized fashion. From the data collected during various periods of the trial, the pulmonary and systemic vascular resistances are calculated.

Example 16: Human Clinical Trials to Determine Ability of Compounds or Pharmaceutical Compositions to Treat, Prevent and/or Delay Onset and/or Development of a Disease or Condition Any of the compounds and pharmaceutical compositions described herein can also be tested in humans to determine the ability of the compounds or pharmaceutical compositions to treat, prevent and/or delay the onset and/or the development of a disease or condition. Standard methods can be used for these clinical trials. In one exemplary method, individuals with a disease or condition described herein, such as congestive heart failure, are enrolled in a tolerability, pharmacokinetics and pharmacodynamics phase I study of a therapy using the compounds described herein in standard protocols. Then a phase II, double-blind randomized controlled trial is performed to determine the efficacy of the compounds using standard protocols.

It will be apparent to those skilled in the art that specific embodiments of the invention may be directed to one, some or all of the above- and below-indicated embodiments in any combination.

While the invention has been described in some detail by way of illustration and example for purposes of clarity of understanding, it is apparent to those skilled in the art that various changes may be made and equivalents may be substituted without departing from the true spirit and scope of the invention. Therefore, the description and examples should not be construed as limiting the scope of the invention.

All references, publications, patents, and patent applications disclosed herein are hereby incorporated by reference in their entirety.

What is claimed is:

1. A compound of formula (I)

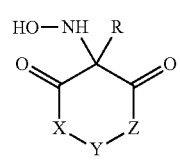

(I)

or a pharmaceutically acceptable salt thereof, wherein:
X and Z are independently —O— or —S—;
Y is —CR$^5$R$^6$—;
R is selected from $C_1$-$C_8$ alkyl, $C_2$-$C_8$ alkenyl, $C_2$-$C_8$ alkynyl, $C_1$-$C_8$ alkoxy, $C_5$-$C_{10}$ aryl, —C(=O)R$^7$, —C(=S)R$^7$, —C(=NR$^7$)R$^8$, and —C(=NOR$^7$)R$^8$, wherein the alkyl, alkenyl, alkynyl, alkoxy and aryl are unsubstituted or substituted with one or more substituents; and
R$^3$, R$^4$, R$^5$, R$^6$, R$^7$ and R$^8$ are independently selected from —H, $C_1$-$C_8$ alkyl, $C_2$-$C_8$ alkenyl, $C_2$-$C_8$ alkynyl, $C_5$-$C_{10}$ aryl, $C_5$-$C_{10}$ heterocycloalkyl, $C_5$-$C_{10}$ heterocycloalkenyl, and $C_5$-$C_{10}$ heteroaryl, wherein the alkyl, alkenyl, alkynyl, aryl, heterocycloalkyl, heterocycloalkenyl and heteroaryl are unsubstituted or substituted with one or more substituents.

2. The compound of claim 1, wherein R is $C_1$-$C_8$ alkyl, wherein the alkyl is unsubstituted or substituted with one or more substituents.

3. The compound of claim 1, wherein R is $C_1$-$C_4$ alkyl.

4. The compound of claim 1, wherein R is —C(=NOR$^5$)R$^6$.

5. The compound of claim 1, wherein R is —C(=NOR$^5$)R$^6$; and R$^5$ and R$^6$ are independently $C_1$-$C_4$ alkyl.

6. The compound of any one of claims 1, and 2 to 5, wherein X and Z are each —O—.

7. The compound of claim 1, wherein the compound is:

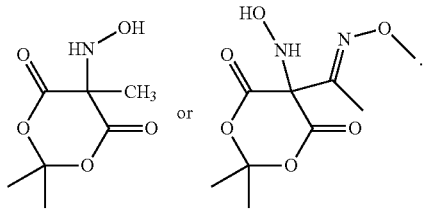

8. A pharmaceutical composition comprising:
a compound of claim 1; and
a pharmaceutically acceptable excipient.

9. A kit comprising:
a compound of claim 1; and
instructions for treating a condition that is responsive to nitroxyl therapy.

10. A pharmaceutical composition comprising:
a compound of claim 7; and
a pharmaceutically acceptable excipient.

11. A kit comprising:
a compound of claim 7; and
instructions for treating a condition that is responsive to nitroxyl therapy.

* * * * *

UNITED STATES PATENT AND TRADEMARK OFFICE
CERTIFICATE OF CORRECTION

PATENT NO. : 9,862,699 B2
APPLICATION NO. : 15/290872
DATED : January 9, 2018
INVENTOR(S) : John P. Toscano et al.

Page 1 of 1

It is certified that error appears in the above-identified patent and that said Letters Patent is hereby corrected as shown below:

In the Specification

Column 1, delete Lines 19-22 and insert the following:
--STATEMENT OF GOVERNMENTAL INTEREST
This invention was made with government support under grant number CHE0911305, awarded by the National Science Foundation. The government has certain rights in the invention.--

Signed and Sealed this
Thirteenth Day of November, 2018

Andrei Iancu
*Director of the United States Patent and Trademark Office*